US012133528B2

(12) United States Patent
Reynolds et al.

(10) Patent No.: US 12,133,528 B2
(45) Date of Patent: Nov. 5, 2024

(54) INSECTICIDAL PROTEINS

(71) Applicant: SYNGENTA PARTICIPATIONS AG, Basel (CH)

(72) Inventors: Clarence Michael Reynolds, Research Triangle Park, NC (US); Christopher Fleming, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 759 days.

(21) Appl. No.: 16/980,715

(22) PCT Filed: Mar. 7, 2019

(86) PCT No.: PCT/US2019/021093
§ 371 (c)(1),
(2) Date: Sep. 14, 2020

(87) PCT Pub. No.: WO2019/177855
PCT Pub. Date: Sep. 19, 2019

(65) Prior Publication Data
US 2021/0251240 A1 Aug. 19, 2021

Related U.S. Application Data

(60) Provisional application No. 62/643,275, filed on Mar. 15, 2018.

(51) Int. Cl.

| | |
|---|---|
| *C12N 15/82* | (2006.01) |
| *A01N 37/46* | (2006.01) |
| *A01N 63/50* | (2020.01) |
| *C07K 14/195* | (2006.01) |

(52) U.S. Cl.
CPC ............ *A01N 37/46* (2013.01); *A01N 63/50* (2020.01); *C07K 14/195* (2013.01); *C12N 15/8286* (2013.01)

(58) Field of Classification Search
None
See application file for complete search history.

(56) References Cited

U.S. PATENT DOCUMENTS

| | | | | |
|---|---|---|---|---|
| 9,879,277 B2 * | 1/2018 | Abad | ................. | C12N 15/8286 |
| 10,221,429 B2 | 3/2019 | Thayer et al. | | |
| 10,457,957 B2 * | 10/2019 | Abad | .................. | C07K 14/325 |
| 2016/0031949 A1 * | 2/2016 | Abad | ..................... | A01N 37/46 435/468 |
| 2018/0066277 A1 | 3/2018 | Parks | | |

OTHER PUBLICATIONS

GenBank No. CP003346.1, submitted Jan. 8, 2015.*
Hayatsu et al. The ISME Journal (2017) 11, 1130-1141.*
Keskin et al.2004. Protein Science, 13:1043-1055.*
Guo et al. Proceedings of the National Academy of Sciences USA 101: 9205-9210.*
Genbank Submission AP014836.1, Candidaus Nitrosoglobus terrae DNA, complete genome, Apr. 26, 2017, https://www.ncbi.mlm.nih.gov/nuccore/AP014836.1.
Genbank Submisson CP003346.1 titled Echinicola vietnamensis DSM 17526, complete genome , Jan. 8, 2015, retrieved May 3, 2019: https:/www.ncbi.nlm.nih.gov/nuccore/CP003346.
International Search Report cited in International application No. PCT/US19/21093, mailed Jul. 5, 2019.
Extended ESR for EP1976721537, mailed on Nov. 30, 2021).
Ibargutxi, M.A., et al., Use of Bacillus thuringiensis Toxins for Control of the Cotton Pest Earias insulana (Boisd.) (Lepidoptera: Noctuidae), Applied and Environmental Microbiology, Jan. 2006, p. 437-442 0099-2240/06/$08.00+0 doi: 10.1128/AEM.72.1.437-442. 2006, Jul. 21, 2005.

* cited by examiner

*Primary Examiner* — Mykola V. Kovalenko
(74) *Attorney, Agent, or Firm* — Katherine Seguin

(57) ABSTRACT

Compositions and methods for controlling plant pests are disclosed. In particular, novel insecticidal proteins having toxicity against Coleopteran and/or Lepidopteran insect pests are provided. Nucleic acid molecules encoding the novel insecticidal proteins are also provided. Methods of making the insecticidal proteins and methods of using the insecticidal proteins and nucleic acids encoding the insecticidal proteins of the invention, for example in transgenic plants to confer protection from insect damage, are also disclosed.

19 Claims, No Drawings

Specification includes a Sequence Listing.

ововidal PROTEINS

INSECTICIDAL PROTEINS

RELATED APPLICATION INFORMATION

This application is a 371 of International Application No. PCT/US2019/021093, filed Mar. 7, 2019, which claims priority to U.S. Provisional Application No. 62/643,275, filed Mar. 15, 2018, the contents of which are incorporated herein by reference herein.

SEQUENCE LISTING

A Sequence Listing in ASCII text format, submitted under 37 C.F.R. § 1.821, entitled "81547-WO-REG-ORG-P-1 SEQLIST.txt", 145 kilobytes in size, generated on Sep. 9, 2020 and filed via EFS-Web is provided in lieu of a paper copy. This Sequence Listing is hereby incorporated by reference into the specification for its disclosures.

FIELD OF THE INVENTION

The present invention relates to the fields of protein engineering, plant molecular biology and pest control. More particularly the invention relates to a novel protein and its variants having insecticidal activity, nucleic acids whose expression results in the insecticidal proteins, and methods of making and methods of using the insecticidal proteins and corresponding nucleic acids to control insects.

BACKGROUND

Insect pests are a major cause of crop losses. In the US alone, billions of dollars are lost every year due to infestation by various genera of insects. In addition to losses in field crops, insect pests are also a burden to vegetable and fruit growers, to producers of ornamental flowers, and they are a nuisance to gardeners and homeowners.

Species of corn rootworm are considered to be the most destructive corn pests. In the United States, the three important species are *Diabrotica virgifera virgifera*, the western corn rootworm, *D. longicornis barberi*, the northern corn rootworm and *D. undecimpunctata howardi*, the southern corn rootworm. Only western and northern corn rootworms are considered primary pests of corn in the US Corn Belt. Additionally, an important corn rootworm pest in the Southern US is the Mexican corn rootworm, *Diabrotica virgifera zeae*. Corn rootworm larvae cause the most substantial plant damage by feeding almost exclusively on corn roots. This injury has been shown to increase plant lodging, to reduce grain yield and vegetative yield as well as alter the nutrient content of the grain. Larval feeding also causes indirect effects on corn by opening avenues through the roots for bacterial and fungal infections which lead to root and stalk rot diseases. Adult corn rootworms are active in cornfields in late summer where they feed on ears, silks and pollen, thus interfering with normal pollination.

Corn rootworms are mainly controlled by intensive applications of chemical pesticides, which are active through inhibition of insect growth, prevention of insect feeding or reproduction, or cause death. Good corn rootworm control can thus be reached, but these chemicals can sometimes also affect other, beneficial organisms. Another problem resulting from the wide use of chemical pesticides is the appearance of resistant insect varieties. Yet another problem is due to the fact that corn rootworm larvae feed underground thus making it difficult to apply rescue treatments of insecticides. Therefore, most insecticide applications are made prophylactically at the time of planting. This practice results in a large environmental burden. This has been partially alleviated by various farm management practices, but there is an increasing need for alternative pest control mechanisms.

Biological pest control agents, such as *Bacillus thuringiensis* (Bt) strains expressing pesticidal toxins like δ-endotoxins (delta-endotoxins; also called crystal toxins or Cry proteins), have been applied to crop plants with satisfactory results against insect pests. The δ-endotoxins are proteins held within a crystalline matrix that are known to possess insecticidal activity when ingested by certain insects. Several native Cry proteins from *Bacillus thuringiensis*, or engineered Cry proteins, have been expressed in transgenic crop plants and exploited commercially to control certain Lepidopteran and Coleopteran insect pests. For example, starting in 2003, transgenic corn hybrids that control corn rootworm by expressing a Cry3Bb1, Cry34Ab1/Cry35Ab1 or modified Cry3A (mCry3A) or Cry3Ab (eCry3.1Ab) protein have been available commercially in the US.

Although the usage of transgenic plants expressing Cry proteins has been shown to be extremely effective, insect pests that now have resistance against the Cry proteins expressed in certain transgenic plants are known. Therefore, there remains a need to identify new and effective pest control agents that provide an economic benefit to farmers and that are environmentally acceptable. Particularly needed are proteins that are toxic to *Diabrotica* species, a major pest of corn, that have a different mode of action than existing insect control products as a way to mitigate the development of resistance. Furthermore, delivery of insect control agents through products that minimize the burden on the environment, as through transgenic plants, are desirable.

SUMMARY

In view of these needs, the present invention provides novel insecticidal proteins, namely NitromobCRW and proteins which are substantially identical to NitromobCRW and its variants. The proteins of the invention have toxicity to corn rootworm (*Diabrotica* spp). The proteins of the invention may also have toxicity to other Coleopterans and/or to Lepidopterans. The invention is further drawn to nucleic acid molecules that encode NitromobCRW or its variants, their complements, or which are substantially identical to NitromobCRW and its variants.

Also included in the invention are vectors containing such recombinant (or complementary thereto) nucleic acids; a plant or microorganism which includes and enables expression of such nucleic acids; plants transformed with such nucleic acids, for example transgenic corn plants; the progeny of such plants which contain the nucleic acids stably incorporated and hereditable in a Mendelian manner, and/or the seeds of such plants and such progeny. The invention also includes methods of breeding to introduce a transgene comprising a nucleic acid molecule of the invention into a progeny plant and into various germplasms.

The invention also includes compositions and formulations containing NitromobCRW or its variants, which are capable of inhibiting the ability of insect pests to survive, grow and/or reproduce, or of limiting insect-related damage or loss to crop plants, for example applying NitromobCRW or its variants as part of compositions or formulations to insect-infested areas or plants, or to prophylactically treat insect-susceptible areas or plants to confer protection against the insect pests.

The invention is further drawn to a method of making NitromobCRW or its variants and to methods of using the nucleic acids, for example in microorganisms to control insects or in transgenic plants to confer protection from insect damage.

The novel proteins described herein are active against insects. For example, in embodiments, the proteins of the present invention can be used to control economically important insect pests, including Coleopteran insects such as western corn rootworm (WCR), northern corn rootworm (NCR), southern corn rootworm (SCR) and/or Mexican corn rootworm (*D. virgifera zeae*). The insecticidal proteins of the invention can be used singly or in combination with other insect control strategies to confer enhanced pest control efficiency against the same insect pest and/or to increase the spectrum of target insects with minimal environmental impact.

Other aspects and advantages of the present invention will become apparent to those skilled in the art from a study of the following description of the invention and non-limiting examples.

BRIEF DESCRIPTION OF THE SEQUENCES IN THE SEQUENCE LISTING

The nucleic acid sequences listed in the accompanying sequence listing are shown using standard letter abbreviations for nucleotide bases, as defined in 37 C.F.R.§ 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence reference to the nucleic acid sequence, unless it is explicitly stated to be otherwise (or it is clear to be otherwise from the context in which the sequence appears). Furthermore, as it is understood in the art that the nucleotide sequence of an RNA strand is determined by the sequence of the DNA from which it was transcribed (but for the substitution of uracil (U) nucleobases for thymine (T)), an RNA sequence is included by any reference to the DNA sequence encoding it. In the accompanying sequence listing:

SEQ ID NO: 1 is the NitromobCRW *E. coli* optimized nucleotide sequence.

SEQ ID NO: 2 is the NitromobCRW variant I98L nucleotide sequence.

SEQ ID NO: 3 is the NitromobCRW variant V99L nucleotide sequence.

SEQ ID NO: 4 is the NitromobCRW variant I175L nucleotide sequence.

SEQ ID NO: 5 is the NitromobCRW variant I208L nucleotide sequence.

SEQ ID NO: 6 is the NitromobCRW variant I215L nucleotide sequence.

SEQ ID NO: 7 is the NitromobCRW variant I215F nucleotide sequence.

SEQ ID NO: 8 is the NitromobCRW variant I215Y nucleotide sequence.

SEQ ID NO: 9 is the NitromobCRW variant Y213L/I215L nucleotide sequence.

SEQ ID NO: 10 is the NitromobCRW variant I245L nucleotide sequence.

SEQ ID NO: 11 is the NitromobCRW variant I255L nucleotide sequence.

SEQ ID NO: 12 is the NitromobCRW variant I265L nucleotide sequence.

SEQ ID NO: 13 is the NitromobCRW variant I257L nucleotide sequence.

SEQ ID NO: 14 is the NitromobCRW variant G216A nucleotide sequence.

SEQ ID NO: 15 is the NitromobCRW variant G216L nucleotide sequence.

SEQ ID NO: 16 is the NitromobCRW variant V122L nucleotide sequence.

SEQ ID NO: 17 is the NitromobCRW variant V167L nucleotide sequence.

SEQ ID NO: 18 is the NitromobCRW variant V220L nucleotide sequence.

SEQ ID NO: 19 is the NitromobCRW insertion variant L214-Leu-I215 nucleotide sequence.

SEQ ID NO: 20 is the NitromobCRW insertion variant I215-Leu-G216 nucleotide sequence.

SEQ ID NO: 21 is the NitromobCRW variant Y213F/I215L nucleotide sequence.

SEQ ID NO: 22 is the NitromobCRW variant I175L/I215L nucleotide sequence.

SEQ ID NO: 23 is the NitromobCRW variant I208L/I215L nucleotide sequence.

SEQ ID NO: 24 is the NitromobCRW variant I215L/I255L nucleotide sequence.

SEQ ID NO: 25 is the NitromobCRW variant I255L/I257L nucleotide sequence.

SEQ ID NO: 26 is the NitromobCRW variant L214S/I215L nucleotide sequence.

SEQ ID NO: 27 is the NitromobCRW variant V203S/M204L nucleotide sequence.

SEQ ID NO: 28 is the NitromobCRW variant T218L nucleotide sequence.

SEQ ID NO: 29 is the NitromobCRW variant T218F nucleotide sequence.

SEQ ID NO: 30 is the NitromobCRW variant V185L nucleotide sequence.

SEQ ID NO: 31 is the NitromobCRW variant V193L/I215L nucleotide sequence.

SEQ ID NO: 32 is the NitromobCRW variant E196L/I215L nucleotide sequence.

SEQ ID NO: 33 is the NitromobCRW variant E186L/I215L nucleotide sequence.

SEQ ID NO: 34 is the NitromobCRW variant V177L/I215L nucleotide sequence.

SEQ ID NO: 35 is the NitromobCRW variant Y213L nucleotide sequence.

SEQ ID NO: 36 is the NitromobCRW variant V203S/M204L/I215L nucleotide sequence.

SEQ ID NO: 37 is the NitromobCRW native nucleotide sequence.

SEQ ID NO: 38 is the NitromobCRW variant Y213L/I215L maize codon-optimized nucleotide sequence.

SEQ ID NO: 39 is the NitromobCRW native amino acid sequence.

SEQ ID NO: 40 is the NitromobCRW variant I98L amino acid sequence.

SEQ ID NO: 41 is the NitromobCRW variant V99L amino acid sequence.

SEQ ID NO: 42 is the NitromobCRW variant I175L amino acid sequence.

SEQ ID NO: 43 is the NitromobCRW variant I208L amino acid sequence.

SEQ ID NO: 44 is the NitromobCRW variant I215L amino acid sequence.

SEQ ID NO: 45 is the NitromobCRW variant I215F amino acid sequence.

SEQ ID NO: 46 is the NitromobCRW variant I215Y amino acid sequence.

SEQ ID NO: 47 is the NitromobCRW variant Y213L/I215L amino acid sequence.

SEQ ID NO: 48 is the NitromobCRW variant I245L amino acid sequence.

SEQ ID NO: 49 is the NitromobCRW variant I255L amino acid sequence.

SEQ ID NO: 50 is the NitromobCRW variant I265L amino acid sequence.

SEQ ID NO: 51 is the NitromobCRW variant I257L amino acid sequence.

SEQ ID NO: 52 is the NitromobCRW variant G216A amino acid sequence.

SEQ ID NO: 53 is the NitromobCRW variant G216L amino acid sequence.

SEQ ID NO: 54 is the NitromobCRW variant V122L amino acid sequence.

SEQ ID NO: 55 is the NitromobCRW variant V167L amino acid sequence.

SEQ ID NO: 56 is the NitromobCRW variant V220L amino acid sequence.

SEQ ID NO: 57 is the NitromobCRW insertion variant L214-Leu-I215 amino acid sequence.

SEQ ID NO: 58 is the NitromobCRW insertion variant I215-Leu-G216 amino acid sequence.

SEQ ID NO: 59 is the NitromobCRW variant Y213F/I215L amino acid sequence.

SEQ ID NO: 60 is the NitromobCRW variant I175L/I215L amino acid sequence.

SEQ ID NO: 61 is the NitromobCRW variant I208L/I215L amino acid sequence.

SEQ ID NO: 62 is the NitromobCRW variant I215L/I255L amino acid sequence.

SEQ ID NO: 63 is the NitromobCRW variant I255L/I257L amino acid sequence.

SEQ ID NO: 64 is the NitromobCRW variant L214S/I215L amino acid sequence.

SEQ ID NO: 65 is the NitromobCRW variant V203S/M204L amino acid sequence.

SEQ ID NO: 66 is the NitromobCRW variant T218L amino acid sequence.

SEQ ID NO: 67 is the NitromobCRW variant T218F amino acid sequence.

SEQ ID NO: 68 is the NitromobCRW variant V185L amino acid sequence.

SEQ ID NO: 69 is the NitromobCRW variant V193L/I215L amino acid sequence.

SEQ ID NO: 70 is the NitromobCRW variant E196L/I215L amino acid sequence.

SEQ ID NO: 71 is the NitromobCRW variant E186L/I215L amino acid sequence.

SEQ ID NO: 72 is the NitromobCRW variant V177L/I215L amino acid sequence.

SEQ ID NO: 73 is the NitromobCRW variant Y213L amino acid sequence.

SEQ ID NO: 74 is the NitromobCRW variant V203S/M204L/I215L amino acid sequence.

SEQ ID NO: 75 is a NitromobCRW-Cterm-SUMO nucleotide sequence.

SEQ ID NO: 76 is an amino acid sequence of a NitromobCRW-Cterm-SUMO extension peptide.

SEQ ID NO: 77 is a NitromobCRW Y213L/I215L-Cterm-SUMO amino acid sequence.

Definitions

For clarity, certain terms used in the specification are defined and presented as follows:

"Activity" of the insecticidal proteins of the invention is meant that the insecticidal proteins function as orally active insect control agents, have a toxic effect, and/or are able to disrupt or deter insect feeding, which may or may not cause death of the insect. When an insecticidal protein of the invention is delivered to the insect, the result is typically death of the insect, or the insect does not feed upon the source that makes the insecticidal protein available to the insect. "Pesticidal" is defined as a toxic biological activity capable of controlling a pest, such as an insect, nematode, fungus, bacteria, or virus, preferably by killing or destroying them. "Insecticidal" is defined as a toxic biological activity capable of controlling insects, preferably by killing them. A "pesticidal agent" is an agent that has pesticidal activity. An "insecticidal agent" is an agent that has insecticidal activity.

"Associated with/operatively linked" refer to two nucleic acids that are related physically or functionally. For example, a promoter or regulatory DNA sequence is said to be "associated with" a DNA sequence that codes for RNA or a protein if the two sequences are operatively linked, or situated such that the regulatory DNA sequence will affect the expression level of the coding or structural DNA sequence.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" an insecticidal protein means that the insecticidal protein comes in contact with an insect, resulting in a toxic effect and control of the insect. The insecticidal protein may be delivered in many recognized ways, e.g., through a transgenic plant expressing the insecticidal protein, formulated protein composition(s), sprayable protein composition(s), a bait matrix, or any other art-recognized toxin delivery system.

"Effective insect-controlling amount" means that concentration of an insecticidal protein that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may have at least one of its components heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used. Any available terminator known to function in plants can be used in the context of this invention.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

A "gene" is a defined region that is located within a genome and comprises a coding nucleic acid sequence and typically also comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

"Gene of interest" refers to any nucleic acid molecule which, when transferred to a plant, confers upon the plant a desired trait such as antibiotic resistance, virus resistance, insect resistance, disease resistance, or resistance to other pests, herbicide tolerance, abiotic stress tolerance, male sterility, modified fatty acid metabolism, modified carbohydrate metabolism, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence or nucleic acid molecule is a nucleic acid sequence or nucleic acid molecule not naturally associated with a host cell into which it is introduced, including non-naturally occurring multiple copies of a naturally occurring nucleic acid sequence. A heterologous nucleic acid sequence or nucleic acid molecule may comprise a chimeric sequence such as a chimeric expression cassette, where the promoter and the coding region are derived from multiple source organisms. The promoter sequence may be a constitutive promoter sequence, a tissue-specific promoter sequence, a chemically-inducible promoter sequence, a wound-inducible promoter sequence, a stress-inducible promoter sequence, or a developmental stage-specific promoter sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Identity" or "percent identity" refers to the degree of similarity between two nucleic acid or protein sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or at least about 85%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. *Nuc. Acids Res.,* 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Another indication that two nucleic acids are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes part I chapter 2 "Overview of principles of hybridization and the strategy of nucleic acid probe assays"* Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

A further indication that two nucleic acids or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated toxin is a nucleic acid molecule or toxin that, by the hand of man, exists apart from its native environment and is therefore not a product of nature. An isolated nucleic acid molecule or toxin may exist in a purified form or may exist in a non-native environment such as, for example without limitation, a recombinant microbial cell, plant cell, plant tissue, or plant.

A "nucleic acid molecule" or "nucleic acid sequence" is a segment of single- or double-stranded DNA or RNA that can be isolated from any source. In the context of the present invention, the nucleic acid molecule is typically a segment of DNA. In some embodiments, the nucleic acid molecules of the invention are isolated nucleic acid molecules.

The terms "protein," "peptide" and "polypeptide" are used interchangeably herein.

As used herein, "codon optimized" sequence means the nucleotide sequence of a recombinant, transgenic, or synthetic polynucleotide wherein the codons are chosen to reflect the particular codon bias that a host cell may have. This is done in such a way so as to preserve the amino acid sequence of the polypeptide encoded by the codon optimized polynucleotide. In certain embodiments, the nucleotide sequence of the recombinant DNA construct includes a sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase and initiates transcription of the DNA. The promoter region may also include other elements that act as regulators of gene expression.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

"Transformation" is a process for introducing heterologous nucleic acid into a host cell or organism. In particular embodiments, "transformation" means the stable integration of a DNA molecule into the genome (nuclear or plastid) of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G) Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DETAILED DESCRIPTION

This invention relates to novel insecticidal proteins which have activity against Coleopterans, for example, *Diabrotica virgifera virgifera* (western corn rootworm; WCR), *Diabrotica barberi* (northern corn rootworm; NCR), and/or *Diabrotica undecimpunctata howardi* (southern corn rootworm; SCR) and/or other *Diabrotica* species including *Diabrotica virgifera zeae* (Mexican corn rootworm), and/or other Coleopteran insect pests such as Colorado Potato Beetle. In embodiments, a novel insecticidal protein of the invention may have activity against Lepidopteran species. The present invention also relates to nucleic acids whose expression results in insecticidal proteins of the invention, and to the making and using of the insecticidal proteins to control insect pests. In embodiments, the expression of the nucleic acids results in insecticidal proteins that can be used to control Coleopteran insects such as western, northern and/or southern corn rootworm, particularly when expressed in a transgenic plant such as a transgenic corn plant.

The present invention further encompasses a nucleic acid molecule comprising a nucleotide sequence that encodes an insecticidal protein of the invention. The nucleotide sequence may be optimized for expression in bacteria, such as *Escherichia coli*, or for expression in a plant, such as *Zea mays*. A nucleotide sequence optimized for expression in a heterologous organism, such as a species of bacteria different from where it originated or a plant, is not naturally occurring. In one aspect of this embodiment, the nucleic acid molecule comprises the nucleotide sequence of any of SEQ ID NO: 1 to 38, or a complement thereof. Specifically exemplified teachings of methods to make nucleic acid molecules that encode the insecticidal proteins of the invention can be found in the examples of the present application. Those skilled in the art will recognize that modifications can be made to the exemplified methods to make the insecticidal proteins encompassed by the present invention.

A skilled person would recognize that a transgene for commercial use, such as a nucleic acid molecule that comprises any one of SEQ ID NO: 1 to 38, or a complement thereof may have relatively minor modifications to the nucleic acid sequence to comply with governmental regulatory standards. Such modifications would not affect the function of the resulting molecule, which would be substantially identical to SEQ ID NO: 1 to 38. A skilled person would recognize that the modified nucleic acid molecule would be essentially the same as the starting molecule, and is encompassed by the present invention.

The present invention also encompasses a nucleic acid molecule that comprises (a) a nucleotide sequence of any one of SEQ ID NO: 1 to 38; (b) a nucleotide sequence that is sequence at least 45% identical, at least 50% identical, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to any one of the nucleotide sequences of SEQ ID NO: 1 to 38; (c) a nucleotide sequence that encodes a polypeptide, wherein the amino acid sequence of the polypeptide comprises SEQ ID NO: 39 to 74, and has insect control activity; (d) a nucleotide sequence that encodes a polypeptide, wherein the amino acid sequence of the polypeptide is at least 45% identical, at least 50% identical, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to any one of the amino acid sequences of SEQ ID NOs: 39 to 74; or (e) a nucleotide sequence that is complementary to the nucleotide sequence of any one of (a) to (d) above.

The present invention further encompasses an expression cassette comprising a promoter operably linked to a heterologous nucleotide sequence that comprises: (a) a nucleotide sequence of any one of SEQ ID NOs: 1 to 38; (b) a nucleotide sequence that is at least 45% identical, at least 50% identical, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of any one of SEQ ID NOs: 1 to 38; (c) a nucleotide sequence that encodes a polypeptide, wherein the amino acid sequence of the polypeptide comprises SEQ ID NOs: 39 to 74, and has insect control activity; (d) a nucleotide sequence that encodes a polypeptide, wherein the amino acid sequence of the polypeptide is at least 45% identical, at least 50% identical, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the amino acid sequence of any one of SEQ ID NOs: 39 to 74; or (e) a nucleotide sequence that is complementary to the nucleotide sequence of any one of (a) to (d) above. In some embodiments, the present invention encompasses an expression cassette comprising a heterologous nucleic acid molecule comprising a nucleotide sequence that encodes a polypeptide, wherein the amino acid sequence of the polypeptide is at least 93% identical to the amino acid sequence of SEQ ID NO: 39 to 74. The expression cassette comprises a promoter operably linked to a heterologous nucleotide sequence and is not naturally occurring.

The present invention also encompasses recombinant vectors or constructs, which may also be referred to as vectors or constructs, comprising the expression cassettes and/or the nucleic acid molecules of this invention. In such vectors, the nucleic acids are preferably in expression cassettes comprising regulatory elements for expression of the nucleotide molecules in a host cell capable of expressing the nucleotide molecules. Such regulatory elements usually comprise promoter and termination signals and preferably also comprise elements allowing efficient translation of polypeptides encoded by the nucleic acids of the present invention. Vectors comprising the nucleic acids are may be capable of replication in particular host cells, preferably as extrachromosomal molecules, and are therefore used to amplify the nucleic acids of this invention in the host cells. The present invention also encompasses a host cell that contains an expression cassette or a nucleic acid molecule of the invention. In one embodiment, host cells for such vectors are microorganisms, such as bacteria, in particular *Bacillus thuringiensis* or *E. coli*, or such as fungi such as yeast. In another embodiment, host cells for such recombinant vectors are endophytes or epiphytes. In yet another embodiment, such vectors are viral vectors and are used for replication of the nucleotide sequences in particular host cells, e.g. insect cells or plant cells. Recombinant vectors are also used for transformation of the nucleotide molecules of this invention into host cells, whereby the nucleotide molecules are stably integrated into the DNA of a transgenic host. In one embodiment, the transgenic host is plant, for example a monocot plant, such as a corn plant or a wheat plant. In embodiments, the transgenic host plant is a dicot plant, such as a soybean plant or cotton plant.

In another embodiment, at least one of the nucleic acids of the invention is inserted into an appropriate expression cassette, comprising a promoter and termination signal. Expression of the nucleic acid may be constitutive, or an inducible promoter responding to various types of stimuli to initiate transcription may be used. In another embodiment, the cell in which the insecticidal protein of the invention is expressed is a microorganism, such as a virus, bacteria, or a fungus. In yet another embodiment, a virus, such as a baculovirus, contains a nucleic acid of the invention in its genome and expresses large amounts of the corresponding insecticidal protein after infection of appropriate eukaryotic cells that are suitable for virus replication and expression of the nucleic acid. The insecticidal protein thus produced is used as an insecticidal agent. Alternatively, baculoviruses engineered to include the nucleic acid are used to infect insects in vivo and kill them either by expression of the insecticidal toxin or by a combination of viral infection and expression of the insecticidal toxin. In a further embodiment, the present invention also encompasses a method for producing a polypeptide with insecticidal activity, comprising culturing the host cell under conditions in which the nucleic acid molecule encoding the polypeptide is expressed.

Bacterial cells are also hosts for the expression of the nucleic acids of the invention. In one embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleic acids for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In:Industrial Microorganisms:Basic and Applied Molecular Genetics, Eds. Baltz et al., American Society for Microbiology, *Washington* (1993)). Alternate systems for overexpression rely for example, on yeast vectors and include the use of *Pichia, Saccharomyces* and *Kluyveromyces* (Sreekrishna, In:Industrial microorganisms:basic and applied molecular genetics, Baltz, Hegeman, and Skatrud eds., American Society for Microbiology, Washington (1993); Dequin & Bane, Biotechnology L2:173-177 (1994); van den Berg et al., *Biotechnology* 8:135-139 (1990)).

Certain insecticidal proteins have been expressed in plants and seed from such plants are sold annually to farmers for use in controlling various insect pests. Such self-protected insecticidal products are subject to review and registration by various regulatory agencies including, for example, the US Environmental Protection Agency (EPA).

Dietary exposure is the major route by which humans can be exposed to insecticidal proteins expressed in transgenic plants. Acute oral mammalian toxicity and protein digestibility are the end points for EPA's human health risk assessment. Further scientific evidence of the safety of insecticidal proteins is that they have been shown to be rapidly degraded in vitro using simulated gastric fluids. For example, results of seven in vitro assays conducted with representative Cry1, Cry2, and Cry3 proteins establish that the proteins are rapidly degraded, typically within 30 seconds. These results support the broader conclusion that members of these groups of Cry proteins (that share significant amino acid sequence identity) are likely to be rapidly degraded following ingestion by humans. Similar tests are done for each transgenic protein expressed in plants. Another area of consideration is whether insecticidal proteins may induce an allergenic reaction. Demonstrated rapid in vitro degradation of the transgenic insecticidal protein should minimize the potential for such an occurrence. By comparison, food allergens generally persist in the in vitro gastrointestinal model, whereas common food proteins with no allergenic history degraded rapidly in simulated gastric fluid (Metcalfe et al. 1996).

A simulated gastric fluid (SGF) assay measures the in vitro digestibility of a test protein at tightly controlled conditions representative of the upper mammalian digestive tract. For example, bacterially produced test Cry protein (at a concentration of 0.5-5 mg/ml) was exposed to the enzyme pepsin (from porcine gastric mucosa, solubilized in 2 mg/ml NaCl, pH 1.2) at a ratio of 10 Units of pepsin activity/ng test protein over a time period of one hour at 37° C. Samples were removed at 1, 2, 5, 10, 30, and 60 minute timepoints and immediately quenched with the addition of pre-heated (95° C.-2 minutes) stop buffer (65% 0.5M Sodium Bicarbonate pH 11, 35% Tricine Loading Buffer) to immediately render pepsin inactive, and returned to heat for an additional 5 minutes. Once the assay was complete, time point samples and controls (test protein alone, pepsin alone) were examined by SDS-PAGE on a 10-20% Tris-Tricine gel (with peptides visible down to 1 kDa) to track the kinetics and level of digestion performed by pepsin. If the test protein or a significant polypeptide fragment of the text protein is visible at, for example, the 5 and/or 10 minute timepoints, then it is not digestible or not completely digestible by the SGF assay, and may be scored qualitatively as "no", or "not digestible". If the test protein and any significant polypeptide fragment is not visible at, for example, the 5 minute timepoint, then it is digestible by the SGF assay, and may be scored qualitatively as "yes" or "digestible".

The present invention also encompasses a polypeptide comprising an amino acid sequence at least 45% identical, at least 50% identical, at least 55%, at least 60%, at least 65%, at least 70%, at least 75%, at least 80%, at least 85%, at least 90%, at least 92%, at least 95%, at least 98%, at least 99% identical, or is 100% identical to any one of SEQ ID NO: 39 to 74, and further comprising an introduced protease cleavage site. The introduced protease cleavage site is not naturally occurring, and is introduced into the polypeptide sequence, as a substitution mutation or as an insertion or deletion mutation. The introduced protease cleavage site may be introduced by the insertion of at least one leucine residue in a polypeptide sequence comprising any one of SEQ ID NO: 39 to 74. The introduced mutation may destabilize the polypeptide, so that a protease may gain access to a cleavage site which it previously did not have access to due to tight and/or stable folding of the protein, or to steric hindrance. The introduced protease cleavage site may be an introduced mutation in the polypeptide sequence which is recognized by a protease, such as chymotrypsin, trypsin, or pepsin, as a site for proteolytic cleavage. In some embodiments, the introduced protease cleavage site may alter an existing protease cleavage site so that it is recognized by a different protease. Protease cleavage sites for chymotrypsin, trypsin, and pepsin are well-known in the art. Chymotrypsin preferentially cleaves peptide amide bonds where the carboxyl side of the amide bond (the P1 position) is a large hydrophobic amino acid (tyrosine, tryptophan, and phenylalanine). Trypsin cleaves peptide chains mainly at the carboxyl side of the amino acids lysine or arginine, except when either is followed by proline. Pepsin is most efficient in cleaving peptide bonds between hydrophobic and preferably aromatic amino acids such as phenylalanine, tryptophan, tyrosine, and leucine. These cleavage sites are the preferential cleavage sites and do not include all cleavage sites recognized by chymotrypsin, trypsin, or pepsin, and furthermore do not include all cleavage sites for all proteases.

An example of a polypeptide engineered to contain an introduced protease cleavage site is NitromobCRW variant Y213L/I215L (SEQ ID NO: 47). This substitution mutation changes a motif from "YNAYLIG" to "YNALLL". This introduced protease cleavage site may be recognized by pepsin and/or chymotrypsin, and is not present in the wild type NitromobCRW protein sequence. In some embodiments, the introduced protease cleavage site may be at or near the site of the mutation, for example residues 190-230 of the polypeptide. The NitromobCRW variant Y213L/I215L may have an altered or less stable tertiary structure compared to wild-type NitromobCRW. In some embodiments, the introduced protease cleavage site may be located distal from the introduced mutation. For example, the introduced mutation of Y213 and/or I215 may "loosen" the three dimensional folding of the NitromobCRW polypeptide, thereby making a protease cleavage site that was previously inaccessible (and therefore not cleaved) accessible to a protease. This results in the introduced mutation introducing a protease cleavage site that did not exist in the unaltered polypeptide. In some embodiments, the introduced mutation and/or the introduced protease cleavage site is located between amino acid residues 1 to 300 of any one of SEQ ID NOs: 39 to 74. In some embodiments, the introduced mutation and/or the introduced protease cleavage site is located between amino acid residues 97 to 300 of any one of SEQ ID NOs: 39 to 74. In further embodiments, the introduced mutation and/or the introduced protease cleavage site is located between amino acid residues 97 to 266 of any one of SEQ ID NOs: 39 to 74. In further embodiments, the introduced mutation and/or the introduced protease cleavage site is located between amino acid residues 175 to 266 of any one of SEQ ID NOs: 39 to 74. In further embodiments, the introduced mutation and/or the introduced protease cleavage site is located between amino acid residues 185 to 250 of any one of SEQ ID NOs: 40 to 74. In further embodiments, the introduced mutation and/or the introduced protease cleavage site is located between amino acid residues 200 to 230 of any one of SEQ ID NOs: 40 to 74.

The present invention also encompasses a polypeptide comprising an amino acid sequence at least 45% identical, at least 50% identical, at least 55%, at least 60%, at least 65%, at least 70%, at least 75%, at least 80%, at least 85%, at least 90%, at least 92%, at least 95%, at least 98%, at least 99% identical, or is 100% identical to any one of SEQ ID NOs: 39 to 74, and further comprising an introduced mutation which improves digestibility in an SGF assay compared to a polypeptide comprising the amino acid sequence of SEQ ID NO: 39. The mutation may be a substitution mutation, insertion, or deletion. The mutation may be the insertion of at least one leucine residue.

The present invention also includes a method of improving digestibility of a polypeptide at least 45% identical, at least 50% identical, at least 55%, at least 60%, at least 65%, at least 70%, at least 75%, at least 80%, at least 85%, at least 90%, at least 92%, at least 95%, at least 98%, at least 99% identical, or is 100% identical to any one of SEQ ID NOs: 39 to 74 comprising introducing at least one mutation into the amino acid sequence of the polypeptide. In embodiments, this introduced mutation improves the digestibility of the polypeptide in an SGF assay. The mutation may improve digestibility by introducing a protease cleavage site. In other embodiments, the mutation may improve digestibility by altering protease specificity at that site. For example, so that what may have been a chymotrypsin or trypsin site is mutated to a pepsin site. In other embodiments, the mutation may destabilize the protein so that a site is made accessible to a protease for cleavage. The site made accessible to a protease may be distal from the introduced mutation. In preferred embodiments, the mutation does not alter or does not significantly alter the activity, or the insecticidal activity, of the polypeptide. In some embodiments, the polypeptide with the introduced mutation possesses at least 50%, at least 55%, at least 60%, at least 65%, at least 70%, at least 75%, at least 80%, at least 85%, at least 90%, at least 92%, at least 93%, at least 94%, at least 95%, at least 96%, at least 97%, at least 98%, or at least 99% of the insecticidal activity of NitromobCRW. This method is exemplified in the examples of the present specification, where, for example, the NitromobCRW variant Y213L/I215L was found to have improved digestibility in the SGF assay. It also retained very high insecticidal activity.

In some embodiments of the method described above, the introduced mutation(s) may be located between amino acid residues 1 to 300 of any one of SEQ ID NOs: 39 to 74. In further embodiments, the introduced mutation(s) may be located between amino acid residues 97 to 300 of any one of SEQ ID NOs: 39 to 74. In further embodiments, the introduced mutation(s) may be located between amino acid residues 97 to 266 of any one of SEQ ID NOs: 39 to 74. In further embodiments, the introduced mutation(s) may be located between amino acid residues 175 to 266 of any one of SEQ ID NOs: 39 to 74. In further embodiments, the introduced mutation(s) may be located between amino acid residues 185 to 250 of any one of SEQ ID NOs: 39 to 74. In further embodiments, the introduced mutation(s) may be located between amino acid residues 200 to 230 of any one of SEQ ID NOs: 39 to 74.

In other embodiments, a mutation may be introduced at or proximal to Y213 and/or I215 of SEQ ID NO: 39. In further embodiments, the mutation may be Y213L/I215L. In other embodiments, the mutation may be the insertion or deletion of an amino acid residue, such as for example, the insertion of at least one leucine residue. This residue(s) may be adjacent to, or neighboring, Y213 and/or I215 of SEQ ID NO: 39, such as for example NitromobCRW variants L214-Leu-I215 (SEQ ID NO: 57) or I215-Leu-G216 (SEQ ID NO: 58). Leucine residues may also be inserted proximal to Y213 and/or I215, wherein "proximal" may be at least 1, at least 2, at least 4, at least 6, at least 8, at least 10, or at least 20 amino acids away from Y213 and/or 1215.

The insecticidal proteins of the present invention have insect control activity when tested against insect pests in bioassays. In one embodiment, the insecticidal proteins of the invention are active against Coleopteran and/or Lepidopteran insects. A person skilled in the art will appreciate that a protein of the present invention may have a different range of insecticidal activity compared to other proteins of the invention. In some embodiments, a NitromobCRW mutant variant may have insecticidal activity on a broader range of insect pests, such as more Coleopteran or Lepidopteran species, compared to other variants of NitromobCRW. In other embodiments, a variant of NitromobCRW may have insecticidal activity on Lepidopteran species but not on Coleopteran species. In some embodiments, a variant of NitromobCRW may have activity on a broader range of insecticidal activity on Coleopteran or Lepidopteran species compared to unmodified NitromobCRW (SEQ ID NO: 39).

Insects in the order Lepidoptera include without limitation any insect now known or later identified that is classified as a Lepidopteran, including those insect species within suborders Zeugloptera, Glossata, and Heterobathmiina, and any combination thereof. Exemplary Lepidopteran insects include, but are not limited to, *Ostrinia* spp. such as *O. nubilalis* (European corn borer); *Plutella* spp. such as *P. xylostella* (diamondback moth); *Spodoptera* spp. such as *S. frugiperda* (fall armyworm), *S. ornithogalli* (yellowstriped armyworm), *S. praefica* (western yellowstriped armyworm), *S. eridania* (southern armyworm) and *S. exigua* (beet armyworm); *Agrotis* spp. such as *A. ipsilon* (black cutworm), *A. segetum* (common cutworm), *A. gladiaria* (claybacked cutworm), and *A. orthogonia* (pale western cutworm); *Striacosta* spp. such as *S. albicosta* (western bean cutworm); *Helicoverpa* spp. such as *H. zea* (corn earworm), *H. punctigera* (native budworm), *S. littoralis* (Egyptian cotton leafworm) and *H. armigera* (cotton bollworm); *Heliothis* spp. such as *H. virescens* (tobacco budworm); *Diatraea* spp. such as *D. grandiosella* (southwestern corn borer) and *D. saccharalis* (sugarcane borer); *Trichoplusia* spp. such as *T. ni* (cabbage looper); *Sesamia* spp. such as *S. nonagroides* (Mediterranean corn borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Crymodes* spp. such as *C. devastator* (glassy cutworm); *Feltia* spp. such as *F. ducens* (dingy cutworm); and any combination of the foregoing. In one aspect of this embodiment, the insecticidal proteins of the invention are active against black cutworm, sugar cane borer, and/or southwestern corn borer.

Insects in the order Coleoptera include but are not limited to any Coleopteran insect now known or later identified including those in suborders Archostemata, Myxophaga, Adephaga and *Polyphaga*, and any combination thereof.

In one aspect of this embodiment, the insecticidal proteins of the invention are active against *Diabrotica* spp. *Diabrotica* is a genus of beetles of the order Coleoptera commonly referred to as "corn rootworms" or "cucumber beetles." Exemplary *Diabrotica* species include without limitation *Diabrotica barberi* (northern corn rootworm), *D. virgifera virgifera* (western corn rootworm), *D. undecimpunctata howardii* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle), *D. virgifera zeae* (Mexican corn rootworm), *D. beniensis, D. cristata, D. curviplustalata, D. dissimilis, D. elegantula, D. emorsitans, D. graminea, D. hispanloe, D. lemniscata, D. linsleyi, D. milleri, D. nummularis, D. occlusal, D. porrecea, D. scutellata, D. tibialis, D. trifasciata* and *D. viridula*; and any combination thereof.

Other nonlimiting examples of Coleopteran insect pests according to the present invention include *Leptinotarsa* spp. such as *L. decemlineata* (Colorado potato beetle); *Chrysomela* spp. such as *C. scripta* (cottonwood leaf beetle); *Hypothenemus* spp. such as *H. hampei* (coffee berry borer); *Sitophilus* spp. such as *S. zeamais* (maize weevil); *Epitrix* spp. such as *E. hirtipennis* (tobacco flea beetle) and *E. cucumeris* (potato flea beetle); *Phyllotreta* spp. such as *P. cruciferae* (crucifer flea beetle) and *P. pusilla* (western black flea beetle); *Anthonomus* spp. such as *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); and any combination of the foregoing.

The insecticidal proteins of the invention may also be active against Hemipteran, Dipteran, *Lygus* spp., and/or other piercing and sucking insects, for example of the order Orthoptera or Thysanoptera. Insects in the order Diptera include but are not limited to any dipteran insect now known or later identified including but not limited to *Liriomyza* spp. such as *L. trifolii* (leafminer) and *L. sativae* (vegetable leafminer); *Scrobipalpula* spp. such as *S. absoluta* (tomato leafminer); *Delia* spp. such as *D. platura* (seedcorn maggot), *D. brassicae* (cabbage maggot) and *D. radicum* (cabbage root fly); *Psilia* spp. such as *P. rosae* (carrot rust fly); *Tetanops* spp. such as *T. myopaeformis* (sugarbeet root maggot); and any combination of the foregoing.

Insects in the order Orthoptera include but are not limited to any orthopteran insect now known or later identified including but not limited to *Melanoplus* spp. such as *M. differentialis* (Differential grasshopper), *M. femurrubrum* (Redlegged grasshopper), *M. bivittatus* (Twostriped grasshopper); and any combination thereof.

Insects in the order Thysanoptera include but are not limited to any thysanopteran insect now known or later identified including but not limited to *Frankliniella* spp. such as *F. occidentalis* (western flower thrips) and *F. fusca*

(tobacco thrips); and *Thrips* spp. such as *T. tabaci* (onion thrips), *T. palmi* (melon *thrips*); and any combination of the foregoing.

The insecticidal proteins of the invention may also be active against nematodes. The term "nematode" as used herein encompasses any organism that is now known or later identified that is classified in the animal kingdom, phylum Nematoda, including without limitation nematodes within class Adenophorea (including for example, orders Enoplida, Isolaimida, Mononchida, Dorylaimida, Trichocephalida, Mermithida, Muspiceida, Araeolaimida, Chromadorida, Desmoscolecida, Desmodorida and Monhysterida) and/or class Secernentea (including, for example, orders Rhabdita, Strongylida, Ascaridida, Spirurida, Camallanida, Diplogasterida, Tylenchida and Aphelenchida).

Nematodes include but are not limited to parasitic nematodes such as root-knot nematodes, cyst nematodes and/or lesion nematodes. Exemplary genera of nematodes according to the present invention include but are not limited to, *Meloidogyne* (root-knot nematodes), *Heterodera* (cyst nematodes), *Globodera* (cyst nematodes), *Radopholus* (burrowing nematodes), *Rotylenchulus* (reniform nematodes), *Pratylenchus* (lesion nematodes), *Aphelenchoides* (foliar nematodes), *Helicotylenchus* (spiral nematodes), *Hoplolaimus* (lance nematodes), *Paratrichodorus* (stubby-root nematodes), *Longidorus, Nacobbus* (false root-knot nematodes), *Subanguina, Belonlaimus* (sting nematodes), *Criconemella, Criconemoides* (ring nematodes), *Ditylenchus, Dolichodorus, Hemicriconemoides, Hemicycliophora, Hirschmaniella, Hypsoperine, Macroposthonia, Melinius, Punctodera, Quinisulcius, Scutellonema, Xiphinema* (dagger nematodes), *Tylenchorhynchus* (stunt nematodes), *Tylenchulus, Bursaphelenchus* (round worms), and any combination thereof.

Exemplary plant parasitic nematodes according to the present invention include, but are not limited to, *Belonolaimus gracilis, Belonolaimus longicaudatus, Bursaphelenchus xylophilus* (pine wood nematode), *Criconemoides ornata, Ditylenchus destructor* (potato rot nematode), *Ditylenchus dipsaci* (stem and bulb nematode), *Globodera pallida* (potato cyst nematode), *Globodera rostochiensis* (golden nematode), *Heterodera glycines* (soybean cyst nematode), *Heterodera schachtii* (sugar beet cyst nematode); *Heterodera zeae* (corn cyst nematode), *Heterodera avenae* (cereal cyst nematode), *Heterodera carotae, Heterodera trifolii, Hoplolaimus columbus, Hoplolaimus galeatus, Hoplolaimus magnistylus, Longidorus breviannulatus, Meloidogyne arenaria, Meloidogyne chitwoodi, Meloidogyne hapla, Meloidogyne incognita, Meloidogyne javanica, Mesocriconema xenoplax, Nacobbus aberrans, Naccobus dorsalis, Paratrichodorus christiei, Paratrichodorus minor, Pratylenchus brachyurus, Pratylenchus crenatus, Pratylenchus hexincisus, Pratylenchus neglectus, Pratylenchus penetrans, Pratylenchus projectus, Pratylenchus scribneri, Pratylenchus tenuicaudatus, Pratylenchus thornei, Pratylenchus zeae, Punctodera chaccoensis, Quinisulcius acutus, Radopholus similis, Rotylenchulus reniformis, Tylenchorhynchus dubius, Tylenchulus semipenetrans* (citrus nematode), *Siphinema americanum*, X. *Mediterraneum*, and any combination of the foregoing.

In another embodiment, the invention encompasses a method of producing a insecticidal protein that is active against insects, comprising: (a) obtaining a host cell comprising a gene, which itself comprises an expression cassette and/or a nucleic acid molecule of the invention; and (b) growing the transgenic host cell in such a manner to express an insecticidal protein that is active against insects.

In yet a further embodiment, the invention encompasses a method of controlling insects, comprising delivering to the insects an effective insect-controlling amount of an insecticidal protein of the invention.

In one embodiment, at least one of the insecticidal proteins of the invention is expressed in a higher organism such as a plant. In this case, transgenic plants expressing effective insect-controlling amounts of the insecticidal protein protect themselves from insect pests. When the insect starts feeding on such a transgenic plant, it also ingests the expressed insecticidal protein. This will deter the insect from further biting into the plant tissue and/or may even harm or kill the insect. A nucleic acid of the present invention is inserted into an expression cassette, which may then be stably integrated in the genome of the plant. In another embodiment, the nucleic acid is included in a non-pathogenic self-replicating virus. Plants transformed in accordance with the present invention may be monocotyledonous or dicotyledonous and include, but are not limited to, corn, wheat, oat, turfgrass, pasture grass, flax, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

In another embodiment, the invention encompasses a method of producing a plant or plant part having enhanced insect resistance as compared to a control plant or plant part, comprising: (a) introducing a nucleic acid molecule comprising an expression cassette of the invention; and (b) growing the plant part into a plant that expresses the heterologous nucleic acid molecule of the expression cassette and that has enhanced insect resistance as compared to a control plant or plant part that has not been transformed with a nucleic acid molecule comprising the expression cassette. In a preferred embodiment, the expression cassette may encode a polypeptide comprising an amino acid sequence that is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical or similar to SEQ ID NOs: 39 to 74. In a preferred embodiment, the expression cassette may encode a polypeptide comprising an amino acid sequence that is at least 60% identical to SEQ ID NO: 47. "Enhanced" insect resistance may be measured as an increase in insecticidal activity. Enhanced insect resistance may be greater than 0%, at least 1%, at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, at least 100%, at least 125%, at least 150%, at least 200%, at least 300%, at least 400%, at least 500%, at least 600%, at least 700%, at least 800%, at least 900%, or at least 1000% greater insecticidal activity compared to a control plant. A plant or plant part having enhance insect resistance as compared to a control plant or plant part may be produced by methods of plant transformation, plant tissue culture, or breeding. The plant or plant part may be produced by methods of sexual or asexual propagation. Any suitable control plant or plant part can be used, for example a plant of the same or similar genetic background grown in the same environment. In embodiments, the control plant or plant part is of the same genetic background and is growing in the same environment as the described plant, but it does not comprise a molecule of the invention, while the described plant does comprise a molecule of the invention.

In another embodiment, the invention encompasses a method of enhancing insect resistance in a plant or plant part as compared to a control plant or plant part, comprising expressing in the plant or plant part a nucleic acid molecule or an expression cassette of the invention, wherein expression of the heterologous nucleic acid of the expression cassette results in enhanced insect resistance in a plant or plant part as compared to a control plant or plant part. In embodiments, the expression cassette or nucleic acid molecule comprises a promoter operably linked to a heterologous nucleic acid molecule comprising a nucleotide sequence that comprises: (a) a nucleotide sequence of any one of SEQ ID NOs: 1 to 38; (b) a nucleotide sequence that is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of any one of SEQ ID NOs: 1 to 38; (c) a nucleotide sequence that encodes a polypeptide, wherein the amino acid sequence of the polypeptide comprises SEQ ID NOs: 39 to 74, and has insect control activity; (d) a nucleotide sequence that encodes a polypeptide, wherein the amino acid sequence of the polypeptide is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the amino acid sequence of SEQ ID NOs: 39 to 74; or (e) a nucleotide sequence that is complementary to the nucleotide sequence of any one of (a) to (d) above. The nucleic acid molecule or expression cassette may be introduced into the plant. In some embodiments, the nucleic acid molecule or expression cassette may be introduced into a plant part and a plant comprising the nucleic acid molecule or expression cassette may be produced from the plant part.

In another embodiment, the invention encompasses a method of producing a plant having enhanced insect resistance as compared to a control plant, comprising detecting, in a plant part, a heterologous nucleic acid comprising a nucleic acid molecule or an expression cassette of the invention and producing a plant from the plant part, thereby producing a plant having enhanced insect resistance as compared to a control plant. In a further embodiment, the invention encompasses a method of identifying a plant or plant part having enhanced insect resistance as compared to a control plant or plant part, comprising detecting, in the plant or plant part, a nucleic acid molecule or an expression cassette of the invention, thereby identifying a plant or plant part having enhanced insect resistance. In a further embodiment, the expression cassette or a diagnostic fragment thereof is detected in an amplification product from a nucleic acid sample from the plant or plant part. The diagnostic fragment may be a nucleic acid molecule at least 10 contiguous nucleotides long which is unique to the expression cassette of the invention.

In yet another embodiment, the invention encompasses a method of producing a plant having enhanced insect resistance as compared to a control plant or plant part, comprising crossing a first parent plant with a second parent plant, wherein at least the first parent plant comprises within its genome a heterologous nucleic acid that comprises a nucleic acid molecule or an expression cassette of the invention and producing a progeny generation, wherein the progeny generation comprises at least one plant that possesses the heterologous nucleic acid within its genome and that exhibits enhanced insect resistance as compared to a control plant.

In preferred embodiments, the methods of the invention confer enhanced insect resistance in a plant or plant part against a Coleopteran and/or a Lepidopteran insect pest. Insect control of Coleopteran insect pests are demonstrated in the Examples. In further embodiments, the methods of the invention confer enhanced insect resistance in a plant or plant part against *Diabrotica* species, including *Diabrotica virgifera virgifera*, *Diabrotica barberi*, *Diabrotica undecimpunctata howardi*, *Diabrotica virgifera zeae*, and/or *Diabrotica speciosa*, and/or related species.

In preferred embodiments, the methods of the invention confer enhanced insect resistance in a monocotyledonous plant.

The present invention further encompasses a transgenic plant comprising a heterologous nucleic acid molecule or an expression cassette of the invention, which when transcribed and translated confers enhanced insect resistance. In preferred embodiments, the heterologous nucleic acid molecule comprises a sequence at least 45%, at least 50%, at least 55%, at least 60%, at least 65%, at least 70%, at least 75%, at least 80%, at least 85%, at least 90%, at least 91% at least 92%, at least 93%, at least 94%, at least 95%, at least 96%, at least 97%, at least 98% at least 99%, or 100% identical to any one of SEQ ID NOs: 1 to 38, or a complement thereof. In a further embodiment, the transgenic plant comprises a heterologous nucleic acid molecule comprising a sequence at least 45%, at least 50%, at least 55%, at least 60%, at least 65%, at least 70%, at least 75%, at least 80%, at least 85%, at least 90%, at least 91% at least 92%, at least 93%, at least 94%, at least 95%, at least 96%, at least 97%, at least 98% at least 99%, or 100% identical to SEQ ID NO: 1 to 38, or a complement thereof. In embodiments, the transgenic plant is a dicotyledonous plant. In preferred embodiments, the transgenic plant is a monocotyledonous plant. In further embodiments, the transgenic plant is alfalfa, aneth, apple, apricot, artichoke, arugula, asparagus, avocado, banana, beans, beet, blackberry, blueberry, broccoli, brussel sprouts, cabbage, canola, cantaloupe, carrot, cassava, cauliflower, celery, cherry, cilantro, citrus, clementine, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sunflower, sweet potato, sweetgum, tangerine, tea, tobacco, tomato, turf, a vine, watermelon, yams, or zucchini. In preferred embodiments, the transgenic plant is millet, switchgrass, maize, sorghum, wheat, oat, turf grass, pasture grass, flax, rice, sugarcane, oilseed rape, or barley.

In yet another embodiment, a transgenic plant of the invention comprises a heterologous nucleic acid molecule comprising a promoter sequence. In yet another embodiment, a transgenic plant of the invention may comprise a heterologous nucleic acid molecule which encodes for at least one additional desired trait. The additional trait may be encoded on the same heterologous nucleic acid molecule as a molecule of the invention, or it may be encoded on a second heterologous nucleic acid molecule. The additional desired trait may confer insect resistance to a second insect pest, insect resistance to the same insect pest, abiotic stress tolerance, male sterility, herbicide resistance, bacterial disease resistance, fungal disease resistance, viral disease resistance, nematode resistance, modified fatty acid metabolism, modified carbohydrate metabolism, improved nutritional value, improved performance in an industrial process or altered reproductive capability. The additional desired trait may also induce production within the plant of a commercially valuable enzyme or metabolite.

In embodiments, the desired added trait is a second pesticidal agent. The second pesticidal agent may be active on any plant pest, including insects, nematodes, fungi, viruses or bacteria. Examples of insect plant pests include and are not limited to *Nilaparvata* spp. (e.g. *N. lugens* (brown planthopper)); *Laodelphax* spp. (e.g. *L. striatellus* (small brown planthopper)); *Nephotettix* spp. (e.g. *N. virescens* or *N. cincticeps* (green leafhopper), or *N. nigropictus* (rice leafhopper)); *Sogatella* spp. (e.g. *S. furcifera* (whitebacked planthopper)); *Blissus* spp. (e.g. *B. leucopterus leucopterus* (chinch bug)); *Scotinophora* spp. (e.g. *S. vermidulate* (rice blackbug)); *Acrosternum* spp. (e.g. *A. hilare* (green stink bug)); *Parnara* spp. (e.g. *P. guttata* (rice skipper)); *Chilo* spp. (e.g. *C. suppressalis* (rice striped stem borer), *C. auricilius* (gold-fringed stem borer), or *C. polychrysus* (dark-headed stem borer); *Chilotraea* spp. (e.g. *C. polychrysa* (rice stalk borer)); *Sesamia* spp. (e.g. *S. inferens* (pink rice borer)); *Tryporyza* spp. (e.g. *T. innotata* (white rice borer), or *T. incertulas* (yellow rice borer)); *Cnaphalocrocis* spp. (e.g. *C. medinalis* (rice leafroller)); *Agromyza* spp. (e.g. *A. oryzae* (leafminer), or *A. parvicornis* (corn blot leafminer)); *Diatraea* spp. (e.g. *D. saccharalis* (sugarcane borer), or *D. grandiosella* (southwestern corn borer)); *Narnaga* spp. (e.g. *N. aenescens* (green rice caterpillar)); *Xanthodes* spp. (e.g. *X. transversa* (green caterpillar)); *Spodoptera* spp. (e.g. *S. frugiperda* (fall armyworm), *S. exigua* (beet armyworm), *S. littoralis* (climbing cutworm) or *S. praefica* (western yellowstriped armyworm)); *Mythimna* spp. (e.g. Mythmna (Pseudaletia) seperata (armyworm)); *Helicoverpa* spp. (e.g. *H. zea* (corn earworm)); *Colaspis* spp. (e.g. *C. brunnea* (grape colaspis)); *Lissorhoptrus* spp. (e.g. *L. oryzophilus* (rice water weevil)); *Echinocnemus* spp. (e.g. *E. squamos* (rice plant weevil)); *Diclodispa* spp. (e.g. *D. armigera* (rice hispa)); *Oulema* spp. (e.g. *O. oryzae* (leaf beetle); *Sitophilus* spp. (e.g. *S. oryzae* (rice weevil)); *Pachydiplosis* spp. (e.g. *P. oryzae* (rice gall midge)); *Hydrellia* spp. (e.g. *H. griseola* (small rice leafminer), or *H. sasakii* (rice stem maggot)); *Chlorops* spp. (e.g. *C. oryzae* (stem maggot)); *Diabrotica* spp. (e.g. *D. virgifera virgifera* (western corn rootworm), *D. barberi* (northern corn rootworm), *D. undecimpunctata howardi* (southern corn rootworm), *D. virgifera zeae* (Mexican corn rootworm); *D. balteata* (banded cucumber beetle)); *Ostrinia* spp. (e.g. *O. nubilalis* (European corn borer)); *Agrotis* spp. (e.g. *A. ipsilon* (black cutworm)); *Elasmopalpus* spp. (e.g. *E. lignosellus* (lesser cornstalk borer)); *Melanotus* spp. (wireworms); *Cyclocephala* spp. (e.g. *C. borealis* (northern masked chafer), or *C. immaculata* (southern masked chafer)); *Popillia* spp. (e.g. *P. japonica* (Japanese beetle)); *Chaetocnema* spp. (e.g. *C. pulicaria* (corn flea beetle)); *Sphenophorus* spp. (e.g. *S. maidis* (maize billbug)); *Rhopalosiphum* spp. (e.g. *R. maidis* (corn leaf aphid)); *Anuraphis* spp. (e.g. *A. maidiradicis* (corn root aphid)); *Melanoplus* spp. (e.g. *M. femurrubrum* (redlegged grasshopper) *M. differentialis* (differential grasshopper) or *M. sanguinipes* (migratory grasshopper)); *Hylemya* spp. (e.g. *H. platura* (seedcorn maggot)); *Anaphothrips* spp. (e.g. *A. obscrurus* (grass thrips)); *Solenopsis* spp. (e.g. *S. milesta* (thief ant)); or spp. (e.g. *T. urticae* (twospotted spider mite), *T. cinnabarinus* (carmine spider mite); *Helicoverpa* spp. (e.g. *H. zea* (cotton bollworm), or *H. armigera* (American bollworm)); *Pectinophora* spp. (e.g. *P. gossypiella* (pink bollworm)); *Earias* spp. (e.g. *E. vittella* (spotted bollworm)); *Heliothis* spp. (e.g. *H. virescens* (tobacco budworm)); *Anthonomus* spp. (e.g. *A. grandis* (boll weevil)); *Pseudatomoscelis* spp. (e.g. *P. seriatus* (cotton fleahopper)); *Trialeurodes* spp. (e.g. *T. abutiloneus* (banded-winged whitefly) *T. vaporariorum* (greenhouse whitefly)); *Bemisia* spp. (e.g. *B. argentifolii* (silverleaf whitefly)); *Aphis* spp. (e.g. *A. gossypii* (cotton aphid)); *Lygus* spp. (e.g. *L. lineolaris* (tarnished plant bug) or *L. hesperus* (western tarnished plant bug)); *Euschistus* spp. (e.g. *E. conspersus* (consperse stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion thrips)); *Frankliniella* spp. (e.g. *F. fusca* (tobacco thrips), or *F. occidentalis* (western flower thrips)); *Leptinotarsa* spp. (e.g. *L. decemlineata* (Colorado potato beetle), *L. juncta* (false potato beetle), or *L. texana* (Texan false potato beetle)); *Lema* spp. (e.g. *L. trilineata* (threelined potato beetle)); *Epitrix* spp. (e.g. *E. cucumeris* (potato flea beetle), *E. hirtipennis* (flea beetle), or *E. tuberis* (tuber flea beetle)); *Epicauta* spp. (e.g. *E. vittata* (striped blister beetle)); *Phaedon* spp. (e.g. *P. cochleariae* (mustard leaf beetle)); *Epilachna* spp. (e.g. *E. varivetis* (mexican bean beetle)); *Acheta* spp. (e.g. *A. domesticus* (house cricket)); *Empoasca* spp. (e.g. *E. fabae* (potato leafhopper)); *Myzus* spp. (e.g. *M. persicae* (green peach aphid)); Paratrioza spp. (e.g. *P. cockerelli* (psyllid)); *Conoderus* spp. (e.g. *C. falli* (southern potato wireworm), or *C. vespertinus* (tobacco wireworm)); *Phthorimaea* spp. (e.g. *P. operculella* (potato tuberworm)); *Macrosiphum* spp. (e.g. *M. euphorbiae* (potato aphid)); *Thyanta* spp. (e.g. *T. pallidovirens* (redshouldered stinkbug)); *Phthorimaea* spp. (e.g. *P. operculella* (potato tuberworm)); *Helicoverpa* spp. (e.g. *H. zea* (tomato fruitworm); *Keiferia* spp. (e.g. *K. lycopersicella* (tomato pinworm)); *Limonius* spp. (wireworms); Manduca spp. (e.g. *M. sexta* (tobacco hornworm), or *M. quinquemaculata* (tomato hornworm)); *Liriomyza* spp. (e.g. *L. sativae, L. trifolli* or *L. huidobrensis* (leafminer)); *Drosophilla* spp. (e.g. *D. melanogaster, D. yakuba, D. pseudoobscura* or *D. simulans*); *Carabus* spp. (e.g. *C. granulatus*); *Chironomus* spp. (e.g. *C. tentanus*); *Ctenocephalides* spp. (e.g. *C. felis* (cat flea)); *Diaprepes* spp. (e.g. *D. abbreviatus* (root weevil)); *Ips* spp. (e.g. *I. pini* (pine engraver)); *Tribolium* spp. (e.g. *T. castaneum* (red floor beetle)); *Glossina* spp. (e.g. *G. morsitans* (tsetse fly)); *Anopheles* spp. (e.g. *A. gambiae* (malaria mosquito)); *Helicoverpa* spp. (e.g. *H. annigera* (African Bollworm)); *Acyrthosiphon* spp. (e.g. *A. pisum* (pea aphid)); *Apis* spp. (e.g. *A. melifera* (honey bee)); *Homalodisca* spp. (e.g. *H. coagulate* (glassy-winged sharpshooter)); *Aedes* spp. (e.g. *Ae. aegypti* (yellow fever mosquito)); *Bombyx* spp. (e.g. *B. mori* (silkworm)); *Locusta* spp. (e.g. *L. migratoria* (migratory locust)); *Boophilus* spp. (e.g. *B. microplus* (cattle tick)); *Acanthoscurria* spp. (e.g. *A. gomesiana* (red-haired chololate bird eater)); *Diploptera* spp. (e.g. *D. punctata* (pacific beetle cockroach)); *Heliconius* spp. (e.g. *H. erato* (red passion flower butterfly) or *H. melpomene* (postman butterfly)); *Curculio* spp. (e.g. *C. glandium* (acorn weevil)); *Plutella* spp. (e.g. *P. xylostella* (diamondback moth)); *Amblyomma* spp. (e.g. *A. variegatum* (cattle tick)); *Anteraea* spp. (e.g. *A. yamamai* (silkmoth)); and *Armigeres* spp. (e.g. *A. subalbatus*).

The insecticidal proteins of the invention can be used in combination with other pesticidal agents (e.g. Bt Cry proteins) to increase pest target range. Furthermore, the use of the insecticidal proteins of the invention in combination with an insecticidal agent which has a different mode of action or target a different receptor in the insect gut has particular utility for the prevention and/or management of insect resistance.

The second pesticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry 6 protein, a Cry7 protein, a Cry8 protein, a Cry9 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP (Vegetative Insecticidal Protein, disclosed in U.S. Pat. Nos. 5,849,870 and 5,877,012, herein incorporated by reference), a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A (U.S. Pat. No. 7,276,583, incorporated by reference herein), eCry3.1Ab (U.S. Pat. No. 8,309,516, incorporated by reference herein), and Vip3A proteins, including Vip3Aa (U.S. Pat. No. 6,137,033, incorporated by reference herein).

In other embodiments, a transgenic plant of the invention may comprise a second pesticidal agent which may be derived from sources other than *B. thuringiensis*. The second insecticidal agent can be an agent selected from the group comprising an a amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin. In other embodiments, the second agent may be at least one insecticidal protein derived from an insecticidal toxin complex (Tc) from *Photorhabdus, Xenorhabus, Serratia*, or *Yersinia*. In other embodiments. The insecticidal protein may be an ADP-ribosyltransferase derived from an insecticidal bacteria, such as *Photorhabdus* ssp. In still other embodiments, the insecticidal protein may Axmi205 or derived from Axmi205 (U.S. Pat. Nos. 8,575, 425 and 9,394,345, each incorporated herein by reference). In other embodiments, the insecticidal protein may be a VIP protein, such as VIP1 and/or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In other embodiments, in the insecticidal protein may be a LachbCRW (PCT Application No. PCT/US2017/ 045,256), a HmassCRW (PCT Application No. PCT/ US2017/058,179), or a WoodsCRW (PCT Application No. PCT/US2018/012,730) protein or protein variant. hi still other embodiments, the insecticidal protein may be engineered or may be a hybrid or chimera of any of the preceding insecticidal proteins.

In some embodiments, the transgenic plant of the invention may comprise and/or express at least a second pesticidal agent which is non-proteinaceous. In some embodiments, the second pesticidal agent may be present on the surface of the plant, for example as a topical application. In preferred embodiments, the second pesticidal agent is an interfering RNA molecule. An interfering RNA typically comprises at least a RNA fragment against a target gene, a spacer sequence, and a second RNA fragment which is complementary to the first, so that a double-stranded RNA structure can be formed. RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Interfering RNAs are known in the art to be useful for insect control (see, for example, publication WO2013/192256, incorporated by reference herein). An interfering RNA designed for use in insect control produces a non-naturally occurring double-stranded RNA, which takes advantage of the native RNAi pathways in the insect to trigger down-regulation of target genes that may lead to the cessation of feeding and/or growth and may result in the death of the insect pest. The interfering RNA molecule may confer insect resistance against the same target pest as the protein of the invention, or may target a different pest. The targeted insect plant pest may feed by chewing, sucking, or piercing. Interfering RNAs are known in the art to be useful for insect control. In embodiments, the dsRNA useful for insect control is described in WO Publication Nos. WO2018/026770, WO2018/026773, and WO2018/026774, herein incorporated by reference. In embodiments, the dsRNA useful for insect control is described in U.S. Pat. Nos. 9,238,823, 9,340,797, or 8,946,510, herein incorporated by reference. In embodiments, the dsRNA useful for insect control is described in U.S. patent application Ser. Nos. 12/868,994, 13/831,230, 14/207,313, or 14/207,318, herein incorporated by reference. In other embodiments, the interfering RNA may confer resistance against a non-insect plant pest, such as a nematode pest or a virus pest.

The co-expression of more than one pesticidal agent in the same transgenic plant can be achieved by making a single recombinant vector comprising coding sequences of more than one pesticidal agent in a so called molecular stack and genetically engineering a plant to contain and express all the pesticidal agents in the transgenic plant. Such molecular stacks may be also be made by using mini-chromosomes as described, for example in U.S. Pat. No. 7,235,716. Alternatively, a transgenic plant comprising one nucleic acid encoding a first pesticidal agent can be re-transformed with a different nucleic acid encoding a second pesticidal agent and so forth. Alternatively, a plant, Parent 1, can be genetically engineered for the expression of genes of the present invention. A second plant, Parent 2, can be genetically engineered for the expression of a second pesticidal agent. By crossing Parent 1 with Parent 2, progeny plants are obtained which express all the genes introduced into Parents 1 and 2.

Transgenic plants or seed comprising and/or expressing an insecticidal protein of the invention can also be treated with an insecticide or insecticidal seed coating as described in U.S. Pat. Nos. 5,849,320 and 5,876,739, herein incorporated by reference. In embodiments, where both the insecticide or insecticidal seed coating and the transgenic plant or seed of the invention are active against the same target insect, for example a Coleopteran pest or a *Diabrotica* target pest, the combination is useful (i) in a method for further enhancing activity of the composition of the invention against the target insect, and/or (ii) in a method for preventing development of resistance to the composition of the invention by providing yet another mechanism of action against the target insect. Thus, in embodiments, the invention provides a method of enhancing control of a *Diabrotica* insect population comprising providing a transgenic plant or seed of the invention and applying to the plant or the seed an insecticide or insecticidal seed coating to a transgenic plant or seed of the invention.

Even where the insecticide or insecticidal seed coating is active against a different insect, the insecticide or insecticidal seed coating is useful to expand the range of insect control, for example by adding an insecticide or insecticidal seed coating that has activity against Lepidopteran insects to a transgenic seed of the invention, which, in some embodiments, has activity against Coleopteran and some Lepidopteran insects, the coated transgenic seed produced controls both Lepidopteran and Coleopteran insect pests.

Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan® (carbofuran), Lanate® (methomyl, metomil, mesomile), Sevin® (carbaryl), Talstar® (bifenthrin), Force® (tefluthrin), Ammo® (cypermethrin), Cymbush® (cypermethrin), Delta Gold® (deltamethrin), Karate® (lambda-cyhalothrin), Ambush® (permethrin), Pounce® (permethrin), Brigade® (bifenthrin), Capture® (bifenthrin), ProShield® (tefluthrin), Warrior® (lambda-cyhalothrin), Dursban® (chlorphyrifos), Fortress® (chlorethoxyfos), Mocap® (ethoprop), Thimet® (phorate), AAstar® (phorate, flucythinate), Rampart® (phorate), Counter® (terbufos), Cygon® (dimethoate), Dicapthon, Regent® (fipronil), Cruiser® (thiamethoxam), Gaucho® (imidacloprid), Prescribe® (imidacloprid), Poncho® (clothianidin) and Aztec® (cyfluthrin, tebupirimphos).

The present invention also encompasses a composition comprising an effective insect-controlling amount of an insecticidal protein according to the invention. In further embodiments, the composition comprises a suitable agricultural carrier and a polypeptide of the invention with insecticidal activity. The agricultural carrier may include adjuvants, mixers, enhancers, etc. beneficial for application of an active ingredient, such as a polypeptide of the invention, including a polypeptide comprising an amino acid sequence that is at least 60%, at least 65%, at least 70%, at least 75%, at least 80%, at least 85%, at least 90%, at least 95%, or 100% identical to of any of SEQ ID NOs: 39 to 74. Suitable carriers should not be phytotoxic to valuable crops, particularly at the concentrations employed in applying the compositions in the presence of crops, and should not react chemically with the compounds of the active ingredient herein, namely a polypeptide of the invention, or other composition ingredients. Such mixtures can be designed for application directly to crops, or can be concentrates or formulations which are normally diluted with additional carriers and adjuvants before application. They may include inert or active components and can be solids, such as, for example, dusts, powders, granules, water dispersible granules, or wettable powders, or liquids, such as, for example, emulsifiable concentrates, solutions, emulsions or suspensions. Suitable agricultural carriers may include liquid carriers, for example water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers may include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like. In another embodiment, a polypeptide of the invention may be encapsulated in a synthetic matrix such as a polymer and applied to the surface of a host such as a plant. Ingestion of the host cells by an insect permits delivery of the insect control agents to the insect and results in a toxic effect in the insect pest.

In further embodiments, a composition of the invention may be a powder, dust, pellet, granule, spray, emulsion, colloid, or solution. A composition of the invention may be prepared by desiccation, lyophilization, homogenization, extraction, filtration, centrifugation, sedimentation, or concentration of a culture of bacterial cells. A composition of the invention may comprise at least 1%, at least 5%, at least 10%, at least 20%, at least 25%, at least 30%, at least 35%, at least 40%, at least 50%, at least 60%, at least 70%, at least 80%, at least 90%, at least 95%, at least 97%, or at least 99% by weight a polypeptide of the invention.

In embodiments, a composition of the invention may comprise at least a second pesticidal agent (e.g., which may be expressed transgenically from the plant and/or be incorporated into the composition), which may be insecticidal, nematicidal, fungicidal, or bactericidal. At least a second pesticidal agent may be insecticidal to the same insect as a polypeptide of the invention or to a different insect. The second pesticidal agent may be a polypeptide. The pesticidal agent may be an interfering RNA (e.g., a dsRNA). The second pesticidal agent may be a microorganism, such as a bacteria, which comprises a nucleic acid molecule that encodes for a pesticidal agent and/or contains a pesticidal agent such as a polypeptide or interfering RNA. The microorganism may be attenuated, heat-inactivated, or lyophilized. The microorganism may be dead or unable to reproduce. The second pesticidal agent may be an insecticide, for example carbofuran, carbaryl, methomyl, bifenthrin, tefluthrin, permethrin, cyfluthrin, lambda-cyhalothrin, cypermethrin, deltamethrin, chlorpyrifos, chlorethoxyfos, clothianidin, dimethoate, ethoprophos, malathion, methyl-parathion, phorate, terbufos, tebupirimiphos, fipronil, acetamiprid, imidacloprid, thiacloprid, thiamethoxam, endosulfan, bensultap, or a combination thereof, or a commercial product containing such insecticides and insecticidal seed coatings as described above.

A composition of the invention, for example a composition comprising a polypeptide of the invention and an agriculturally acceptable carrier, may be used in conventional agricultural methods. An agriculturally acceptable carrier is a formulation useful for applying a composition comprising a polypeptide of the invention to a plant or seed. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

The present invention also comprises a method for controlling a Lepidopteran and/or Coleopteran pest population comprising contacting said population with an effective insect-controlling amount of a polypeptide of the invention with insecticidal activity, where the polypeptide is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to SEQ ID NOs: 39 to 74. Contacting includes members of the pest population feeding on or ingesting the polypeptide. The polypeptide may be incorporated into insect diet food or may be expressed in or present on plant tissue which the insect then ingests. In further embodiments, controlling the Lepidopteran and/or Coleopteran pest populations includes killing the insects by contacting the insects with an effective insect-controlling amount of a polypeptide of the invention.

The present invention also comprises a method for protecting a plant from an insect pest, comprising expressing in a plant or plant cell a nucleotide sequence or expression cassette that encodes an insecticidal polypeptide of the invention. In embodiments, the nucleotide sequence is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of SEQ ID NO: 2 to 36 or encodes a polypeptide comprising an amino acid sequence that is at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or is 100% identical to SEQ ID NOs: 39 to 74. In further embodiments, the plant or plant cell produces an insecticidal polypeptide having insecticidal activity against a Lepidopteran and/or Coleopteran pest.

The present invention also comprises a method for increasing yield in a plant comprising growing in a field a plant, or a seed thereof, having stably incorporated into its genome a nucleic acid molecule of an expression cassette of the invention, and wherein said field is infested with a pest against which said polypeptide has insecticidal activity.

Once a desired nucleic acid has been transformed into a particular plant species, it may be propagated in that species or moved into other varieties of the same species, particularly including commercial varieties, using traditional breeding techniques.

In embodiments, a nucleic acid of this invention is expressed in transgenic plants, thus causing the biosynthesis of the corresponding insecticidal protein in the transgenic plants. In this way, transgenic plants with enhanced resistance to insects, particularly corn rootworm, are generated. For their expression in transgenic plants, the nucleic acids of the invention may optionally be modified and optimized. Although in many cases genes from microbial organisms can be expressed in plants at high levels without modification, low expression in transgenic plants may result from microbial nucleic acids having codons that are not preferred in plants. It is known in the art that all organisms have specific preferences for codon usage, and the codons of the nucleic acids described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleic acids that have low GC contents may express poorly in plants due to the existence of ATTTA motifs that may destabilize messages, and AATAAA motifs that may cause inappropriate polyadenylation. In embodiments, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleic acids are screened for the existence of illegitimate splice sites that may cause message truncation. All changes required to be made within the nucleic acids such as those described above can be made using well known techniques of site directed mutagenesis, PCR, and synthetic gene construction, for example, using the methods described in the published patent applications EP 0 385 962, EP 0 359 472, and WO 93/07278.

In one embodiment of the invention a coding sequence for an insecticidal protein of the present invention is made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid might be derived, for example, from known gene sequences from maize. Maize codon usage for 28 genes from maize plants is found in Murray et al., Nucleic Acids Research 17:477-498 (1989), the disclosure of which is incorporated herein by reference.

In this manner, the nucleotide sequences can be optimized for expression in any plant. It is recognized that all or any part of the gene sequence may be optimized or synthetic. That is, synthetic or partially optimized sequences may also be used.

For more efficient initiation of translation, sequences adjacent to the initiating methionine may be modified. For example, they can be modified by the inclusion of sequences known to be effective in plants. Joshi has suggested an appropriate consensus for plants (NAR 15:6643-6653 (1987)) and Clontech suggests a further consensus translation initiator (1993/1994 catalog, page 210). These consensus sequences are suitable for use with the nucleic acids of this invention. In embodiments, the sequences are incorporated into constructions comprising the nucleic acids, up to and including the ATG (whilst leaving the second amino acid unmodified), or alternatively up to and including the GTC subsequent to the ATG (with the possibility of modifying the second amino acid of the transgene).

Expression of the nucleic acids in transgenic plants is driven by promoters that function in plants. The choice of promoter will vary depending on the temporal and spatial requirements for expression, and also depending on the target species. Thus, expression of the nucleic acids of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleic acids in the desired cell.

In one embodiment promoters are used that are expressed constitutively including the actin or ubiquitin or CMP promoters or the CaMV 35S and 19S promoters. The nucleic acids of this invention can also be expressed under the regulation of promoters that are chemically regulated. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

In another embodiment a category of promoters which is wound inducible can be used. Numerous promoters have been described which are expressed at wound sites and also at the sites of phytopathogen infection. Ideally, such a promoter should only be active locally at the sites of infection, and in this way the insecticidal proteins of the invention only accumulate in cells that need to synthesize the proteins to kill the invading insect pest. Preferred promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Tissue-specific or tissue-preferential promoters useful for the expression of genes encoding insecticidal proteins of the invention in plants, particularly corn, are those which direct expression in root, pith, leaf or pollen, particularly root. Such promoters, e.g. those isolated from PEPC or trpA, are disclosed in U.S. Pat. No. 5,625,136, or MTL, disclosed in U.S. Pat. No. 5,466,785. Both U. S. patents are herein incorporated by reference in their entirety.

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In further aspects, the nucleotide sequences of the invention can be operably associated with a promoter that is wound inducible or inducible by pest or pathogen infection (e.g., a insect or nematode plant pest). Numerous promoters have been described which are expressed at wound sites and/or at the sites of pest attack (e.g., insect/nematode feeding) or phytopathogen infection. Ideally, such a promoter should be active only locally at or adjacent to the sites of attack, and in this way expression of the nucleotide sequences of the invention will be focused in the cells that are being invaded or fed upon. Such promoters include, but are not limited to, those described by Stanford et al., Mol. Gen. Genet. 215:200-208 (1989), Xu et al. Plant Molec. Biol. 22:573-588 (1993), Logemann et al. Plant Cell 1:151-158 (1989), Rohrmeier and Lehle, Plant Molec. Biol. 22:783-792 (1993), Firek et al. Plant Molec. Biol. 22:129-142 (1993), Warner et al. Plant J. 3:191-201 (1993), U.S. Pat. Nos. 5,750,386, 5,955,646, 6,262,344, 6,395,963, 6,703,541, 7,078,589, 7,196,247, 7,223,901, and U.S. Patent Application Publication 2010043102.

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

Numerous other sequences can be incorporated into expression cassettes described in this invention. These include sequences that have been shown to enhance expression such as intron sequences (e.g. from Adh1 and bronze1) and viral leader sequences (e.g. from TMV, MCMV and AMV).

It may be preferable to target expression of the nucleic acids of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleic acid. Many such target sequences are known for the chloroplast and their functioning in heterologous constructions has been shown. The expression of the nucleic acids of the present invention is also targeted to the endoplasmic reticulum or to the vacuoles of the host cells. Techniques to achieve this are well known in the art.

Vectors suitable for plant transformation are well-known in the art. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093-1096 (1986)). For both direct gene transfer and Agrobacterium-mediated transfer, transformation is usually (but not necessarily) undertaken with a selectable marker that may provide resistance to an antibiotic (kanamycin, hygromycin or methotrexate) or a herbicide (basta). Plant transformation vectors comprising the nucleic acid molecules of the present invention may also comprise genes (e.g. phosphomannose isomerase; PMI) which provide for positive selection of the transgenic plants as disclosed in U.S. Pat. Nos. 5,767,378 and 5,994,629, herein incorporated by reference. The choice of selectable marker is not, however, critical to the invention.

In embodiments, the nucleic acid can be transformed into the nuclear genome. In another embodiment, a nucleic acid of the present invention is directly transformed into the plastid genome. A major advantage of plastid transformation is that plastids are generally capable of expressing bacterial genes without substantial codon optimization, and plastids are capable of expressing multiple open reading frames under control of a single promoter. Plastid transformation technology is extensively described in U.S. Pat. Nos. 5,451, 513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga Chlamydomonas reinhardtii (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid of the present invention is inserted into a plastid-targeting vector and transformed into the plastid genome of a desired plant host. Plants homoplastic for plastid genomes containing a nucleic acid of the present invention are obtained, and are preferentially capable of high expression of the nucleic acid.

EXAMPLES

The invention will be further described by reference to the following detailed examples. These examples are provided for the purposes of illustration only, and are not intended to be limiting unless otherwise specified. Standard recombinant DNA and molecular cloning techniques used here are well known in the art and are described by J. Sambrook, et al., *Molecular Cloning: A Laboratory Manual*, 3d Ed., Cold Spring Harbor, NY: Cold Spring Harbor Laboratory Press (2001); by T. J. Silhavy, M. L. Berman, and L. W. Enquist, *Experiments with Gene Fusions*, Cold Spring Harbor Laboratory, Cold Spring Harbor, NY (1984) and by Ausubel, F. M. et al., *Current Protocols in Molecular Biology*, New York, John Wiley and Sons Inc., (1988), Reiter, et al., *Methods in Arabidopsis Research*, World Scientific Press (1992), and Schultz et al., *Plant Molecular Biology Manual*, Kluwer Academic Publishers (1998).

Example 1: Identification of a Protein with Insecticidal Activity Against Western Corn Rootworm An insecticidal protein (SEQ ID NO: 39) was identified from *Nitrococcus mobilis*. An *E. coli*-optimized version of this gene was synthesized (SEQ ID NO: 1) and the gene was cloned into a pET29a vector, creating construct p(Nitromob). The p(Nitromob) construct was transformed into *E. coli* BL21*(DE3) and protein expression was carried out in Luria-Bertani broth with IPTG induction at 18° C. overnight. The soluble fraction of lysates was prepared from these cultures by use of a French pressure cell followed by centrifugation of whole lysates at 20,000×g for thirty minutes. The supernatant (soluble fraction) was then tested for bioactivity to Western Corn Rootworm (WCR; *Diabrotica virgifera*).

Bioactivity assays were performed using a diet-incorporation method. Briefly, *E. coli* BL21*(DE3) lysates were mixed with an equal volume of heated artificial insect diet (Bioserv, Inc., Frenchtown, NJ) in 1.5 mL centrifuge tubes and then applied to small petri-dishes. After the diet-sample mixture cooled and solidified, 12 WCR larvae were added to each plate. The plates were sealed and maintained at ambient laboratory conditions with regard to temperature, lighting and relative humidity. Lysates from *E. coli* BL21*(DE3) cultures harboring the empty pET29a vector were used as negative controls. Mortality was assessed on day 4 and day 7, or optionally day 3 and day 6. For this and all subsequent tables showing insecticidal activity on CRW, the abbreviations for the "Remarks" column are as follows: s=small larvae, sm=small/medium larvae, m=medium larvae, mb=medium/big larvae, b=big larvae, vb=very big larvae. For this an all subsequent Tables showing the insecticidal activity of NitromobCRW or a variant thereof, the "SEQ ID NO." refers to the amino acid sequence of the protein. As shown in Table 1, lysate from the culture expressing p(Nitromob) showed strong bioactivity against WCR. The *N. mobilis* protein was renamed NitromobCRW.

TABLE 1

Insecticidal activity of Nitromob against Western Corn Rootworm

| Treatment | SEQ ID NO. | Day 4 | | | Day 7 | | |
| --- | --- | --- | --- | --- | --- | --- | --- |
| | | Dead | % Mort. | Remarks | Dead | % Mort. | Remarks |
| BL21*/pET29a-empty | | 0 | 0% | b | 1 | 8% | b |
| BL21*/(pNitromob) | 39 | 10 | 83% | m | 12 | 100% | |

Example 2: Variants of NitromobCRW Possess Insecticidal Activity Against WCR Mutations were introduced into NitrornobCRW and the protein stability and insecticidal activity of bacterial lysates comprising the NitromobCRW mutant variant were assayed. Mutations include amino acid changes at various residues and also the insertion of leucine residues. These mutations were introduced to determine if a NitromobCRW mutant variant could be designed which maintained insecticidal activity but would be digestible in a Simulated Gastric Fluid (SGF) assay. Such a NitromobCRW variant may have commercial value, for example through transgenic expression in a plant to confer insecticidal properties to the plant.

Insecticidal activity was determined using diet-incorporation assays performed essentially as described in Example 1, using 12 WCR larvae per experimental assay. Results are shown in Tables 2-6. SEQ ID NOs correspond to the amino acid sequence of the variant. The treatments shown in Tables 5 and 6 also indicate the dilution of the bacterial lysate used. All the NitromobCRW mutant variants show insecticidal activity by day 6 or 7.

TABLE 2

Insecticidal activity of mutant variant of NitromobCRW against WCR

| Treatment | SEQ ID NO. | Day 4 | | | Day 7 | | |
| --- | --- | --- | --- | --- | --- | --- | --- |
| | | Dead | % Mort. | Remarks | Dead | % Mort. | Remarks |
| BL21*/pET29a-empty | | 0 | 0% | mb/b | 2 | 17% | b |
| BL21*/NitromobCRW Y213L | 73 | 7 | 58% | m | 12 | 100% | |

TABLE 3

Insecticidal activity of mutant variants of NitromobCRW against WCR

| Treatment | SEQ ID NO. | Day 4 | | | Day 7 | | |
| --- | --- | --- | --- | --- | --- | --- | --- |
| | | Dead | % Mort. | Remarks | Dead | % Mort. | Remarks |
| BL21*/pET29a-empty | | 0 | 0% | b | 1 | 8% | b |
| BL21*/NitromobCRW Y213L/I215L | 47 | 10 | 83% | sm | 12 | 100% | |
| BL21*/NitromobCRW V177L/I215L | 72 | 11 | 92% | s | 12 | 100% | |
| BL21*/NitromobCRW E186L/I215L | 71 | 12 | 100% | | 12 | 100% | |
| BL21*/NitromobCRW E196L/I215L | 70 | 11 | 92% | s | 12 | 100% | |
| BL21*/NitromobCRW V193L/I215L | 69 | 12 | 100% | | 12 | 100% | |
| BL21*/NitromobCRW I175L | 42 | 11 | 92% | s | 12 | 100% | |
| BL21*/NitromobCRW I208L | 43 | 10 | 83% | s | 12 | 100% | |
| BL21*/NitromobCRW I245L | 48 | 11 | 92% | m | 12 | 100% | |
| BL21*/NitromobCRW I255L | 49 | 12 | 100% | | 12 | 100% | |
| BL21*/NitromobCRW I215F | 45 | 11 | 92% | s | 12 | 100% | |
| BL21*/NitromobCRW I215Y | 46 | 12 | 100% | | 12 | 100% | |
| BL21*/NitromobCRW V220L | 56 | 10 | 83% | 1 s, 1 m | 12 | 100% | |
| BL21*/NitromobCRW V167L | 55 | 12 | 100% | | 12 | 100% | |
| BL21*/NitromobCRW V122L | 54 | 12 | 100% | | 12 | 100% | |
| BL21*/NitromobCRW I257L | 51 | 12 | 100% | | 12 | 100% | |
| BL21*/NitromobCRW I265L | 50 | 9 | 75% | sm | 12 | 100% | |
| BL21*/NitromobCRW I98L | 40 | 11 | 92% | m | 12 | 100% | |
| BL21*/NitromobCRW V99L | 41 | 11 | 92% | m | 12 | 100% | |
| BL21*/NitromobCRW wild-type | 39 | 10 | 83% | m | 12 | 100% | |

TABLE 4

Insecticidal activity of mutant variants of NitromobCRW against WCR

| Treatment | SEQ ID NO. | Day 4 Dead | % Mort. | Remarks | Day 6 Dead | % Mort. | Remarks |
|---|---|---|---|---|---|---|---|
| BL21*/pET29a-empty | | 0 | 0% | mb/b | 0 | 0% | b |
| BL21*/NitromobCRW V203S/M204L | 65 | 12 | 100% | | 12 | 100% | |
| BL21*/NitromobCRW V185L | 68 | 11 | 92% | s | 12 | 100% | |
| BL21*/NitromobCRW T218F | 67 | 12 | 100% | | 12 | 100% | |
| BL21*/NitromobCRW T218L | 66 | 10 | 83% | 1 s, 1 m | 12 | 100% | |
| BL21*/NitromobCRW I175L/I215L | 60 | 10 | 83% | 2 m | 12 | 100% | |
| BL21*/NitromobCRW I215L I255L | 62 | 11 | 92% | 1 m | 12 | 100% | |
| BL21*/NitromobCRW I208L/I215L | 61 | 11 | 92% | 1 m | 12 | 100% | |
| BL21*/NitromobCRW I255L/I257L | 63 | 12 | 100% | | 12 | 100% | |
| BL21*/NitromobCRW Y213F/I215L | 59 | 10 | 83% | 1 s, 1 m | 12 | 100% | |

TABLE 5

Insecticidal activity of mutant variant of NitromobCRW against WCR

| Treatment | SEQ ID NO. | Day 3 Dead | % Mort. | Remarks | Day 6 Dead | % Mort. | Remarks |
|---|---|---|---|---|---|---|---|
| BL21*/pET29a-empty | | 0 | 0% | b | 3 | 25% | vb |
| BL21*/NitromobCRW I215L/V203S/M204L, undiluted | 74 | 9 | 75% | m | 12 | 100% | |
| BL21*/NitromobCRW I215L/V203S/M204L, 1:50 | 74 | 1 | 8% | b | 7 | 58% | mb/b |

TABLE 6

Insecticidal activity of NitromobCRW I215L against WCR

| Treatment | SEQ ID NO. | Day 4 Dead | % Mort. | Remarks | Day 6 Dead | % Mort. | Remarks |
|---|---|---|---|---|---|---|---|
| BL21*/pET29a-empty | | 0 | 0% | mb | 0 | 0% | b |
| BL21*/NitromobCRW I215L-1:2 | 44 | 10 | 83% | sm | 12 | 100% | |
| BL21*/NitromobCRW I215L-1:20 | 44 | 2 | 17% | m | 12 | 100% | |
| BL21*/NitromobCRW I215L-1:50 | 44 | 2 | 17% | m | 11 | 92% | m |
| BL21*/NitromobCRW I215L-1:200 | 44 | 0 | 0% | mb | 0 | 0% | b |

Example 3: Simulated Gastric Fluid Testing on *E. coli* Lysate Preparations

This example describes the assay performed to determine SGF digestibility. Each NitromobCRW protein variant was produced in *E. coli* strain BL21*(DE3). The expression level of the variant in the bacterial strain and the solubility of the variant is indicated in Table 7. Bacterial lysates in 50 mM potassium phosphate pH 7.0, 50 mM sodium chloride were diluted to 3 mg/mL (total protein concentration) for the digestibility analysis. The digestion reaction was initiated by adding 15 µL lysate to 285 µL simulated gastric fluid [10 Units pepsin/µg protein, or approximately 1579 Units pepsin/mL, in G-Con solution (2 mg/mL sodium chloride, pH 1.2)] at 37° C. At 5 minutes, 100 µL of the lysate-SGF reaction was removed and the reaction terminated by adding it to 100 µL of preheated (95° C.) stop solution comprised of 65% Tricine Loading Buffer (Bio-rad 2× Tricine Load Buffer w/10% β-mercaptoethanol) and 35% 500 mM sodium bicarbonate, pH 11.0. A zero time (TO) point was produced by adding 5 µL of test lysate to preheated (95° C.) 100 µL Stop Solution and 95 µL of simulated gastric fluid. All samples were heated at 95° C. for 5 minutes, and then stored on ice until SDS-PAGE analysis. Thirty microliters of each reaction were loaded on a 10-20% Tris-tricine peptide gel prior to standard protein gel electrophoresis. The Tris-tricine gel was fixed for 20 minutes with a 40% methanol: 10% acetic acid mixture immediately after the electrophoresis. The gel was then stained with GelCode Blue protein stain for 1 hour at room temperature. After 1 hour, the polyacrylamide gel was de-stained with distilled water for at least 12 hours. Results are shown qualitatively in Table 7. A "Fail" for the T5 test means that intact or partially digested NitromobCRW protein variant was detectable by GelCode Blue protein stain following gel electrophoresis, indicating that the protein was not fully digestible in the SGF assay. A "Pass" for the T5 Test means intact NitromobCRW protein variant was not detectable, indicating that the NitromobCRW protein variant was digestible in the SGF assay. The insecticidal activity ("Active") of the NitromobCRW protein variant is also indicated, with a "yes" indicating insecticidal activity, as shown in the previous examples.

TABLE 7

Digestion of mutant variants of NitromobCRW in SGF Assay

| Mutant variant | SEQ ID NO. | Expression | Solubility | T5 Test | Active |
|---|---|---|---|---|---|
| NitromobCRW I175L | 42 | ++++ | High | Fail | Yes |
| NitromobCRW I208L | 43 | ++++ | High | Fail | Yes |
| NitromobCRW I215L | 44 | ++++ | High | Fail | Yes |
| NitromobCRW I245L | 48 | ++++ | High | Fail | Yes |
| NitromobCRW I255L | 49 | ++++ | High | Fail | Yes |
| NitromobCRW I215F | 45 | +++ | High | Fail | Yes |
| NitromobCRW I215Y | 46 | ++++ | High | Fail | Yes |
| NitromobCRW 214-Leu-215 | 57 | +++ | None | | |
| NitromobCRW 215-Leu-216 | 58 | +++ | None | | |
| NitromobCRW G216A | 52 | +++ | None | | |
| NitromobCRW G216L | 53 | +++ | None | | |
| NitromobCRW V220L | 56 | ++++ | High | Fail | Yes |
| NitromobCRW V167L | 55 | ++++ | High | Fail | Yes |
| NitromobCRW V122L | 54 | ++++ | High | Fail | Yes |
| NitromobCRW I257L | 51 | ++++ | High | Fail | Yes |
| NitromobCRW I265L | 50 | ++ | Low | Fail | Yes |
| NitromobCRW I98L | 40 | ++++ | High | Fail | Yes |
| NitromobCRW V99L | 41 | ++++ | High | Fail | Yes |
| NitromobCRW I175L/I215L | 60 | ++++ | High | Fail | Yes |
| NitromobCRW I215L/I255L | 62 | ++++ | High | Fail | Yes |
| NitromobCRW I208L/I215L | 61 | ++++ | High | Fail | Yes |
| NitromobCRW I255L/I257L | 63 | ++++ | High | Fail | Yes |
| NitromobCRW Y213F/I215L | 59 | ++++ | High | Fail | Yes |
| NitromobCRW L214S/I215L | 64 | +++ | None | | |
| NitromobCRW V203S/M204L | 65 | ++++ | High | Fail | Yes |
| NitromobCRW T218L | 66 | ++++ | High | Fail | Yes |
| NitromobCRW T218F | 67 | ++++ | High | Fail | Yes |
| NitromobCRW V185L | 68 | ++++ | High | Fail | Yes |
| NitromobCRW V177L/I215L | 72 | ++++ | High | Fail | Yes |
| NitromobCRW E186L/I215L | 71 | ++++ | High | Fail | Yes |
| NitromobCRW E196L/I215L | 70 | ++++ | High | Fail | Yes |
| NitromobCRW V193L/I215L | 69 | ++++ | High | Fail | Yes |
| NitromobCRW Y213L/I215L | 47 | ++++ | High | Pass | Yes |
| NitromobCRW Y213L | 73 | ++++ | High | Fail | Yes |
| NitromobCRW V203S/M204L/I215L | 74 | ++++ | High | Fail | Yes |

Surprisingly, of all the NitromobCRW variants produced, only NitromobCRW Y213L/I215L (SEQ ID NO: 47) definitively passed the SGF assay T5 test. NitromobCRW I215L (SEQ ID NO: 44) exhibited better digestibility than the wild-type protein but this variant did not pass the T5 test. Interestingly, NitromobCRW variants 214-Leu-215, 215-Leu-216, G216A, G216L, and L214S/I215L were not soluble, and NitrobCRW I265L variant had low solubility. These data suggest that a domain, motif, or fold in this region of the protein is critical for protein function and/or protein stability.

Example 4: Purified NitromobCRW Variant Y213L/I215L is Insecticidal Against WCR

This variant was further characterized for its insecticidal properties. Two liters of E. coli BL21*(DE3) cells harboring pET-NitromobCRW Y213L/I215L were grown at 37° C. in LB media. IPTG (1 mM) was added to the cultures when the O.D. reached 0.8-1.0 and then the cultures were moved to 18° C. for 18 hours. The cell pellet was harvested and re-suspended in 20 mM Tris, pH 8.5 with 10% glycerol. The cells were lysed using a French pressure cell; the lysate was then spun at 100 k×g in an ultracentrifuge. The supernatant was collected and then filtered before loading onto a HiPrepQ anion-exchange column that was pre-equilibrated in 20 mM Tris, pH 8.5 with 10% glycerol. The HiPrepQ column bound NitromobCRW Y213L/I215L effectively; the protein was eluted from the column using a linear NaCl gradient. The high-salt buffer consisted of 20 mM Tris, pH 8.5, 0.5 M NaCl with 10% glycerol. The purest fractions were pooled and then concentrated to approximately 2 mL. The protein was loaded onto a Sephadex 200 gel filtration column that had been pre-equilibrated in 1×PBS. Fractions from the Sephadex 200 column were analyzed for purity by SDS-PAGE (NitromobCRW Y213L/I215L (SEQ ID NO: 47) has a predicted molecular weight of 32.1 kDa). The purest fractions were pooled and then concentrated to 7.2 mg/mL, prior to storage at −80° C. The pure protein was then tested against 12 WCR larvae over a range of concentrations in the diet-incorporation method essentially as described in Example 1. As shown in Table 8, NitromobCRW Y213L/I215L is efficacious against WCR; NitromobCRW Y213L/I215L at 50 µg/mL produced at least 75% mortality at day 6.

TABLE 8

Insecticidal activity of purified NitromobCRW Y213L/I215L against WCR

| Treatment | Day 3 Dead | % Mort. | Remarks | Day 6 Dead | % Mort. | Remarks |
|---|---|---|---|---|---|---|
| 1X PBS | 0 | 0% | b | 1 | 8% | b |
| 1X PBS | 0 | 0% | b | 0 | 0% | b |
| NitromobCRW Y213L/I215L 200 µg/mL | 3 | 25% | sm | 12 | 100% | |
| NitromobCRW Y213L/I215L 200 µg/mL | 6 | 50% | m/mb | 12 | 100% | |
| NitromobCRW Y213L/I215L 100 µg/mL | 3 | 25% | m/mb | 12 | 100% | |
| NitromobCRW Y213L/I215L 100 µg/mL | 2 | 17% | mb | 11 | 92% | 1 b |
| NitromobCRW Y213L/I215L 50 µg/mL | 1 | 8% | mb | 12 | 100% | |
| NitromobCRW Y213L/I215L 50 µg/mL | 0 | 0% | mb | 9 | 75% | 2 m, 1 b |
| NitromobCRW Y213L/I215L 25 µg/mL | 2 | 17% | mb | 4 | 33% | mb |
| NitromobCRW Y213L/I215L 25 µg/mL | 4 | 33% | mb | 7 | 58% | mb |
| NitromobCRW Y213L/I215L 12.5 µg/mL | 1 | 8% | mb/b | 1 | 8% | m/mb |
| NitromobCRW Y213L/I215L 12.5 µg/mL | 0 | 0% | mb/b | 1 | 8% | m/mb |

Example 5: NitromobCRWCRW Y213L/I215L Possesses Insecticidal Activity Against Cry-Resistant Western Corn Rootworm Strains To determine if NitromobCRW Y213L/I215L (SEQ ID NO: 47) toxicity is through a mode-of-action separate from Cry3-related proteins, NitromobCRW Y213L/I215L lysate was purified as in Example 4 and was tested for efficacy against a strain of WCR that is resistant to an eCry3.1Ab toxin (eCry3.1Ab-R; see Table 9), a strain of WCR that is resistant to a modified Cry3A (mCry3A) toxin (mCry3A-R; see Table 10) and a strain of WCR that is resistant to a Cry3Bb toxin (Cry3Bb-R; see Table 11). Diet-incorporation assays were performed over a range of NitromobCRW Y213L/I215L protein essentially as described in Example 4, and mortality was assessed either on day 3 and day 6 (Table 9) or on day 2 and day 7 (Table 10). NitrobmobCRW Y213L/I215L was tested twice at a number of concentrations (µg/mL), as indicated in Tables 9, 10 and 11. The negative control had only 1×PBS. Each assay was performed with 12 WCR larvae. As shown in Tables 9, 10 and 11, NitromobCRW Y213L/I215L demonstrates insecticidal activity against Cry-resistant WCR strains.

TABLE 9

Insecticidal activity of purified NitromobCRW Y213L/I215L against eCry3.1Ab-Resistant WCR

| Treatment | Day 3 Dead | % Mort. | Remarks | Day 6 Dead | % Mort. | Remarks |
|---|---|---|---|---|---|---|
| 1X PBS | 0 | 0% | b | 0 | 0% | b |
| 1X PBS | 0 | 0% | b | 1 | 8% | b |
| NitromobCRW Y213L/I215L 200 µg/mL | 9 | 75% | m | 12 | 100% | |
| NitromobCRW Y213L/I215L 200 µg/mL | 5 | 42% | m | 12 | 100% | |
| NitromobCRW Y213L/I215L 100 µg/mL | 7 | 58% | m/mb | 12 | 100% | |
| NitromobCRW Y213L/I215L 100 µg/mL | 7 | 58% | m/mb | 12 | 100% | |
| NitromobCRW Y213L/I215L 50 g/mL | 2 | 17% | mb | 11 | 92% | m |
| NitromobCRW Y213L/I215L 50 µg/mL | 0 | 0% | mb | 9 | 75% | 2 m, 1 b |
| NitromobCRW Y213L/I215L 25 µg/mL | 1 | 8% | mb | 8 | 67% | m |
| NitromobCRW Y213L/I215L 25 g/mL | 0 | 0% | mb | 8 | 67% | mb |
| NitromobCRW Y213L/I215L 12.5 g/mL | 0 | 0% | mb | 5 | 42% | b |
| NitromobCRW Y213L/I215L 12.5 µg/mL | 0 | 0% | mb | 4 | 33% | b |

TABLE 10

Insecticidal activity of purified NitromobCRW Y213L/I215L against mCry3A-Resistant WCR

| Treatment | Day 2 Dead | % Mort. | Remarks | Day 7 Dead | % Mort. | Remarks |
|---|---|---|---|---|---|---|
| 1X PBS | 0 | 0% | mb/b | 0 | 0% | b/vb |
| 1X PBS | 2 | 17% | mb/b | 3 | 25% | b |
| NitromobCRW Y213L/I215L 200 µg/mL | 2 | 17% | mb/b | 12 | 100% | |
| NitromobCRW Y213L/I215L 200 µg/mL | 1 | 8% | mb/b | 12 | 100% | |
| NitromobCRW Y213L/I215L 100 µg/mL | 0 | 0% | mb/b | 12 | 100% | |
| NitromobCRW Y213L/I215L 100 µg/mL | 0 | 0% | mb/b | 11 | 92% | mb |
| NitromobCRW Y213L/I215L 50 g/mL | 0 | 0% | mb | 9 | 75% | mb |
| NitromobCRW Y213L/I215L 50 µg/mL | 1 | 8% | mb/b | 11 | 92% | m |
| NitromobCRW Y213L/I215L 25 µg/mL | 1 | 8% | mb/b | 8 | 67% | 3 mb, 1 b |
| NitromobCRW Y213L/I215L 25 µg/mL | 0 | 0% | mb/b | 8 | 67% | mb |

TABLE 10-continued

Insecticidal activity of purified NitromobCRW Y213L/I215L against mCry3A-Resistant WCR

| Treatment | Day 2 | | | Day 7 | | |
|---|---|---|---|---|---|---|
| | Dead | % Mort. | Remarks | Dead | % Mort. | Remarks |
| NitromobCRW Y213L/I215L 12.5 μg/mL | 0 | 0% | mb/b | 6 | 50% | b |
| NitromobCRW Y213L/I215L 12.5 μg/mL | 0 | 0% | mb/b | 4 | 33% | b |

TABLE 11

Insecticidal activity of purified NitromobCRW Y213L/I215L against Cry3Bb-Resistant WCR

| Treatment | Day 3 | | Day 9 | |
|---|---|---|---|---|
| | % Mort. | Remarks | % Mort. | Remarks |
| 1 × PBS | 0% | b | 0% | b |
| 1 × PBS | 0% | b | 0% | b |
| NitromobCRW Y213L I215L 200 μg/mL | 25% | mb | 100% | |
| NitromobCRW Y213L I215L 200 μg/mL | 8% | mb | 100% | |
| NitromobCRW Y213L I215L 100 μg/mL | 8% | mb/b | 100% | |
| NitromobCRW Y213L I215L 100 μg/mL | 0% | mb/b | 92% | 1 b |
| NitromobCRW Y213L I215L 50 μg/mL | 0% | b | 83% | 2mb |
| NitromobCRW Y213L I215L 50 μg/mL | 0% | b | 75% | 3mb |
| NitromobCRW Y213L I215L 25 μg/mL | 0% | b | 0% | b |
| NitromobCRW Y213L I215L 25 μg/mL | 0% | b | 0% | b |
| NitromobCRW Y213L I215L 12.5 μg/mL | 0% | b | 25% | b |
| NitromobCRW Y213L I215L 12.5 μg/mL | 0% | b | 0% | b |

Example 6: NitromobCRW Y213L/I215L does not Possess Insecticidal Activity Against Lepidopterans Lysates from bacterial cultures expressing NitromobCRW Y213L/I215L (SEQ ID NO: 47) were tested for bioactivity on a panel of Lepidopteran insect pests using diet-overlay bioassays. European corn borer (ECB), black cutworm (BCW), and corn earworm (CEW), and Fall armyworm (FAW) were each tested for NitromobCRW insecticidal activity by a diet-incorporation assay similar to that of Example 1. 12 L1 larvae were tested for each experiment, using lysates from Bl21*(DE3) bacterial cultures harboring a gene encoding for NitromobCRW Y213L/I215L (SEQ ID NO: 9). A positive-control sample for BCW, CEW, and FAW consisted of larvae exposed to E. coli BL21*(DE3) lysates expressing a Vip3 protein. 1×PBS alone and lysates from BL21*(DE3) bacterial cultures harboring the empty pET29 vector were used as negative controls. Mortality was assessed on day 7. Larvae that reach the L3 stage were not significantly affected by the treatment. If larvae only reach L2 stage, then it is possible that the treatment caused growth inhibition. If the larvae remain at the L1 stage throughout the treatment then growth inhibition occurred. This can also be considered "effective mortality" as the larvae will not develop beyond the L1 stage even if they remain alive. For Tables 11-14, L1=1st instar, L2=2nd instar, L3=3rd instar. NitromobCRW was not active against the tested Lepidopteran insect pests in these experimental conditions (Tables 12-15).

TABLE 12

Insecticidal activity of NitromobCRW Y213L/I215L against CEW

| Treatment | #Dead | % Mort. | L1 | L2 | L3 |
|---|---|---|---|---|---|
| BL21*/pET29a-empty | | 0% | | | 12 |
| BL21*/pET-Vip3D (+) | 12 | 100% | | | |
| 50 mM KPi pH 7.0, 50 mM NaCl | | 0% | | | 12 |
| 1 × PBS | | 0% | | | 12 |
| NitromobCRW Y213L/I215L 250 μg/mL | | 0% | | | 12 |
| NitromobCRW Y213L/I215L 100 μg/mL | | 0% | | | 12 |
| NitromobCRW Y213L/I215L 40 μg/mL | | 0% | | | 12 |

TABLE 13

Insecticidal activity of NitromobCRW Y213L/I215L against FAW

| Treatment | #Dead | % Mort. | L1 | L2 | L3 |
|---|---|---|---|---|---|
| BL21*/pET29a-empty | | 0% | | | 12 |
| BL21*/pET-Vip3D (+) | 12 | 100% | | | |
| 50 mM KPi pH 7.0, 50 mM NaCl | | 0% | | | 12 |
| 1 × PBS | | 0% | | | 12 |
| NitromobCRW Y213L/I215L 250 μg/mL | | 0% | | | 12 |
| NitromobCRW Y213L/I215L 100 μg/mL | | 0% | | | 12 |
| NitromobCRW Y213L/I215L 40 μg/mL | | 0% | | | 12 |

TABLE 14

Insecticidal activity of NitromobCRW Y213L/I215L against BCW

| Treatment | #Dead | % Mort. | L1 | L2 | L3 |
|---|---|---|---|---|---|
| BL21*/pET29a-empty | | 0% | | | 12 |
| BL21*/pET-Vip3D (+) | 12 | 100% | | | |
| 50 mM KPi pH 7.0, 50 mM NaCl | | 0% | | | 12 |
| 1 × PBS | | 0% | | | 12 |
| NitromobCRW Y213L/I215L 250 μg/mL | | 0% | | | 12 |
| NitromobCRW Y213L/I215L 100 μg/mL | | 0% | | | 12 |
| NitromobCRW Y213L/I215L 40 μg/mL | | 0% | | | 12 |

TABLE 15

Insecticidal activity of NitromobCRW Y213L/I215L against ECB

| ECB Treatment | #Dead | % Mort. | L1 | L2 | L3 |
|---|---|---|---|---|---|
| BL21*/pET29a-empty | | 0% | | | 12 |
| BL21*/pET-Vip3D (+) | 12 | 100% | | | |
| 50 mM KPi pH 7.0, 50 mM NaCl | | 0% | | | 12 |
| 1 × PBS | | 0% | | | 12 |
| NitromobCRW Y213L/I215L 250 µg/mL | | 0% | | | 12 |
| NitromobCRW Y213L/I215L 100 µg/mL | | 0% | | | 12 |
| NitromobCRW Y213L/I215L 40 µg/mL | | 0% | | | 12 |

Example 7: NitromobCRW Y213L/I215L Possesses Insecticidal Activity Against Northern Corn Rootworm NitromobCRW Y213L/I215L was purified as in Example 1 and was tested for efficacy against 12 Northern Corn Rootworm (NCR) larvae for each concentration in a diet-incorporation assay, performed essentially as described in Example 1. The negative control had only 1×PBS.

TABLE 16

Insecticidal activity of NitromobCRW Y213L/I215L against NCR

| | Day 3 | | Day 6 | |
|---|---|---|---|---|
| Treatment | % Mort. | Remarks | % Mort. | Remarks |
| 1 × PBS | 17% | mb | 25% | mb/b |
| 1 × PBS | 25% | mb | 42% | mb/b |
| NitromobCRW Y213L I215L 200 µg/mL | 75% | m | 100% | |
| NitromobCRW Y213L I215L 200 µg/mL | 75% | m | 100% | |
| NitromobCRW Y213L I215L 100 µg/mL | 33% | mb | 92% | 1m |
| NitromobCRW Y213L I215L 100 µg/mL | 67% | m/mb | 92% | m |
| NitromobCRW Y213L I215L 50 µg/mL | 50% | mb | 100% | |
| NitromobCRW Y213L I215L 50 µg/mL | 33% | mb | 92% | m |
| NitromobCRW Y213L I215L 25 µg/mL | 25% | mb | 83% | m |
| NitromobCRW Y213L I215L 25 µg/mL | 33% | mb | 92% | m |
| NitromobCRW Y213L I215L 12.5 µg/mL | 17% | mb | 75% | m |
| NitromobCRW Y213L I215L 12.5 µg/mL | 25% | mb | 100% | |

Example 8: NitromobCRW Y213L/I215L Possesses Insecticidal Activity Against Southern Corn Rootworm NitromobCRW Y213L/I215L was purified as in Example 1 and was tested for efficacy against 12 Southern Corn Rootworm (SCR) larvae in a diet-incorporation assay, performed essentially as described in Example 1. NitromobCRW Y213L/I215L (SEQ ID NO: 47) was tested at a range of concentration from 100 µg/mL to 400 µg/mL. The negative control had only 1×PBS. As shown in Table 16, NitromobCRW Y213L/I215L demonstrates insecticidal activity against SCR.

TABLE 16

Insecticidal activity of NitromobCRW Y213L/I215L against SCR

| | Day 4 | | | Day 6 | | |
|---|---|---|---|---|---|---|
| Treatment | Dead | % Mort. | Remarks | Dead | % Mort. | Remarks |
| 1X PBS | 0 | 0% | b | 0 | 0% | vb |
| 1X PBS | 0 | 0% | b | 0 | 0% | vb |
| NitromobCRW Y213L/I215L 400 µg/mL | 12 | 100% | | 12 | 100% | |
| NitromobCRW Y213L/I215L 400 µg/mL | 11 | 92% | mb | 12 | 100% | |
| NitromobCRW Y213L/I215L 200 µg/mL | 9 | 75% | 2 m, 1 b | 12 | 100% | |
| NitromobCRW Y213L/I215L 200 µg/mL | 9 | 75% | m | 11 | 92% | m |
| NitromobCRW Y213L/I215L 100 µg/mL | 5 | 42% | mb | 9 | 75% | 1 m, 2 b |
| NitromobCRW Y213L/I215L 100 µg/mL | 10 | 83% | 1 m, 1 b | 11 | 92% | b |

Example 9: Transformation of Maize with NitromobCRW Y213L/I215L

A binary vector construct suitable for *Agrobacterium*-mediated transformation of NitromobCRW Y213L/I215L is produced. The binary vector comprises a maize optimized NitromobCRW Y213L/I215L coding sequence (SEQ ID NO: 38), operably linked at the 5' end to a promoter suitable for driving expression in plants and operably linked at the 3' end to a terminator sequence. Maize codon optimization is performed, for example, using the methods described in U.S. Pat. No. 6,320,100 (incorporated by reference herein). The construct is transformed into *Agrobacterium tumefaciens* using standard molecular biology techniques known to those skilled in the art. To prepare the Agrobacteria for transformation, cells are cultured in liquid YPC media at 28° C. and 220 rpm overnight. *Agrobacterium* transformation of immature maize embryos is performed essentially as described in Negrotto et al., 2000, (*Plant Cell Reports* 19: 798-803). For this example, all media constituents are essentially as described in Negrotto et al., supra. However, various media constituents known in the art may be substituted.

Following transformation, selection, and regeneration, plants are assayed for the presence of the gene encoding the selectable marker and the NitromobCRW Y213L/I215L maize codon-optimized coding sequence using TaqMan® analysis. Plants are also tested for the presence of the vector backbone. Plants negative for the vector backbone and comprising one copy of the transgene are transferred to the greenhouse and assayed for resistance to WCR damage.

Example 10: Maize Plants Expressing NitromobCRW Y213L/I215L have Insecticidal Activity Against WCR The presence of NitromobCRW Y213L/I215L was detected by ELISA as ng/mg total soluble protein (TSP) in leaf or root tissue from each event. Insecticidal activity was determined using a Root Segment Bioassay. Briefly, samples of maize root tissue from each event were excised when NitromobCRW variant-expressing maize events reached the V3-V4 stage. Maize root tissue was placed in a petri dish and then infested with 12 WCR larvae. Two root tissue samples (Rep1 and Rep2) are evaluated for feeding holes (FH) and scarring damage at day 3. Root tissue from non-transformed (null) maize served as the negative control. Scoring for insect damage is performed using the following: ND=none detected; FH=feeding holes; L=light scarring; M=medium scarring; H=heavy scarring; ++=excellent performer; +=good performer; =poor performer

TABLE 17

Insecticidal activity of Transgenic NitromobCRW Y213L/I215L Maize against WCR

| Event No. | NiromobCRW Conc. (ng/mg TSP) | WCR Activity |
| --- | --- | --- |
| 43 | 34 | + |
| 47 | 43 | + |
| 49 | 56 | ++ |
| 50 | 39 | + |
| 52 | 13 | − |
| 56 | 42 | − |
| 57 | 17 | + |
| 61 | 32 | − |
| 81 | 28 | − |
| 83 | 36 | − |
| 86 | 21 | + |
| 91 | 30 | + |
| 93 | 35 | + |

Example 11: NitromobCRW Y213L/I215L in Combination with an Interfering RNA have Insecticidal Activity Against WCR NitromobCRW and/or a NitromobCRW variant are purified as bacterial lysates as in Example 1 or purified as proteins similar to Example 4. dsRNA against an essential target and known to have insecticidal activity is prepared. In non-limiting examples, the dsRNA may target a gene encoding vacuolar ATP synthase, beta-tubulin, 26S proteosome subunit p28 protein, EF1α 48D, troponin I, tetraspanin, gamma-coatomer, beta-coatomer, and/or juvenile hormone epoxide hydrolase (WO Publication Nos. WO2018/026770, WO2018/026773, and WO2018/026774; U.S. Pat. No. 7,812,219; each herein incorporated by reference). The dsRNA and purified NitromobCRW protein are tested for insecticidal efficacy against WCR in a diet-incorporation assay, performed essentially as described in Example 1 but with the addition of the dsRNA in the artificial diet.
Asdadasdas

Example 12. NiromobCRW with C-Terminal Extension is Active Against CRW

This example describes the effects of attaching a C-terminal peptide to the NitromobCRW protein. A pET-NitromobCRW-Y213L/I215L:C-terminal extension construct encoding SEQ ID NO:77 was cloned into E. coli. The C-terminal extension peptide comprises SEQ ID NO:76, and is a combination of a linker sequence (amino acids 1-35 of SEQ ID NO:76) and a SUMO-tag (amino acids 36-133 of SEQ ID NO:76). SUMO is a small ubiquitin-like modifier protein that when fused to a protein of interest, enhances functional protein production in prokaryotic and eukaryotic expression systems, based upon significantly improved protein stability and solubility. Following the expression and purification of the fusion protein, the SUMO-tag is typically cleaved off by specific (SUMO) proteases via their endopeptidase activity in vitro to generate the desired released protein partner. For this example, the C-terminal extension peptide (SEQ ID NO:76) was not cleaved from the NitromobCRW protein and intact extended protein (NitromobCRW-Cterm-SUMO; SEQ ID NO:77) was tested for SGF digestibility and insecticidal activity against WCR.

The SGF analysis of NitromobCRW-Y213L-I215L-Cterm-SUMO was the same as described above. Digestibility of NitromobCRW-Y213L-I215L-Cterm-SUMO was compared with NitromobCRW-Y213L-I215L without a C-terminal extension as a control. The NitromobCRW-Y213L-I215L-Cterm-SUMO protein was also tested for activity against WCR as described above.

Results of the SGF digestibility assay demonstrated that NitromobCRW-Y213L-I215L-Cterm-SUMO is digested before the 5 minute time-point. Therefore, the addition of the Cterm SUMO tag had no effect on the digestibility of the NitromobCRW protein. The SGF gels for the tagged and un-tagged protein were nearly identical (data not shown). Results of the bioassay, shown in Table 18, demonstrate that the NitromobCRW protein with a C-terminal extension peptide is as active as NitromobCRW protein without a C-terminal extension peptide.

TABLE 18

Bioactivity of NitromobCRW-Cterm-SUMO protein against WCR.

| NitromobCRW-Cterm-SUMO Conc (µg/ml) | % WCR Mortality |
| --- | --- |
| 200 | 100 |
| 100 | 80 |
| 50 | 60 |
| 25 | 20 |
| 12.5 | 8 |
| 1 × PBS (control) | 8 |

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. An expression cassette comprising a promoter operably linked to a heterologous nucleic acid molecule, said molecule comprising:
   (a) the nucleotide sequence of SEQ ID NO: 9; or
   (b) a nucleotide sequence that encodes a polypeptide, wherein the amino acid sequence of the polypeptide comprises SEQ ID NO: 47; or
   (c) a nucleotide sequence that encodes a polypeptide, wherein the amino acid sequence of the polypeptide comprises SEQ ID NO: 39 having amino acid substitutions at positions Y213 and I215.

2. A nucleic acid molecule comprising the nucleic acid sequence of SEQ ID NO: 9.

3. A polypeptide comprising the amino acid sequence of SEQ ID NO: 47.

4. A vector comprising the expression cassette of claim 1.

5. A host cell comprising the expression cassette of claim 1.

6. The host cell of claim 5 wherein the cell is a bacterial host cell.

7. The host cell of claim 5 wherein the cell is a plant host cell.

8. A method for producing a polypeptide with insecticidal activity, comprising culturing the host cell of claim 5 under conditions in which the nucleic acid molecule encoding the polypeptide is expressed.

9. A method of producing a plant having enhanced insect resistance as compared to a control plant, comprising:
   (a) introducing a nucleic acid molecule comprising the expression cassette of claim 1 into a plant part; and
   (b) regenerating the plant part into a plant that expresses the nucleic acid molecule and that has enhanced insect resistance as compared to a control plant that does not comprise the nucleic acid molecule comprising the expression cassette of claim 1.

10. The method of claim 9, wherein the expression cassette encodes a polypeptide comprising the amino acid sequence of SEQ ID NO:47.

11. A method of producing a plant having enhanced insect resistance as compared to a control plant, comprising:
   crossing a first parent plant with a second parent plant, wherein at least the first parent plant comprises within its genome a nucleic acid molecule that comprises the expression cassette of claim 1; and
   producing, from said cross, a progeny plant, wherein the progeny plant comprises the nucleic acid molecule in its genome and exhibits enhanced insect resistance as compared to a control plant.

12. A transgenic plant comprising a nucleic acid molecule which confers enhanced insect resistance, wherein said nucleic acid molecule comprises the expression cassette of claim 1.

13. The transgenic plant of claim 12, wherein said plant is a monocotyledonous plant.

14. The transgenic plant of claim 12, wherein said plant is maize.

15. The transgenic plant of claim 12, further comprising a second heterologous nucleic acid molecule encoding a second pesticidal agent.

16. The transgenic plant of claim 15, wherein the second pesticidal agent is an interfering RNA molecule.

17. A composition comprising an agricultural carrier and the polypeptide of claim 3.

18. A method for controlling a Coleopteran pest population comprising contacting said population with an effective insect-controlling amount of the polypeptide of claim 3.

19. The expression cassette of claim 1, wherein the heterologous nucleic acid molecule comprises a nucleotide sequence that encodes a polypeptide, wherein the amino acid sequence of the polypeptide comprises the amino acid sequence of SEQ ID NO: 47.

* * * * *

SEQUENCE LISTING

<160> NUMBER OF SEQ ID NOS: 74

<210> SEQ ID NO 1
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 1

| | |
|---|---|
| atgggtatta gcataagtat agttgcaggc cacgataaat cggcgtctag tgtgaacgct | 60 |
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gattgttaag | 300 |
| acccaggaat tgtcaacaa ttcaagacaa aggggacgt tcaatgtggc gataacagag | 360 |
| tcggtaaata atacgacgtc gtctaattgg agtacgggag ggacccttac gatcggccaa | 420 |
| aaattctctt acggggttaa gttcctggga gccggagcgg aaggagaaac ctcgttatcc | 480 |
| tacagccaaa gttgggggt gggggacag gaatctaaat ccatcacagt cggctcatcc | 540 |
| agcggcgttt cggtagaatt agaccctggt gaaagcgttc ttgccgaact tagtgcctcg | 600 |
| agaggggtta tgaaagttcg tatacggtat aacgcttacc ttataggtaa caccgctgtg | 660 |
| aattacaacc caacctataa ggaccatcat ttctggagcc ttggggttgc cggagtcatg | 720 |
| gctaagggtg ggatcactaa ctccgtacag tcaactgagg atatcgaaat cggctattac | 780 |
| tctaattcaa aaatagaatt gaaagacaag gctacaggcg cattaaaggc ggcgtataat | 840 |
| atggccgacg ccccagggca gtcggcagct gagtcgcgtc aacctgcgct ggacgaagca | 900 |
| taa | 903 |

<210> SEQ ID NO 2
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 2

| | |
|---|---|
| atgggtatta gcataagtat agttgcaggc cacgataaat cggcgtctag tgtgaacgct | 60 |
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gttagttaag | 300 |
| acccaggaat tgtcaacaa ttcaagacaa aggggacgt tcaatgtggc gataacagag | 360 |
| tcggtaaata atacgacgtc gtctaattgg agtacgggag ggacccttac gatcggccaa | 420 |
| aaattctctt acggggttaa gttcctggga gccggagcgg aaggagaaac ctcgttatcc | 480 |
| tacagccaaa gttgggggt gggggacag gaatctaaat ccatcacagt cggctcatcc | 540 |
| agcggcgttt cggtagaatt agaccctggt gaaagcgttc ttgccgaact tagtgcctcg | 600 |
| agaggggtta tgaaagttcg tatacggtat aacgcttacc ttataggtaa caccgctgtg | 660 |
| aattacaacc caacctataa ggaccatcat ttctggagcc ttggggttgc cggagtcatg | 720 |
| gctaagggtg ggatcactaa ctccgtacag tcaactgagg atatcgaaat cggctattac | 780 |

```
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                  903
```

<210> SEQ ID NO 3
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 3

```
atgggtatta gcataagtat agttgcaggc cacgataaat cggcgtctag tgtgaacgct     60
acagggactg ttcaacacgt tatcaccgat caggagcgca ctaccttcca cttgggtgat    120
aaacagttga aggacgccgt taaggcttat tttggaaagt ctcccaacga cgtgtatttg    180
cactctccga cgccctgggg tgacttgtac aaaaagtatt catggcccca agtccagatg    240
atactggtcg ttcagtcggc agaaatcctt ggtatcacta gcgagccggt gattttaaag    300
acccaggaat tgtcaacaa ttcaagacaa aaggggacgt caatgtggc gataacagag     360 tcggtaaata atacgacgtc gtctaattgg agtacgggag ggacccttac gatcggccaa    420
aaattctctt acggggttaa gttcctggga gccggagcgg aaggagaaac ctcgttatcc    480
tacagccaaa gttgggggt gggggacag gaatctaaat ccatcacagt cggctcatcc     540
agcggcgttt cggtagaatt agaccctggt gaaagcgttc ttgccgaact tagtgcctcg    600
agaggggtta tgaaagttcg tatacggtat aacgcttacc ttataggtaa caccgctgtg    660
aattacaacc caacctataa ggaccatcat ttctggagcc ttggggttgc cggagtcatg    720
gctaagggtg ggatcactaa ctccgtacag tcaactgagg atatcgaaat cggctattac    780
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                  903
```

<210> SEQ ID NO 4
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 4

```
atgggtatta gcataagtat agttgcaggc cacgataaat cggcgtctag tgtgaacgct     60
acagggactg ttcaacacgt tatcaccgat caggagcgca ctaccttcca cttgggtgat    120
aaacagttga aggacgccgt taaggcttat tttggaaagt ctcccaacga cgtgtatttg    180
cactctccga cgccctgggg tgacttgtac aaaaagtatt catggcccca agtccagatg    240
atactggtcg ttcagtcggc agaaatcctt ggtatcacta gcgagccggt gattgttaag    300
acccaggaat tgtcaacaa ttcaagacaa aaggggacgt caatgtggc gataacagag     360 tcggtaaata atacgacgtc gtctaattgg agtacgggag ggacccttac gatcggccaa    420
aaattctctt acggggttaa gttcctggga gccggagcgg aaggagaaac ctcgttatcc    480
tacagccaaa gttgggggt gggggacag gaatctaaat cctgacagt cggctcatcc      540 agcggcgttt cggtagaatt agaccctggt gaaagcgttc ttgccgaact tagtgcctcg    600
```

| | |
|---|---|
| agaggggtta tgaaagttcg tatacggtat aacgcttacc ttataggtaa caccgctgtg | 660 |
| aattacaacc caacctataa ggaccatcat ttctggagcc ttggggttgc cggagtcatg | 720 |
| gctaagggtg ggatcactaa ctccgtacag tcaactgagg atatcgaaat cggctattac | 780 |
| tctaattcaa aaatagaatt gaaagacaag gctacaggcg cattaaaggc ggcgtataat | 840 |
| atggccgacg ccccagggca gtcggcagct gagtcgcgtc aacctgcgct ggacgaagca | 900 |
| taa | 903 |

<210> SEQ ID NO 5
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 5

| | |
|---|---|
| atgggtatta gcataagtat agttgcaggc cacgataaat cggcgtctag tgtgaacgct | 60 |
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gattgttaag | 300 |
| acccaggaat ttgtcaacaa ttcaagacaa aaggggacgt caatgtggc gataacagag | 360 |
| tcggtaaata atacgacgtc gtctaattgg agtacgggag ggacccttac gatcggccaa | 420 |
| aaattctctt acggggttaa gttcctggga gccggagcgg aaggagaaac ctcgttatcc | 480 |
| tacagccaaa gttgggggt gggggacag gaatctaaat ccatcacagt cggctcatcc | 540 |
| agcggcgttt cggtagaatt agaccctggt gaaagcgttc ttgccgaact tagtgcctcg | 600 |
| agaggggtta tgaaagttcg tctgcggtat aacgcttacc ttataggtaa caccgctgtg | 660 |
| aattacaacc caacctataa ggaccatcat ttctggagcc ttggggttgc cggagtcatg | 720 |
| gctaagggtg ggatcactaa ctccgtacag tcaactgagg atatcgaaat cggctattac | 780 |
| tctaattcaa aaatagaatt gaaagacaag gctacaggcg cattaaaggc ggcgtataat | 840 |
| atggccgacg ccccagggca gtcggcagct gagtcgcgtc aacctgcgct ggacgaagca | 900 |
| taa | 903 |

<210> SEQ ID NO 6
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 6

| | |
|---|---|
| atgggtatta gcataagtat agttgcaggc cacgataaat cggcgtctag tgtgaacgct | 60 |
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gattgttaag | 300 |
| acccaggaat ttgtcaacaa ttcaagacaa aaggggacgt caatgtggc gataacagag | 360 |
| tcggtaaata atacgacgtc gtctaattgg agtacgggag ggacccttac gatcggccaa | 420 |
| aaattctctt acggggttaa gttcctggga gccggagcgg aaggagaaac ctcgttatcc | 480 |

| | | |
|---|---|---|
| tacagccaaa gttgggnggt ggggggacag aatctaaat ccatcacagt cggctcatcc | 540 | |
| agcggcgttt cggtagaatt agaccctggt gaaagcgttc ttgccgaact tagtgcctcg | 600 | |
| agaggggtta tgaaagttcg tatacggtat aacgcttacc ttctgggtaa caccgctgtg | 660 | |
| aattacaacc caacctataa ggaccatcat ttctggagcc ttggggttgc cggagtcatg | 720 | |
| gctaagggtg ggatcactaa ctccgtacag tcaactgagg atatcgaaat cggctattac | 780 | |
| tctaattcaa aaatagaatt gaaagacaag gctacaggcg cattaaaggc ggcgtataat | 840 | |
| atggccgacg ccccagggca gtcggcagct gagtcgcgtc aacctgcgct ggacgaagca | 900 | |
| taa | 903 | |

<210> SEQ ID NO 7
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 7

| | | |
|---|---|---|
| atgggtatta gcataagtat agttgcaggc cacgataaat cggcgtctag tgtgaacgct | 60 | |
| acagggactg ttcaacacgt tatcaccgat caggagcgca ctaccttcca cttgggtgat | 120 | |
| aaacagttga aggacgccgt taaggcttat tttggaaagt ctcccaacga cgtgtatttg | 180 | |
| cactctccga cgccctgggg tgacttgtac aaaaagtatt catggcccca agtccagatg | 240 | |
| atactggtcg ttcagtcggc agaaatcctt ggtatcacta gcgagccggt gattgttaag | 300 | |
| acccaggaat ttgtcaacaa ttcaagacaa aaggggacgt tcaatgtggc gataacagag | 360 | |
| tcggtaaata atacgacgtc gtctaattgg agtacgggag ggacccttac gatcggccaa | 420 | |
| aaattctctt acggggttaa gttcctggga gccggagcgg aaggagaaac ctcgttatcc | 480 | |
| tacagccaaa gttgggnggt ggggggacag aatctaaat ccatcacagt cggctcatcc | 540 | |
| agcggcgttt cggtagaatt agaccctggt gaaagcgttc ttgccgaact tagtgcctcg | 600 | |
| agaggggtta tgaaagttcg tatacggtat aacgcttacc tttttggtaa caccgctgtg | 660 | |
| aattacaacc caacctataa ggaccatcat ttctggagcc ttggggttgc cggagtcatg | 720 | |
| gctaagggtg ggatcactaa ctccgtacag tcaactgagg atatcgaaat cggctattac | 780 | |
| tctaattcaa aaatagaatt gaaagacaag gctacaggcg cattaaaggc ggcgtataat | 840 | |
| atggccgacg ccccagggca gtcggcagct gagtcgcgtc aacctgcgct ggacgaagca | 900 | |
| taa | 903 | |

<210> SEQ ID NO 8
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 8

| | | |
|---|---|---|
| atgggtatta gcataagtat agttgcaggc cacgataaat cggcgtctag tgtgaacgct | 60 | |
| acagggactg ttcaacacgt tatcaccgat caggagcgca ctaccttcca cttgggtgat | 120 | |
| aaacagttga aggacgccgt taaggcttat tttggaaagt ctcccaacga cgtgtatttg | 180 | |
| cactctccga cgccctgggg tgacttgtac aaaaagtatt catggcccca agtccagatg | 240 | |
| atactggtcg ttcagtcggc agaaatcctt ggtatcacta gcgagccggt gattgttaag | 300 | |

| | | |
|---|---|---|
| acccaggaat ttgtcaacaa ttcaagacaa aaggggacgt tcaatgtggc gataacagag | 360 | |
| tcggtaaata atacgacgtc gtctaattgg agtacgggag ggaccettac gatcggccaa | 420 | |
| aaattctctt acggggttaa gttcctggga gccggagcgg aaggagaaac ctcgttatcc | 480 | |
| tacagccaaa gttgggggt gggggggacag gaatctaaat ccatcacagt cggctcatcc | 540 | |
| agcggcgttt cggtagaatt agaccctggt gaaagcgttc ttgccgaact tagtgcctcg | 600 | |
| agaggggtta tgaaagttcg tatacggtat aacgcttacc tttatggtaa caccgctgtg | 660 | |
| aattacaacc caacctataa ggaccatcat ttctggagcc ttggggttgc cggagtcatg | 720 | |
| gctaagggtg ggatcactaa ctccgtacag tcaactgagg atatcgaaat cggctattac | 780 | |
| tctaattcaa aaatagaatt gaaagacaag gctacaggcg cattaaaggc ggcgtataat | 840 | |
| atggccgacg ccccagggca gtcggcagct gagtcgcgtc aacctgcgct ggacgaagca | 900 | |
| taa | 903 | |

<210> SEQ ID NO 9
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 9

| | | |
|---|---|---|
| atgggtatta gcataagtat agttgcaggc cacgataaat cggcgtctag tgtgaacgct | 60 | |
| acagggactg ttcaacacgt tatcaccgat caggagcgca ctaccttcca cttgggtgat | 120 | |
| aaacagttga aggacgccgt taaggcttat tttggaaagt ctcccaacga cgtgtatttg | 180 | |
| cactctccga cgccctgggg tgacttgtac aaaaagtatt catggcccca agtccagatg | 240 | |
| atactggtcg ttcagtcggc agaaatcctt ggtatcacta gcgagccggt gattgttaag | 300 | |
| acccaggaat ttgtcaacaa ttcaagacaa aaggggacgt tcaatgtggc gataacagag | 360 | |
| tcggtaaata atacgacgtc gtctaattgg agtacgggag ggaccettac gatcggccaa | 420 | |
| aaattctctt acggggttaa gttcctggga gccggagcgg aaggagaaac ctcgttatcc | 480 | |
| tacagccaaa gttgggggt gggggggacag gaatctaaat ccatcacagt cggctcatcc | 540 | |
| agcggcgttt cggtagaatt agaccctggt gaaagcgttc ttgccgaact tagtgcctcg | 600 | |
| agaggggtta tgaaagttcg tatacggtat aacgctttac ttctgggtaa caccgctgtg | 660 | |
| aattacaacc caacctataa ggaccatcat ttctggagcc ttggggttgc cggagtcatg | 720 | |
| gctaagggtg ggatcactaa ctccgtacag tcaactgagg atatcgaaat cggctattac | 780 | |
| tctaattcaa aaatagaatt gaaagacaag gctacaggcg cattaaaggc ggcgtataat | 840 | |
| atggccgacg ccccagggca gtcggcagct gagtcgcgtc aacctgcgct ggacgaagca | 900 | |
| taa | 903 | |

<210> SEQ ID NO 10
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 10

| | | |
|---|---|---|
| atgggtatta gcataagtat agttgcaggc cacgataaat cggcgtctag tgtgaacgct | 60 | |
| acagggactg ttcaacacgt tatcaccgat caggagcgca ctaccttcca cttgggtgat | 120 | |
| aaacagttga aggacgccgt taaggcttat tttggaaagt ctcccaacga cgtgtatttg | 180 | |

```
cactctccga cgccctgggg tgacttgtac aaaaagtatt catggcccca agtccagatg      240
atactggtcg ttcagtcggc agaaatcctt ggtatcacta gcgagccggt gattgttaag      300
acccaggaat tgtcaacaa ttcaagacaa aaggggacgt tcaatgtggc gataacagag       360
tcggtaaata atacgacgtc gtctaattgg agtacgggag ggaccttac gatcggccaa       420 aaattctctt acggggttaa gttcctggga gccggagcgg aaggagaaac ctcgttatcc      480
tacagccaaa gttgggggt gggggacag gaatctaaat ccatcacagt cggctcatcc        540
agcggcgttt cggtagaatt agaccctggt gaaagcgttc ttgccgaact tagtgcctcg      600
agaggggtta tgaaagttcg tatacggtat aacgcttacc ttataggtaa caccgctgtg      660
aattacaacc caacctataa ggaccatcat ttctggagcc ttggggttgc cggagtcatg      720
gctaagggtg ggctgactaa ctccgtacag tcaactgagg atatcgaaat cggctattac      780
tctaattcaa aaatagaatt gaaagacaag gctacaggcg cattaaaggc ggcgtataat      840
atggccgacg ccccagggca gtcggcagct gagtcgcgtc aacctgcgct ggacgaagca      900
taa                                                                    903
```

<210> SEQ ID NO 11
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 11

```
atgggtatta gcataagtat agttgcaggc cacgataaat cggcgtctag tgtgaacgct       60
acagggactg ttcaacacgt tatcaccgat caggagcgca ctaccttcca cttgggtgat     120
aaacagttga aggacgccgt taaggcttat tttggaaagt ctcccaacga cgtgtatttg     180
cactctccga cgccctgggg tgacttgtac aaaaagtatt catggcccca agtccagatg     240
atactggtcg ttcagtcggc agaaatcctt ggtatcacta gcgagccggt gattgttaag     300
acccaggaat tgtcaacaa ttcaagacaa aaggggacgt tcaatgtggc gataacagag      360
tcggtaaata atacgacgtc gtctaattgg agtacgggag ggaccttac gatcggccaa      420 aaattctctt acggggttaa gttcctggga gccggagcgg aaggagaaac ctcgttatcc    480
tacagccaaa gttgggggt gggggacag gaatctaaat ccatcacagt cggctcatcc      540
agcggcgttt cggtagaatt agaccctggt gaaagcgttc ttgccgaact tagtgcctcg    600
agaggggtta tgaaagttcg tatacggtat aacgcttacc ttataggtaa caccgctgtg    660
aattacaacc caacctataa ggaccatcat ttctggagcc ttggggttgc cggagtcatg    720
gctaagggtg gatcactaa ctccgtacag tcaactgagg atctggaaat cggctattac     780
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                  903
```

<210> SEQ ID NO 12
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 12

```
atgggtatta gcataagtat agttgcaggc cacgataaat cggcgtctag tgtgaacgct    60
acagggactg ttcaacacgt tatcaccgat caggagcgca ctaccttcca cttgggtgat   120
aaacagttga aggacgccgt taaggcttat tttggaaagt ctcccaacga cgtgtatttg   180
cactctccga cgccctgggg tgacttgtac aaaaagtatt catggcccca agtccagatg   240
atactggtcg ttcagtcggc agaaatcctt ggtatcacta gcgagccggt gattgttaag   300
acccaggaat ttgtcaacaa ttcaagacaa aaggggacgt tcaatgtggc gataacagag   360
tcggtaaata tacgacgtc gtctaattgg agtacgggag ggacccttac gatcggccaa    420
aaattctctt acggggttaa gttcctggga gccggagcgg aaggagaaac ctcgttatcc   480
tacagccaaa gttgggggt gggggacag gaatctaaat ccatcacagt cggctcatcc     540
agcggcgttt cggtagaatt agaccctggt gaaagcgttc ttgccgaact tagtgcctcg   600
agaggggtta tgaaagttcg tatacggtat aacgcttacc ttataggtaa caccgctgtg   660
aattacaacc caacctataa ggaccatcat ttctggagcc ttggggttgc cggagtcatg   720
gctaagggtg ggatcactaa ctccgtacag tcaactgagg atatcgaaat cggctattac   780
tctaattcaa aattagaatt gaaagacaag gctacaggcg cattaaaggc ggcgtataat   840
atggccgacg ccccagggca gtcggcagct gagtcgcgtc aacctgcgct ggacgaagca   900
taa                                                                 903
```

<210> SEQ ID NO 13
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 13

```
atgggtatta gcataagtat agttgcaggc cacgataaat cggcgtctag tgtgaacgct    60
acagggactg ttcaacacgt tatcaccgat caggagcgca ctaccttcca cttgggtgat   120
aaacagttga aggacgccgt taaggcttat tttggaaagt ctcccaacga cgtgtatttg   180
cactctccga cgccctgggg tgacttgtac aaaaagtatt catggcccca agtccagatg   240
atactggtcg ttcagtcggc agaaatcctt ggtatcacta gcgagccggt gattgttaag   300
acccaggaat ttgtcaacaa ttcaagacaa aaggggacgt tcaatgtggc gataacagag   360
tcggtaaata tacgacgtc gtctaattgg agtacgggag ggacccttac gatcggccaa    420
aaattctctt acggggttaa gttcctggga gccggagcgg aaggagaaac ctcgttatcc   480
tacagccaaa gttgggggt gggggacag gaatctaaat ccatcacagt cggctcatcc     540
agcggcgttt cggtagaatt agaccctggt gaaagcgttc ttgccgaact tagtgcctcg   600
agaggggtta tgaaagttcg tatacggtat aacgcttacc ttataggtaa caccgctgtg   660
aattacaacc caacctataa ggaccatcat ttctggagcc ttggggttgc cggagtcatg   720
gctaagggtg ggatcactaa ctccgtacag tcaactgagg atatcgaatt aggctattac   780
tctaattcaa aaatagaatt gaaagacaag gctacaggcg cattaaaggc ggcgtataat   840
atggccgacg ccccagggca gtcggcagct gagtcgcgtc aacctgcgct ggacgaagca   900
taa                                                                 903
```

<210> SEQ ID NO 14
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 14

```
atgggtatta gcataagtat agttgcaggc cacgataaat cggcgtctag tgtgaacgct      60
acagggactg ttcaacacgt tatcaccgat caggagcgca ctaccttcca cttgggtgat     120
aaacagttga aggacgccgt taaggcttat tttggaaagt ctcccaacga cgtgtatttg     180
cactctccga cgccctgggg tgacttgtac aaaaagtatt catggcccca agtccagatg     240
atactggtcg ttcagtcggc agaaatcctt ggtatcacta gcgagccggt gattgttaag     300
acccaggaat ttgtcaacaa ttcaagacaa aaggggacgt caatgtggc gataacagag      360
tcggtaaata atacgacgtc gtctaattgg agtacgggag ggacccttac gatcggccaa     420
aaattctctt acggggttaa gttcctggga gccggagcgg aaggagaaac ctcgttatcc     480
tacagccaaa gttgggggt gggggacag gaatctaaat ccatcacagt cggctcatcc       540
agcggcgttt cggtagaatt agaccctggt gaaagcgttc ttgccgaact tagtgcctcg     600
agaggggtta tgaaagttcg tatacggtat aacgcttacc ttatagctaa caccgctgtg     660
aattacaacc caacctataa ggaccatcat ttctggagcc ttggggttgc cggagtcatg     720
gctaagggtg ggatcactaa ctccgtacag tcaactgagg atatcgaaat cggctattac     780
tctaattcaa aaatagaatt gaaagacaag gctacaggcg cattaaaggc ggcgtataat     840
atggccgacg ccccagggca gtcggcagct gagtcgcgtc aacctgcgct ggacgaagca     900
taa                                                                   903
```

<210> SEQ ID NO 15
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 15

```
atgggtatta gcataagtat agttgcaggc cacgataaat cggcgtctag tgtgaacgct      60
acagggactg ttcaacacgt tatcaccgat caggagcgca ctaccttcca cttgggtgat     120
aaacagttga aggacgccgt taaggcttat tttggaaagt ctcccaacga cgtgtatttg     180
cactctccga cgccctgggg tgacttgtac aaaaagtatt catggcccca agtccagatg     240
atactggtcg ttcagtcggc agaaatcctt ggtatcacta gcgagccggt gattgttaag     300
acccaggaat ttgtcaacaa ttcaagacaa aaggggacgt caatgtggc gataacagag      360
tcggtaaata atacgacgtc gtctaattgg agtacgggag ggacccttac gatcggccaa     420
aaattctctt acggggttaa gttcctggga gccggagcgg aaggagaaac ctcgttatcc     480
tacagccaaa gttgggggt gggggacag gaatctaaat ccatcacagt cggctcatcc       540
agcggcgttt cggtagaatt agaccctggt gaaagcgttc ttgccgaact tagtgcctcg     600
agaggggtta tgaaagttcg tatacggtat aacgcttacc ttatattaaa caccgctgtg     660
aattacaacc caacctataa ggaccatcat ttctggagcc ttggggttgc cggagtcatg     720
gctaagggtg ggatcactaa ctccgtacag tcaactgagg atatcgaaat cggctattac     780
tctaattcaa aaatagaatt gaaagacaag gctacaggcg cattaaaggc ggcgtataat     840
atggccgacg ccccagggca gtcggcagct gagtcgcgtc aacctgcgct ggacgaagca     900
taa                                                                   903
```

<210> SEQ ID NO 16
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 16

```
atgggtatta gcataagtat agttgcaggc cacgataaat cggcgtctag tgtgaacgct      60
acagggactg ttcaacacgt tatcaccgat caggagcgca ctaccttcca cttgggtgat     120
aaacagttga aggacgccgt taaggcttat tttggaaagt ctcccaacga cgtgtatttg     180
cactctccga cgccctgggg tgacttgtac aaaaagtatt catggcccca agtccagatg     240
atactggtcg ttcagtcggc agaaatcctt ggtatcacta gcgagccggt gattgttaag     300
acccaggaat ttgtcaacaa ttcaagacaa aaggggacgt tcaatgtggc gataacagag     360
tcgttaaata atacgacgtc gtctaattgg agtacgggag ggacccttac gatcggccaa     420
aaattctctt acggggttaa gttcctggga gccggagcgg aaggagaaac ctcgttatcc     480
tacagccaaa gttgggggt ggggggacag gaatctaaat ccatcacagt cggctcatcc     540
agcggcgttt cggtagaatt agaccctggt gaaagcgttc ttgccgaact tagtgcctcg     600
agaggggtta tgaaagttcg tatacggtat aacgcttacc ttataggtaa caccgctgtg     660
aattacaacc caacctataa ggaccatcat ttctggagcc ttggggttgc cggagtcatg     720
gctaagggtg ggatcactaa ctccgtacag tcaactgagg atatcgaaat cggctattac     780
tctaattcaa aaatagaatt gaaagacaag gctacaggcg cattaaaggc ggcgtataat     840
atggccgacg ccccagggca gtcggcagct gagtcgcgtc aacctgcgct ggacgaagca     900
taa                                                                   903
```

<210> SEQ ID NO 17
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 17

```
atgggtatta gcataagtat agttgcaggc cacgataaat cggcgtctag tgtgaacgct      60
acagggactg ttcaacacgt tatcaccgat caggagcgca ctaccttcca cttgggtgat     120
aaacagttga aggacgccgt taaggcttat tttggaaagt ctcccaacga cgtgtatttg     180
cactctccga cgccctgggg tgacttgtac aaaaagtatt catggcccca agtccagatg     240
atactggtcg ttcagtcggc agaaatcctt ggtatcacta gcgagccggt gattgttaag     300
acccaggaat ttgtcaacaa ttcaagacaa aaggggacgt tcaatgtggc gataacagag     360
tcggtaaata atacgacgtc gtctaattgg agtacgggag ggacccttac gatcggccaa     420
aaattctctt acggggttaa gttcctggga gccggagcgg aaggagaaac ctcgttatcc     480
tacagccaaa gttgggggtt aggggacag gaatctaaat ccatcacagt cggctcatcc     540
agcggcgttt cggtagaatt agaccctggt gaaagcgttc ttgccgaact tagtgcctcg     600
agaggggtta tgaaagttcg tatacggtat aacgcttacc ttataggtaa caccgctgtg     660
aattacaacc caacctataa ggaccatcat ttctggagcc ttggggttgc cggagtcatg     720
gctaagggtg ggatcactaa ctccgtacag tcaactgagg atatcgaaat cggctattac     780
tctaattcaa aaatagaatt gaaagacaag gctacaggcg cattaaaggc ggcgtataat     840
```

| | |
|---|---|
| atggccgacg cccagggca gtcggcagct gagtcgcgtc aacctgcgct ggacgaagca | 900 |
| taa | 903 |

<210> SEQ ID NO 18
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 18

| | |
|---|---|
| atgggtatta gcataagtat agttgcaggc cacgataaat cggcgtctag tgtgaacgct | 60 |
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gattgttaag | 300 |
| acccaggaat tgtcaacaa ttcaagacaa aaggggacgt tcaatgtggc gataacagag | 360 |
| tcggtaaata atacgacgtc gtctaattgg agtacgggag ggacccttac gatcggccaa | 420 |
| aaattctctt acggggttaa gttcctggga gccggagcgg aaggagaaac ctcgttatcc | 480 |
| tacagccaaa gttgggggt gggggacag gaatctaaat ccatcacagt cggctcatcc | 540 |
| agcggcgttt cggtagaatt agaccctggt gaaagcgttc ttgccgaact tagtgcctcg | 600 |
| agaggggtta tgaaagttcg tatacggtat aacgcttacc ttataggtaa caccgcttta | 660 |
| aattcaacc caacctataa ggaccatcat ttctggagcc ttggggttgc cggagtcatg | 720 |
| gctaagggtg ggatcactaa ctccgtacag tcaactgagg atatcgaaat cggctattac | 780 |
| tctaattcaa aaatagaatt gaaagacaag gctacaggcg cattaaaggc ggcgtataat | 840 |
| atggccgacg cccagggca gtcggcagct gagtcgcgtc aacctgcgct ggacgaagca | 900 |
| taa | 903 |

<210> SEQ ID NO 19
<211> LENGTH: 906
<212> TYPE: DNA
<213> ORGANISM: Artificial sequence
<220> FEATURE:
<223> OTHER INFORMATION: derived from Nitrococcus mobilis

<400> SEQUENCE: 19

| | |
|---|---|
| atgggtatta gcataagtat agttgcaggc cacgataaat cggcgtctag tgtgaacgct | 60 |
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gattgttaag | 300 |
| acccaggaat tgtcaacaa ttcaagacaa aaggggacgt tcaatgtggc gataacagag | 360 |
| tcggtaaata atacgacgtc gtctaattgg agtacgggag ggacccttac gatcggccaa | 420 |
| aaattctctt acggggttaa gttcctggga gccggagcgg aaggagaaac ctcgttatcc | 480 |
| tacagccaaa gttgggggt gggggacag gaatctaaat ccatcacagt cggctcatcc | 540 |
| agcggcgttt cggtagaatt agaccctggt gaaagcgttc ttgccgaact tagtgcctcg | 600 |
| agaggggtta tgaaagttcg tatacggtat aacgcttacc ttctgatagg taacaccgct | 660 |

```
gtgaattaca acccaaccta taaggaccat catttctgga gccttggggt tgccggagtc    720
atggctaagg gtgggatcac taactccgta cagtcaactg aggatatcga aatcggctat    780
tactctaatt caaaaataga attgaaagac aaggctacag gcgcattaaa ggcggcgtat    840
aatatggccg acgccccagg gcagtcggca gctgagtcgc gtcaacctgc gctggacgaa    900
gcataa                                                                906

<210> SEQ ID NO 20
<211> LENGTH: 906
<212> TYPE: DNA
<213> ORGANISM: Artificial sequence
<220> FEATURE:
<223> OTHER INFORMATION: derived from Nitrococcus mobilis

<400> SEQUENCE: 20
atgggtatta gcataagtat agttgcaggc cacgataaat cggcgtctag tgtgaacgct     60
acagggactg ttcaacacgt tatcaccgat caggagcgca ctaccttcca cttgggtgat    120
aaacagttga aggacgccgt taaggcttat tttggaaagt ctcccaacga cgtgtatttg    180
cactctccga cgccctgggg tgacttgtac aaaaagtatt catggcccca agtccagatg    240
atactggtcg ttcagtcggc agaaatcctt ggtatcacta gcgagccggt gattgttaag    300
acccaggaat tgtcaacaa ttcaagacaa aaggggacgt tcaatgtggc gataacagag    360
tcggtaaata atacgacgtc gtctaattgg agtacgggag ggacccttac gatcggccaa    420
aaattctctt acggggttaa gttcctggga gccggagcgg aaggagaaac ctcgttatcc    480
tacagccaaa gttgggggt ggggggacag gaatctaaat ccatcacagt cggctcatcc    540
agcggcgttt cggtagaatt agaccctggt gaaagcgttc ttgccgaact tagtgcctcg    600
agaggggtta tgaaagttcg tatacggtat aacgcttacc ttatattagg taacaccgct    660
gtgaattaca acccaaccta taaggaccat catttctgga gccttggggt tgccggagtc    720
atggctaagg gtgggatcac taactccgta cagtcaactg aggatatcga aatcggctat    780
tactctaatt caaaaataga attgaaagac aaggctacag gcgcattaaa ggcggcgtat    840
aatatggccg acgccccagg gcagtcggca gctgagtcgc gtcaacctgc gctggacgaa    900
gcataa                                                                906

<210> SEQ ID NO 21
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 21
atgggtatta gcataagtat agttgcaggc cacgataaat cggcgtctag tgtgaacgct     60
acagggactg ttcaacacgt tatcaccgat caggagcgca ctaccttcca cttgggtgat    120
aaacagttga aggacgccgt taaggcttat tttggaaagt ctcccaacga cgtgtatttg    180
cactctccga cgccctgggg tgacttgtac aaaaagtatt catggcccca agtccagatg    240
atactggtcg ttcagtcggc agaaatcctt ggtatcacta gcgagccggt gattgttaag    300
acccaggaat tgtcaacaa ttcaagacaa aaggggacgt tcaatgtggc gataacagag    360
tcggtaaata atacgacgtc gtctaattgg agtacgggag ggacccttac gatcggccaa    420
aaattctctt acggggttaa gttcctggga gccggagcgg aaggagaaac ctcgttatcc    480
tacagccaaa gttgggggt ggggggacag gaatctaaat ccatcacagt cggctcatcc    540
```

```
agcggcgttt cggtagaatt agaccctggt gaaagcgttc ttgccgaact tagtgcctcg    600
agaggggtta tgaaagttcg tatacggtat aacgcttttc ttctgggtaa caccgctgtg    660
aattacaacc caacctataa ggaccatcat ttctggagcc ttggggttgc cggagtcatg    720
gctaagggtg ggatcactaa ctccgtacag tcaactgagg atatcgaaat cggctattac    780
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                  903
```

<210> SEQ ID NO 22
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 22

```
atgggtatta gcataagtat agttgcaggc cacgataaat cggcgtctag tgtgaacgct     60
acagggactg ttcaacacgt tatcaccgat caggagcgca ctaccttcca cttgggtgat    120
aaacagttga aggacgccgt taaggcttat tttggaaagt ctcccaacga cgtgtatttg    180
cactctccga cgccctgggg tgacttgtac aaaaagtatt catggcccca agtccagatg    240
atactggtcg ttcagtcggc agaaatcctt ggtatcacta gcgagccggt gattgttaag    300
acccaggaat ttgtcaacaa ttcaagacaa aaggggacgt tcaatgtggc gataacagag    360
tcggtaaata tacgacgtc gtctaattgg agtacgggag ggacccttac gatcggccaa    420
aaattctctt acggggttaa gttcctggga gccggagcgg aaggagaaac ctcgttatcc    480
tacagccaaa gttgggggt ggggggacag gaatctaaat cccttacagt cggctcatcc     540
agcggcgttt cggtagaatt agaccctggt gaaagcgttc ttgccgaact tagtgcctcg    600
agaggggtta tgaaagttcg tatacggtat aacgcttacc ttctgggtaa caccgctgtg    660
aattacaacc caacctataa ggaccatcat ttctggagcc ttggggttgc cggagtcatg    720
gctaagggtg ggatcactaa ctccgtacag tcaactgagg atatcgaaat cggctattac    780
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                  903
```

<210> SEQ ID NO 23
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 23

```
atgggtatta gcataagtat agttgcaggc cacgataaat cggcgtctag tgtgaacgct     60
acagggactg ttcaacacgt tatcaccgat caggagcgca ctaccttcca cttgggtgat    120
aaacagttga aggacgccgt taaggcttat tttggaaagt ctcccaacga cgtgtatttg    180
cactctccga cgccctgggg tgacttgtac aaaaagtatt catggcccca agtccagatg    240
atactggtcg ttcagtcggc agaaatcctt ggtatcacta gcgagccggt gattgttaag    300
acccaggaat ttgtcaacaa ttcaagacaa aaggggacgt tcaatgtggc gataacagag    360
```

```
tcggtaaata atacgacgtc gtctaattgg agtacgggag ggacccttac gatcggccaa    420
aaattctctt acggggttaa gttcctggga gccggagcgg aaggagaaac ctcgttatcc    480
tacagccaaa gttgggggt gggggacag gaatctaaat ccatcacagt cggctcatcc     540
agcggcgttt cggtagaatt agaccctggt gaaagcgttc ttgccgaact tagtgcctcg    600
agaggggtta tgaaagttcg tctgcggtat aacgcttacc ttctgggtaa caccgctgtg    660
aattacaacc caacctataa ggaccatcat ttctggagcc ttggggttgc cggagtcatg    720
gctaagggtg ggatcactaa ctccgtacag tcaactgagg atatcgaaat cggctattac    780
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                 903

<210> SEQ ID NO 24
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 24
atgggtatta gcataagtat agttgcaggc cacgataaat cggcgtctag tgtgaacgct    60
acagggactg ttcaacacgt tatcaccgat caggagcgca ctaccttcca cttgggtgat    120
aaacagttga aggacgccgt taaggcttat tttggaaagt ctcccaacga cgtgtatttg    180
cactctccga cgccctgggg tgacttgtac aaaaagtatt catggcccca agtccagatg    240
atactggtcg ttcagtcggc agaaatcctt ggtatcacta gcgagccggt gattgttaag    300
acccaggaat ttgtcaacaa ttcaagacaa aaggggacgt caatgtggc gataacagag    360 tcggtaaata atacgacgtc gtctaattgg agtacgggag ggacccttac gatcggccaa    420
aaattctctt acggggttaa gttcctggga gccggagcgg aaggagaaac ctcgttatcc    480
tacagccaaa gttgggggt gggggacag gaatctaaat ccatcacagt cggctcatcc     540
agcggcgttt cggtagaatt agaccctggt gaaagcgttc ttgccgaact tagtgcctcg    600
agaggggtta tgaaagttcg tatacggtat aacgcttacc ttctgggtaa caccgctgtg    660
aattacaacc caacctataa ggaccatcat ttctggagcc ttggggttgc cggagtcatg    720
gctaagggtg ggatcactaa ctccgtacag tcaactgagg atctggaaat cggctattac    780
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                 903

<210> SEQ ID NO 25
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 25
atgggtatta gcataagtat agttgcaggc cacgataaat cggcgtctag tgtgaacgct    60
acagggactg ttcaacacgt tatcaccgat caggagcgca ctaccttcca cttgggtgat    120
aaacagttga aggacgccgt taaggcttat tttggaaagt ctcccaacga cgtgtatttg    180
cactctccga cgccctgggg tgacttgtac aaaaagtatt catggcccca agtccagatg    240
```

```
atactggtcg ttcagtcggc agaaatcctt ggtatcacta gcgagccggt gattgttaag    300
acccaggaat ttgtcaacaa ttcaagacaa aaggggacgt tcaatgtggc gataacagag    360 tcggtaaaata atacgacgtc gtctaattgg agtacgggag ggaccccttac gatcggccaa    420 aaattctctt acggggttaa gttcctggga gccggagcgg aaggagaaac ctcgttatcc    480
tacagccaaa gttggggggt gggggggacag gaatctaaat ccatcacagt cggctcatcc    540
agcggcgttt cggtagaatt agaccctggt gaaagcgttc ttgccgaact tagtgcctcg    600 agagggggtta tgaaagttcg tatacggtat aacgcttacc ttataggtaa caccgctgtg    660
aattacaacc caacctataa ggaccatcat ttctggagcc ttgggggttgc cggagtcatg    720 gctaagggtg ggatcactaa ctccgtacag tcaactgagg atctggaact gggctattac    780
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                   903
```

<210> SEQ ID NO 26
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 26

```
atgggtatta gcataagtat agttgcaggc cacgataaat cggcgtctag tgtgaacgct     60
acagggactg ttcaacacgt tatcaccgat caggagcgca ctaccttcca cttgggtgat    120
aaacagttga aggacgccgt taaggcttat tttggaaagt ctcccaacga cgtgtatttg    180
cactctccga cgccctgggg tgacttgtac aaaaagtatt catggcccca agtccagatg    240
atactggtcg ttcagtcggc agaaatcctt ggtatcacta gcgagccggt gattgttaag    300
acccaggaat ttgtcaacaa ttcaagacaa aaggggacgt tcaatgtggc gataacagag    360 tcggtaaaata atacgacgtc gtctaattgg agtacgggag ggaccccttac gatcggccaa    420 aaattctctt acggggttaa gttcctggga gccggagcgg aaggagaaac ctcgttatcc    480
tacagccaaa gttggggggt gggggggacag gaatctaaat ccatcacagt cggctcatcc    540
agcggcgttt cggtagaatt agaccctggt gaaagcgttc ttgccgaact tagtgcctcg    600 agagggggtta tgaaagttcg tatacggtat aacgcttaca gtctgggtaa caccgctgtg    660
aattacaacc caacctataa ggaccatcat ttctggagcc ttgggggttgc cggagtcatg    720 gctaagggtg ggatcactaa ctccgtacag tcaactgagg atatcgaaat cggctattac    780
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                   903
```

<210> SEQ ID NO 27
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 27

```
atgggtatta gcataagtat agttgcaggc cacgataaat cggcgtctag tgtgaacgct     60
```

| | |
|---|---|
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gattgttaag | 300 |
| acccaggaat tgtcaacaa ttcaagacaa aaggggacgt tcaatgtggc gataacagag | 360 |
| tcggtaaata atacgacgtc gtctaattgg agtacgggag ggaccettac gatcggccaa | 420 |
| aaattctctt acggggttaa gttcctggga gccggagcgg aaggagaaac ctcgttatcc | 480 |
| tacagccaaa gttgggggt ggggggacag gaatctaaat ccatcacagt cggctcatcc | 540 |
| agcggcgttt cggtagaatt agaccctggt gaaagcgttc ttgccgaact tagtgcctcg | 600 |
| agagggagtc ttaaagttcg tatacggtat aacgcttacc ttataggtaa caccgctgtg | 660 |
| aattacaacc caacctataa ggaccatcat ttctggagcc ttggggttgc cggagtcatg | 720 |
| gctaagggtg ggatcactaa ctccgtacag tcaactgagg atatcgaaat cggctattac | 780 |
| tctaattcaa aaatagaatt gaaagacaag gctacaggcg cattaaaggc ggcgtataat | 840 |
| atggccgacg ccccagggca gtcggcagct gagtcgcgtc aacctgcgct ggacgaagca | 900 |
| taa | 903 |

```
<210> SEQ ID NO 28
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 28
```

| | |
|---|---|
| atgggtatta gcataagtat agttgcaggc cacgataaat cggcgtctag tgtgaacgct | 60 |
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gattgttaag | 300 |
| acccaggaat tgtcaacaa ttcaagacaa aaggggacgt tcaatgtggc gataacagag | 360 |
| tcggtaaata atacgacgtc gtctaattgg agtacgggag ggaccettac gatcggccaa | 420 |
| aaattctctt acggggttaa gttcctggga gccggagcgg aaggagaaac ctcgttatcc | 480 |
| tacagccaaa gttgggggt ggggggacag gaatctaaat ccatcacagt cggctcatcc | 540 |
| agcggcgttt cggtagaatt agaccctggt gaaagcgttc ttgccgaact tagtgcctcg | 600 |
| agagggtta tgaaagttcg tatacggtat aacgcttacc ttataggtaa cttagctgtg | 660 |
| aattacaacc caacctataa ggaccatcat ttctggagcc ttggggttgc cggagtcatg | 720 |
| gctaagggtg ggatcactaa ctccgtacag tcaactgagg atatcgaaat cggctattac | 780 |
| tctaattcaa aaatagaatt gaaagacaag gctacaggcg cattaaaggc ggcgtataat | 840 |
| atggccgacg ccccagggca gtcggcagct gagtcgcgtc aacctgcgct ggacgaagca | 900 |
| taa | 903 |

```
<210> SEQ ID NO 29
<211> LENGTH: 903
<212> TYPE: DNA
<213> ORGANISM: Artificial sequence
<220> FEATURE:
<223> OTHER INFORMATION: derived from Nitrococcus mobilis
```

<400> SEQUENCE: 29

```
atgggtatta gcataagtat agttgcaggc cacgataaat cggcgtctag tgtgaacgct      60
acagggactg ttcaacacgt tatcaccgat caggagcgca ctaccttcca cttgggtgat     120
aaacagttga aggacgccgt taaggcttat tttggaaagt ctcccaacga cgtgtatttg     180
cactctccga cgccctgggg tgacttgtac aaaaagtatt catggcccca agtccagatg     240
atactggtcg ttcagtcggc agaaatcctt ggtatcacta gcgagccggt gattgttaag     300
acccaggaat ttgtcaacaa ttcaagacaa aaggggacgt tcaatgtggc gataacagag     360
tcggtaaata atacgacgtc gtctaattgg agtacgggag ggaccottac gatcggccaa     420
aaattctctt acggggttaa gttcctggga gccggagcgg aaggagaaac ctcgttatcc     480
tacagccaaa gttggggggt gggggacag gaatctaaat ccatcacagt cggctcatcc     540
agcggcgttt cggtagaatt agaccctggt gaaagcgttc ttgccgaact tagtgcctcg     600
agaggggtta tgaaagttcg tatacggtat aacgcttacc ttataggtaa ctttgctgtg     660
aattacaacc caacctataa ggaccatcat ttctggagcc ttggggttgc cggagtcatg     720
gctaaggggtg ggatcactaa ctccgtacag tcaactgagg atatcgaaat cggctattac     780
tctaattcaa aaatagaatt gaaagacaag gctacaggcg cattaaaggc ggcgtataat     840
atggccgacg ccccagggca gtcggcagct gagtcgcgtc aacctgcgct ggacgaagca     900
taa                                                                    903
```

<210> SEQ ID NO 30
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 30

```
atgggtatta gcataagtat agttgcaggc cacgataaat cggcgtctag tgtgaacgct      60
acagggactg ttcaacacgt tatcaccgat caggagcgca ctaccttcca cttgggtgat     120
aaacagttga aggacgccgt taaggcttat tttggaaagt ctcccaacga cgtgtatttg     180
cactctccga cgccctgggg tgacttgtac aaaaagtatt catggcccca agtccagatg     240
atactggtcg ttcagtcggc agaaatcctt ggtatcacta gcgagccggt gattgttaag     300
acccaggaat ttgtcaacaa ttcaagacaa aaggggacgt tcaatgtggc gataacagag     360
tcggtaaata atacgacgtc gtctaattgg agtacgggag ggaccottac gatcggccaa     420
aaattctctt acggggttaa gttcctggga gccggagcgg aaggagaaac ctcgttatcc     480
tacagccaaa gttggggggt gggggacag gaatctaaat ccatcacagt cggctcatcc     540
agcggcgttt cgctggaatt agaccctggt gaaagcgttc ttgccgaact tagtgcctcg     600
agaggggtta tgaaagttcg tatacggtat aacgcttacc ttataggtaa caccgctgtg     660
aattacaacc caacctataa ggaccatcat ttctggagcc ttggggttgc cggagtcatg     720
gctaaggggtg ggatcactaa ctccgtacag tcaactgagg atatcgaaat cggctattac     780
tctaattcaa aaatagaatt gaaagacaag gctacaggcg cattaaaggc ggcgtataat     840
atggccgacg ccccagggca gtcggcagct gagtcgcgtc aacctgcgct ggacgaagca     900
taa                                                                    903
```

<210> SEQ ID NO 31

```
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 31
atgggtatta gcataagtat agttgcaggc cacgataaat cggcgtctag tgtgaacgct    60
acagggactg ttcaacacgt tatcaccgat caggagcgca ctaccttcca cttgggtgat   120
aaacagttga aggacgccgt taaggcttat tttggaaagt ctcccaacga cgtgtatttg   180
cactctccga cgccctgggg tgacttgtac aaaaagtatt catggcccca agtccagatg   240
atactggtcg ttcagtcggc agaaatcctt ggtatcacta gcgagccggt gattgttaag   300
acccaggaat ttgtcaacaa ttcaagacaa aaggggacgt tcaatgtggc gataacagag   360
tcggtaaata atacgacgtc gtctaattgg agtacgggag ggacccttac gatcggccaa   420
aaattctctt acggggttaa gttcctggga gccggagcgg aaggagaaac ctcgttatcc   480
tacagccaaa gttgggggt gggggacag gaatctaaat ccatcacagt cggctcatcc   540
agcggcgttt cggtagaatt agaccctggt gaaagcttgc ttgccgaact tagtgcctcg   600
agaggggtta tgaaagttcg tatacggtat aacgcttacc ttctgggtaa caccgctgtg   660
aattacaacc caacctataa ggaccatcat ttctggagcc ttggggttgc cggagtcatg   720
gctaagggtg ggatcactaa ctccgtacag tcaactgagg atatcgaaat cggctattac   780
tctaattcaa aaatagaatt gaaagacaag gctacaggcg cattaaaggc ggcgtataat   840
atggccgacg ccccagggca gtcggcagct gagtcgcgtc aacctgcgct ggacgaagca   900
taa                                                                903

<210> SEQ ID NO 32
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 32
atgggtatta gcataagtat agttgcaggc cacgataaat cggcgtctag tgtgaacgct    60
acagggactg ttcaacacgt tatcaccgat caggagcgca ctaccttcca cttgggtgat   120
aaacagttga aggacgccgt taaggcttat tttggaaagt ctcccaacga cgtgtatttg   180
cactctccga cgccctgggg tgacttgtac aaaaagtatt catggcccca agtccagatg   240
atactggtcg ttcagtcggc agaaatcctt ggtatcacta gcgagccggt gattgttaag   300
acccaggaat ttgtcaacaa ttcaagacaa aaggggacgt tcaatgtggc gataacagag   360
tcggtaaata atacgacgtc gtctaattgg agtacgggag ggacccttac gatcggccaa   420
aaattctctt acggggttaa gttcctggga gccggagcgg aaggagaaac ctcgttatcc   480
tacagccaaa gttgggggt gggggacag gaatctaaat ccatcacagt cggctcatcc   540
agcggcgttt cggtagaatt agaccctggt gaaagcgttc ttgccctgct tagtgcctcg   600
agaggggtta tgaaagttcg tatacggtat aacgcttacc ttctgggtaa caccgctgtg   660
aattacaacc caacctataa ggaccatcat ttctggagcc ttggggttgc cggagtcatg   720
gctaagggtg ggatcactaa ctccgtacag tcaactgagg atatcgaaat cggctattac   780
tctaattcaa aaatagaatt gaaagacaag gctacaggcg cattaaaggc ggcgtataat   840
atggccgacg ccccagggca gtcggcagct gagtcgcgtc aacctgcgct ggacgaagca   900
```

```
                                                                         taa                                                            903

<210> SEQ ID NO 33
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 33
atgggtatta gcataagtat agttgcaggc cacgataaat cggcgtctag tgtgaacgct      60
acagggactg ttcaacacgt tatcaccgat caggagcgca ctaccttcca cttgggtgat     120
aaacagttga aggacgccgt taaggcttat tttggaaagt ctcccaacga cgtgtatttg     180
cactctccga cgccctgggg tgacttgtac aaaaagtatt catggcccca agtccagatg     240
atactggtcg ttcagtcggc agaaatcctt ggtatcacta gcgagccggt gattgttaag     300
acccaggaat ttgtcaacaa ttcaagacaa aaggggactg tcaatgtggc gataacagag     360
tcggtaaata atacgacgtc gtctaattgg agtacgggag ggacccttac gatcggccaa     420
aaattctctt acggggttaa gttcctggga gccggagcgg aaggagaaac ctcgttatcc     480
tacagccaaa gttgggggt ggggggacag gaatctaaat ccatcacagt cggctcatcc      540
agcggcgttt cggtactttt agaccctggt gaaagcgttc ttgccgaact tagtgcctcg     600
agaggggtta tgaaagttcg tatacggtat aacgcttacc ttctgggtaa caccgctgtg     660
aattacaacc caacctataa ggaccatcat ttctggagcc ttggggttgc cggagtcatg     720
gctaagggtg ggatcactaa ctccgtacag tcaactgagg atatcgaaat cggctattac     780
tctaattcaa aaatagaatt gaagacaag gctacaggcg cattaaaggc ggcgtataat      840
atggccgacg ccccagggca gtcggcagct gagtcgcgtc aacctgcgct ggacgaagca     900
taa                                                                   903

<210> SEQ ID NO 34
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 34
atgggtatta gcataagtat agttgcaggc cacgataaat cggcgtctag tgtgaacgct      60
acagggactg ttcaacacgt tatcaccgat caggagcgca ctaccttcca cttgggtgat     120
aaacagttga aggacgccgt taaggcttat tttggaaagt ctcccaacga cgtgtatttg     180
cactctccga cgccctgggg tgacttgtac aaaaagtatt catggcccca agtccagatg     240
atactggtcg ttcagtcggc agaaatcctt ggtatcacta gcgagccggt gattgttaag     300
acccaggaat ttgtcaacaa ttcaagacaa aaggggactg tcaatgtggc gataacagag     360
tcggtaaata atacgacgtc gtctaattgg agtacgggag ggacccttac gatcggccaa     420
aaattctctt acggggttaa gttcctggga gccggagcgg aaggagaaac ctcgttatcc     480
tacagccaaa gttgggggt ggggggacag gaatctaaat ccatcacact tggctcatcc      540
agcggcgttt cggtagaatt agaccctggt gaaagcgttc ttgccgaact tagtgcctcg     600
agaggggtta tgaaagttcg tatacggtat aacgcttacc ttctgggtaa caccgctgtg     660
aattacaacc caacctataa ggaccatcat ttctggagcc ttggggttgc cggagtcatg     720
```

| | |
|---|---|
| gctaagggtg ggatcactaa ctccgtacag tcaactgagg atatcgaaat cggctattac | 780 |
| tctaattcaa aaatagaatt gaaagacaag gctacaggcg cattaaaggc ggcgtataat | 840 |
| atggccgacg ccccagggca gtcggcagct gagtcgcgtc aacctgcgct ggacgaagca | 900 |
| taa | 903 |

<210> SEQ ID NO 35
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 35

| | |
|---|---|
| atgggtatta gcataagtat agttgcaggc cacgataaat cggcgtctag tgtgaacgct | 60 |
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gattgttaag | 300 |
| acccaggaat ttgtcaacaa ttcaagacaa aggggacgt tcaatgtggc gataacagag | 360 |
| tcggtaaaata atacgacgtc gtctaattgg agtacgggag ggaccccttac gatcggccaa | 420 |
| aaattctctt acggggttaa gttcctggga gccggagcgg aaggagaaac ctcgttatcc | 480 |
| tacagccaaa gttgggggt gggggacag gaatctaaat ccatcacagt cggctcatcc | 540 |
| agcggcgttt cggtagaatt agaccctggt gaaagcgttc ttgccgaact tagtgcctcg | 600 |
| agaggggtta tgaaagttcg tatacggtat aacgctttac ttataggtaa caccgctgtg | 660 |
| aattacaacc caacctataa ggaccatcat ttctggagcc ttggggttgc cggagtcatg | 720 |
| gctaagggtg ggatcactaa ctccgtacag tcaactgagg atatcgaaat cggctattac | 780 |
| tctaattcaa aaatagaatt gaaagacaag gctacaggcg cattaaaggc ggcgtataat | 840 |
| atggccgacg ccccagggca gtcggcagct gagtcgcgtc aacctgcgct ggacgaagca | 900 |
| taa | 903 |

<210> SEQ ID NO 36
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 36

| | |
|---|---|
| atgggtatta gcataagtat agttgcaggc cacgataaat cggcgtctag tgtgaacgct | 60 |
| acagggactg ttcaacacgt tatcaccgat caggagcgca ctaccttcca cttgggtgat | 120 |
| aaacagttga aggacgccgt taaggcttat tttggaaagt ctcccaacga cgtgtatttg | 180 |
| cactctccga cgccctgggg tgacttgtac aaaaagtatt catggcccca agtccagatg | 240 |
| atactggtcg ttcagtcggc agaaatcctt ggtatcacta gcgagccggt gattgttaag | 300 |
| acccaggaat ttgtcaacaa ttcaagacaa aggggacgt tcaatgtggc gataacagag | 360 |
| tcggtaaaata atacgacgtc gtctaattgg agtacgggag ggaccccttac gatcggccaa | 420 |
| aaattctctt acggggttaa gttcctggga gccggagcgg aaggagaaac ctcgttatcc | 480 |
| tacagccaaa gttgggggt gggggacag gaatctaaat ccatcacagt cggctcatcc | 540 |
| agcggcgttt cggtagaatt agaccctggt gaaagcgttc ttgccgaact tagtgcctcg | 600 |

```
agagggagtc ttaaagttcg tatacggtat aacgcttacc ttctgggtaa caccgctgtg    660
aattacaacc caacctataa ggaccatcat ttctggagcc ttggggttgc cggagtcatg    720
gctaagggtg ggatcactaa ctccgtacag tcaactgagg atatcgaaat cggctattac    780
tctaattcaa aaatagaatt gaaagacaag gctacaggcg cattaaaggc ggcgtataat    840
atggccgacg ccccagggca gtcggcagct gagtcgcgtc aacctgcgct ggacgaagca    900
taa                                                                  903

<210> SEQ ID NO 37
<211> LENGTH: 903
<212> TYPE: DNA
<213> ORGANISM: Nitrococcus mobilis

<400> SEQUENCE: 37
atgggcatca gtatcagcat cgtcgccggt cacgacaaat ccgcatcaag cgtaaacgcc     60
accggaaccg tgcagcacgt cattacggat caggaacgga cgactttcca tcttggcgat    120
aagcaactca aggacgccgt caaggcgtat ttcgggaaaa gcccgaacga cgtgtacttg    180
catagcccga cgccgtgggg tgatctctac aagaagtaca gttggccgca ggtccaaatg    240
atcctggtcg tccagagcgc ggagattctc ggcatcacct cggagccggt gatcgtcaag    300
actcaggagt tcgtgaataa tagccgccag aaaggcacct ttaacgttgc catcacggag    360
tcggtgaaca acaccacgtc ctccaactgg agtaccggcg gcacgcttac gatcgggcag    420
aagttctcct acggtgtcaa gtttctcggt gccggggccg aggggagac ttcgctgtcg    480 tacagccagt cgtggggagt cggggggcag gagtcgaaat cgatcactgt aggttcatcg    540
tccggggtga gtgtagagct tgatcccggc gagtccgttc tcgccgagct ctctgccagt    600
cggggcgtga tgaaagtacg aattcgctat aacgcctacc tcatcggcaa tacagccgtg    660
aattacaacc ccacctataa ggaccatcat ttctggagct tgggtgtcgc gggtgtcatg    720
gcgaaaggcg gcattaccaa ttcggtgcaa tcgaccgaag acatcgagat cggttattac    780
tccaattcca agatcgagct caaagataag gcgacgggtg ccttgaaggc cgcctacaat    840
atggccgacg cgcccgggca atcggccgcg gagtctcgcc agcctgctct cgatgaggcc    900
tag                                                                  903

<210> SEQ ID NO 38
<211> LENGTH: 903
<212> TYPE: DNA
<213> ORGANISM: Artificial sequence
<220> FEATURE:
<223> OTHER INFORMATION: derived from Nitrococcus mobilis

<400> SEQUENCE: 38
atgggcatca gtatcagcat cgtcgccggt cacgacaaat ccgcatcaag cgtaaacgcc     60
accggaaccg tgcagcacgt cattacggat caggaacgga cgactttcca tcttggcgat    120
aagcaactca aggacgccgt caaggcgtat ttcgggaaaa gcccgaacga cgtgtacttg    180
catagcccga cgccgtgggg tgatctctac aagaagtaca gttggccgca ggtccaaatg    240
atcctggtcg tccagagcgc ggagattctc ggcatcacct cggagccggt gatcgtcaag    300
actcaggagt tcgtgaataa tagccgccag aaaggcacct ttaacgttgc catcacggag    360
tcggtgaaca acaccacgtc ctccaactgg agtaccggcg gcacgcttac gatcgggcag    420
aagttctcct acggtgtcaa gtttctcggt gccggggccg aggggagac ttcgctgtcg    480
```

-continued

```
tacagccagt cgtggggagt cggggggcag gagtcgaaat cgatcactgt aggttcatcg    540
tccggggtga gtgtagagct tgatcccggc gagtccgttc tcgccgagct ctctgccagt    600
cggggcgtga tgaaagtacg aattcgctat aacgcctacc tcatcggcaa tacagccgtg    660
aattacaacc ccacctataa ggaccatcat ttctggagct gggtgtcgc gggtgtcatg     720 gcgaaaggcg gcattaccaa ttcggtgcaa tcgaccgaag acatcgagat cggttattac    780
tccaattcca agatcgagct caaagataag gcgacgggtg ccttgaaggc cgcctacaat    840
atggccgacg cgcccgggca atcggccgcg gagtctcgcc agcctgctct cgatgaggcc    900
tag                                                                  903
```

<210> SEQ ID NO 39
<211> LENGTH: 300
<212> TYPE: PRT
<213> ORGANISM: Nitrococcus mobilis

<400> SEQUENCE: 39

```
Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300
```

<210> SEQ ID NO 40
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 40

```
Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Leu Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300
```

<210> SEQ ID NO 41
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 41

```
Met Gly Ile Ser Ile Ser Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
                35                  40                  45

Ala Tyr Phe Gly Lys Ser Pro Asn Asp Val Tyr Leu His Ser Pro Thr
        50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Leu Lys Thr Gln Glu Phe Val Asn Asn Ser Arg Gln Lys Gly
                100                 105                 110

Thr Phe Asn Val Ala Ile Thr Glu Ser Val Asn Asn Thr Thr Ser Ser
                115                 120                 125

Asn Trp Ser Thr Gly Gly Thr Leu Thr Ile Gly Gln Lys Phe Ser Tyr
            130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gln Glu Ser Lys Ser Ile Thr
                165                 170                 175

Val Gly Ser Ser Ser Gly Val Ser Val Glu Leu Asp Pro Gly Glu Ser
                180                 185                 190

Val Leu Ala Glu Leu Ser Ala Ser Arg Gly Val Met Lys Val Arg Ile
            195                 200                 205

Arg Tyr Asn Ala Tyr Leu Ile Gly Asn Thr Ala Val Asn Tyr Asn Pro
            210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
            290                 295                 300

<210> SEQ ID NO 42
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 42

Met Gly Ile Ser Ile Ser Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
                35                  40                  45

Ala Tyr Phe Gly Lys Ser Pro Asn Asp Val Tyr Leu His Ser Pro Thr
        50                  55                  60
```

```
Pro Trp Gly Asp Leu Tyr Lys Lys Tyr Ser Trp Pro Gln Val Gln Met
 65                  70                  75                  80

Ile Leu Val Val Gln Ser Ala Glu Ile Leu Gly Ile Thr Ser Glu Pro
                 85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Leu Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
        290                 295                 300

<210> SEQ ID NO 43
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 43

Met Gly Ile Ser Ile Ser Ile Val Ala Gly His Asp Lys Ser Ala Ser
  1               5                  10                  15

Ser Val Asn Ala Thr Gly Thr Val Gln His Val Ile Thr Asp Gln Glu
                 20                  25                  30

Arg Thr Thr Phe His Leu Gly Asp Lys Gln Leu Lys Asp Ala Val Lys
             35                  40                  45

Ala Tyr Phe Gly Lys Ser Pro Asn Asp Val Tyr Leu His Ser Pro Thr
         50                 55                  60

Pro Trp Gly Asp Leu Tyr Lys Lys Tyr Ser Trp Pro Gln Val Gln Met
 65                  70                  75                  80

Ile Leu Val Val Gln Ser Ala Glu Ile Leu Gly Ile Thr Ser Glu Pro
                 85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125
```

```
Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
                180                 185                 190

Val Leu Ala Glu Leu Ser Ala Ser Arg Gly Val Met Lys Val Arg Leu
                195                 200                 205

Arg Tyr Asn Ala Tyr Leu Ile Gly Asn Thr Ala Val Asn Tyr Asn Pro
210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
                260                 265                 270

Gly Ala Leu Lys Ala Ala Tyr Asn Met Ala Asp Ala Pro Gly Gln Ser
                275                 280                 285

Ala Ala Glu Ser Arg Gln Pro Ala Leu Asp Glu Ala
290                 295                 300

<210> SEQ ID NO 44
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 44

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
                20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
        50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
                100                 105                 110

Thr Phe Asn Val Ala Ile Thr Glu Ser Val Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
                180                 185                 190
```

```
Val Leu Ala Glu Leu Ser Ala Ser Arg Gly Val Met Lys Val Arg Ile
            195                 200                 205

Arg Tyr Asn Ala Tyr Leu Leu Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
    290                 295                 300

<210> SEQ ID NO 45
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 45

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Thr Ser Leu Ser
145                 150                 155                 160

Tyr Ser Gln Ser Trp Gly Val Gly Gln Glu Ser Lys Ser Ile Thr
            165                 170                 175

Val Gly Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
            195                 200                 205

Arg Tyr Asn Ala Tyr Leu Phe Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255
```

```
Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

<210> SEQ ID NO 46
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 46

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Tyr Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

<210> SEQ ID NO 47
<211> LENGTH: 300
```

```
<212> TYPE: PRT
<213> ORGANISM: Artificial sequence
<220> FEATURE:
<223> OTHER INFORMATION: derived from Nitrococcus mobilis

<400> SEQUENCE: 47

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Leu Leu Leu Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

<210> SEQ ID NO 48
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 48

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30
```

```
Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Leu Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

<210> SEQ ID NO 49
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 49

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95
```

```
Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
            115                 120                 125

Asn Trp Ser Thr Gly Gly Thr Leu Thr Ile Gly Gln Lys Phe Ser Tyr
            130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gln Glu Ser Lys Ser Ile Thr
                165                 170                 175

Val Gly Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
            195                 200                 205

Arg Tyr Asn Ala Tyr Leu Ile Gly Asn Thr Ala Val Asn Tyr Asn Pro
            210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Leu Glu
            245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
            290                 295                 300

<210> SEQ ID NO 50
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 50

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
            85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
            115                 120                 125

Asn Trp Ser Thr Gly Gly Thr Leu Thr Ile Gly Gln Lys Phe Ser Tyr
            130                 135                 140

Gly Val Lys Phe Leu Gly Ala Gly Ala Glu Gly Glu Thr Ser Leu Ser
145                 150                 155                 160
```

```
Tyr Ser Gln Ser Trp Gly Val Gly Gln Glu Ser Lys Ser Ile Thr
            165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
            195                 200                 205

Arg Tyr Asn Ala Tyr Leu Ile Gly Asn Thr Ala Val Asn Tyr Asn Pro
210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
            245                 250                 255

Ile Gly Tyr Tyr Ser Asn Ser Lys Leu Glu Leu Lys Asp Lys Ala Thr
            260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
            290                 295                 300

<210> SEQ ID NO 51
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 51

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gln Glu Ser Lys Ser Ile Thr
            165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
            195                 200                 205

Arg Tyr Asn Ala Tyr Leu Ile Gly Asn Thr Ala Val Asn Tyr Asn Pro
210                 215                 220
```

```
Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
            245                 250                 255

Leu Gly Tyr Tyr Ser Asn Ser Lys Ile Glu Leu Lys Asp Lys Ala Thr
        260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
        290                 295                 300

<210> SEQ ID NO 52
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 52

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Ala Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
            245                 250                 255

Ile Gly Tyr Tyr Ser Asn Ser Lys Ile Glu Leu Lys Asp Lys Ala Thr
        260                 265                 270

Gly Ala Leu Lys Ala Ala Tyr Asn Met Ala Asp Ala Pro Gly Gln Ser
        275                 280                 285
```

Ala Ala Glu Ser Arg Gln Pro Ala Leu Asp Glu Ala
    290                 295                 300

<210> SEQ ID NO 53
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 53

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Leu Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

<210> SEQ ID NO 54
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 54

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
                20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
        50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
                100                 105                 110

Thr Phe Asn Val Ala Ile Thr Glu Ser Leu Asn Asn Thr Thr Ser Ser
            115                 120                 125

Asn Trp Ser Thr Gly Gly Thr Leu Thr Ile Gly Gln Lys Phe Ser Tyr
        130                 135                 140

Gly Val Lys Phe Leu Gly Ala Gly Ala Glu Gly Thr Ser Leu Ser
145                 150                 155                 160

Tyr Ser Gln Ser Trp Gly Val Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Thr Ala Val Asn Tyr Asn Pro
210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
                260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
        290                 295                 300

<210> SEQ ID NO 55
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 55

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
                20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Leu Gly Gly Gln Glu Ser Lys Ser Ile Thr
                165                 170                 175

Val Gly Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
        290                 295                 300

<210> SEQ ID NO 56
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 56

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
                20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
        50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser

```
            115                 120                 125
Asn Trp Ser Thr Gly Gly Thr Leu Thr Ile Gly Gln Lys Phe Ser Tyr
        130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Thr Ala Leu Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

<210> SEQ ID NO 57
<211> LENGTH: 301
<212> TYPE: PRT
<213> ORGANISM: Artificial sequence
<220> FEATURE:
<223> OTHER INFORMATION: derived from Nitrococcus mobilis

<400> SEQUENCE: 57

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
```

```
            180                 185                 190
Val Leu Ala Glu Leu Ser Ala Ser Arg Gly Val Met Lys Val Arg Ile
            195                 200                 205
Arg Tyr Asn Ala Tyr Leu Leu Ile Gly Asn Thr Ala Val Asn Tyr Asn
            210                 215                 220
Pro Thr Tyr Lys Asp His His Phe Trp Ser Leu Gly Val Ala Gly Val
225                 230                 235                 240
Met Ala Lys Gly Gly Ile Thr Asn Ser Val Gln Ser Thr Glu Asp Ile
            245                 250                 255
Glu Ile Gly Tyr Tyr Ser Asn Ser Lys Ile Glu Leu Lys Asp Lys Ala
            260                 265                 270
Thr Gly Ala Leu Lys Ala Ala Tyr Asn Met Ala Asp Ala Pro Gly Gln
            275                 280                 285
Ser Ala Ala Glu Ser Arg Gln Pro Ala Leu Asp Glu Ala
            290                 295                 300
```

<210> SEQ ID NO 58
<211> LENGTH: 301
<212> TYPE: PRT
<213> ORGANISM: Artificial sequence
<220> FEATURE:
<223> OTHER INFORMATION: derived from Nitrococcus mobilis

<400> SEQUENCE: 58

```
Met Gly Ile Ser Ile Ser Ile Val Ala Gly His Asp Lys Ser Ala Ser
1               5                   10                  15
Ser Val Asn Ala Thr Gly Thr Val Gln His Val Ile Thr Asp Gln Glu
            20                  25                  30
Arg Thr Thr Phe His Leu Gly Asp Lys Gln Leu Lys Asp Ala Val Lys
            35                  40                  45
Ala Tyr Phe Gly Lys Ser Pro Asn Asp Val Tyr Leu His Ser Pro Thr
        50                  55                  60
Pro Trp Gly Asp Leu Tyr Lys Lys Tyr Ser Trp Pro Gln Val Gln Met
65                  70                  75                  80
Ile Leu Val Val Gln Ser Ala Glu Ile Leu Gly Ile Thr Ser Glu Pro
                85                  90                  95
Val Ile Val Lys Thr Gln Glu Phe Val Asn Asn Ser Arg Gln Lys Gly
            100                 105                 110
Thr Phe Asn Val Ala Ile Thr Glu Ser Val Asn Asn Thr Thr Ser Ser
            115                 120                 125
Asn Trp Ser Thr Gly Gly Thr Leu Thr Ile Gly Gln Lys Phe Ser Tyr
        130                 135                 140
Gly Val Lys Phe Leu Gly Ala Gly Ala Glu Gly Glu Thr Ser Leu Ser
145                 150                 155                 160
Tyr Ser Gln Ser Trp Gly Val Gly Gln Glu Ser Lys Ser Ile Thr
                165                 170                 175
Val Gly Ser Ser Ser Gly Val Ser Val Glu Leu Asp Pro Gly Glu Ser
            180                 185                 190
Val Leu Ala Glu Leu Ser Ala Ser Arg Gly Val Met Lys Val Arg Ile
            195                 200                 205
Arg Tyr Asn Ala Tyr Leu Ile Leu Gly Asn Thr Ala Val Asn Tyr Asn
            210                 215                 220
Pro Thr Tyr Lys Asp His His Phe Trp Ser Leu Gly Val Ala Gly Val
225                 230                 235                 240
Met Ala Lys Gly Gly Ile Thr Asn Ser Val Gln Ser Thr Glu Asp Ile
```

```
                    245                 250                 255
Glu Ile Gly Tyr Tyr Ser Asn Ser Lys Ile Glu Leu Lys Asp Lys Ala
                260                 265                 270

Thr Gly Ala Leu Lys Ala Ala Tyr Asn Met Ala Asp Ala Pro Gly Gln
            275                 280                 285

Ser Ala Ala Glu Ser Arg Gln Pro Ala Leu Asp Glu Ala
    290                 295                 300

<210> SEQ ID NO 59
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 59

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Phe Leu Leu Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300
```

```
<210> SEQ ID NO 60
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 60
```

| Met | Gly | Ile | Ser | Ile | Ser | Ile | Val | Ala | Gly | His | Asp | Lys | Ser | Ala | Ser |
|---|---|---|---|---|---|---|---|---|---|---|---|---|---|---|---|
| 1 | | | | 5 | | | | | 10 | | | | | 15 | |

| Ser | Val | Asn | Ala | Thr | Gly | Thr | Val | Gln | His | Val | Ile | Thr | Asp | Gln | Glu |
| | | | 20 | | | | | 25 | | | | | 30 | | |

| Arg | Thr | Thr | Phe | His | Leu | Gly | Asp | Lys | Gln | Leu | Lys | Asp | Ala | Val | Lys |
| | | 35 | | | | | 40 | | | | | 45 | | | |

| Ala | Tyr | Phe | Gly | Lys | Ser | Pro | Asn | Asp | Val | Tyr | Leu | His | Ser | Pro | Thr |
| | 50 | | | | | 55 | | | | | 60 | | | | |

| Pro | Trp | Gly | Asp | Leu | Tyr | Lys | Lys | Tyr | Ser | Trp | Pro | Gln | Val | Gln | Met |
| 65 | | | | | 70 | | | | | 75 | | | | | 80 |

| Ile | Leu | Val | Val | Gln | Ser | Ala | Glu | Ile | Leu | Gly | Ile | Thr | Ser | Glu | Pro |
| | | | | 85 | | | | | 90 | | | | | 95 | |

| Val | Ile | Val | Lys | Thr | Gln | Glu | Phe | Val | Asn | Asn | Ser | Arg | Gln | Lys | Gly |
| | | | 100 | | | | | 105 | | | | | 110 | | |

| Thr | Phe | Asn | Val | Ala | Ile | Thr | Glu | Ser | Val | Asn | Asn | Thr | Thr | Ser | Ser |
| | | 115 | | | | | 120 | | | | | 125 | | | |

| Asn | Trp | Ser | Thr | Gly | Gly | Thr | Leu | Thr | Ile | Gly | Gln | Lys | Phe | Ser | Tyr |
| | 130 | | | | | 135 | | | | | 140 | | | | |

| Gly | Val | Lys | Phe | Leu | Gly | Ala | Gly | Ala | Glu | Gly | Glu | Thr | Ser | Leu | Ser |
| 145 | | | | | 150 | | | | | 155 | | | | | 160 |

| Tyr | Ser | Gln | Ser | Trp | Gly | Val | Gly | Gly | Gln | Glu | Ser | Lys | Ser | Leu | Thr |
| | | | | 165 | | | | | 170 | | | | | 175 | |

| Val | Gly | Ser | Ser | Gly | Val | Ser | Val | Glu | Leu | Asp | Pro | Gly | Glu | Ser |
| | | | 180 | | | | | 185 | | | | | 190 | | |

| Val | Leu | Ala | Glu | Leu | Ser | Ala | Ser | Arg | Gly | Val | Met | Lys | Val | Arg | Ile |
| | | | 195 | | | | | 200 | | | | | 205 | | |

| Arg | Tyr | Asn | Ala | Tyr | Leu | Leu | Gly | Asn | Thr | Ala | Val | Asn | Tyr | Asn | Pro |
| | 210 | | | | | 215 | | | | | 220 | | | | |

| Thr | Tyr | Lys | Asp | His | His | Phe | Trp | Ser | Leu | Gly | Val | Ala | Gly | Val | Met |
| 225 | | | | | 230 | | | | | 235 | | | | | 240 |

| Ala | Lys | Gly | Gly | Ile | Thr | Asn | Ser | Val | Gln | Ser | Thr | Glu | Asp | Ile | Glu |
| | | | | 245 | | | | | 250 | | | | | 255 | |

| Ile | Gly | Tyr | Tyr | Ser | Asn | Ser | Lys | Ile | Glu | Leu | Lys | Asp | Lys | Ala | Thr |
| | | | 260 | | | | | 265 | | | | | 270 | | |

| Gly | Ala | Leu | Lys | Ala | Ala | Tyr | Asn | Met | Ala | Asp | Ala | Pro | Gly | Gln | Ser |
| | | 275 | | | | | 280 | | | | | 285 | | | |

| Ala | Ala | Glu | Ser | Arg | Gln | Pro | Ala | Leu | Asp | Glu | Ala |
| | 290 | | | | | 295 | | | | | 300 |

```
<210> SEQ ID NO 61
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 61
```

| Met | Gly | Ile | Ser | Ile | Ser | Ile | Val | Ala | Gly | His | Asp | Lys | Ser | Ala | Ser |
|---|---|---|---|---|---|---|---|---|---|---|---|---|---|---|---|
| 1 | | | | 5 | | | | | 10 | | | | | 15 | |

```
Ser Val Asn Ala Thr Gly Thr Val Gln His Val Ile Thr Asp Gln Glu
         20                  25                  30

Arg Thr Thr Phe His Leu Gly Asp Lys Gln Leu Lys Asp Ala Val Lys
             35                  40                  45

Ala Tyr Phe Gly Lys Ser Pro Asn Asp Val Tyr Leu His Ser Pro Thr
         50                  55                  60

Pro Trp Gly Asp Leu Tyr Lys Lys Tyr Ser Trp Pro Gln Val Gln Met
 65                  70                  75                  80

Ile Leu Val Val Gln Ser Ala Glu Ile Leu Gly Ile Thr Ser Glu Pro
                 85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
            115                 120                 125

Asn Trp Ser Thr Gly Gly Thr Leu Thr Ile Gly Gln Lys Phe Ser Tyr
            130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
                180                 185                 190

Val Leu Ala Glu Leu Ser Ala Ser Arg Gly Val Met Lys Val Arg Leu
            195                 200                 205

Arg Tyr Asn Ala Tyr Leu Leu Gly Asn Thr Ala Val Asn Tyr Asn Pro
210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
                260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
            290                 295                 300

<210> SEQ ID NO 62
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 62

Met Gly Ile Ser Ile Ser Ile Val Ala Gly His Asp Lys Ser Ala Ser
 1               5                  10                  15

Ser Val Asn Ala Thr Gly Thr Val Gln His Val Ile Thr Asp Gln Glu
             20                  25                  30

Arg Thr Thr Phe His Leu Gly Asp Lys Gln Leu Lys Asp Ala Val Lys
             35                  40                  45

Ala Tyr Phe Gly Lys Ser Pro Asn Asp Val Tyr Leu His Ser Pro Thr
         50                  55                  60

Pro Trp Gly Asp Leu Tyr Lys Lys Tyr Ser Trp Pro Gln Val Gln Met
 65                  70                  75                  80
```

```
Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
            115                 120                 125

Asn Trp Ser Thr Gly Gly Thr Leu Thr Ile Gly Gln Lys Phe Ser Tyr
            130                 135                 140

Gly Val Lys Phe Leu Gly Ala Gly Ala Glu Gly Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
            195                 200                 205

Arg Tyr Asn Ala Tyr Leu Leu Gly Asn Thr Ala Val Asn Tyr Asn Pro
210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Leu Glu
                245                 250                 255

Ile Gly Tyr Tyr Ser Asn Ser Lys Ile Glu Leu Lys Asp Lys Ala Thr
                260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
            290                 295                 300

<210> SEQ ID NO 63
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 63

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
            115                 120                 125

Asn Trp Ser Thr Gly Gly Thr Leu Thr Ile Gly Gln Lys Phe Ser Tyr
            130                 135                 140
```

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
            165                 170                 175

Val Gly Ser Ser Ser Gly Val Ser Val Glu Leu Asp Pro Gly Glu Ser
                180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Leu Glu
                245                 250                 255

Leu Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

<210> SEQ ID NO 64
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 64

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
                20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
        50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
            165                 170                 175

Val Gly Ser Ser Ser Gly Val Ser Val Glu Leu Asp Pro Gly Glu Ser
                180                 185                 190

Val Leu Ala Glu Leu Ser Ala Ser Arg Gly Val Met Lys Val Arg Ile
        195                 200                 205

```
Arg Tyr Asn Ala Tyr Ser Leu Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
                260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
290                 295                 300
```

<210> SEQ ID NO 65
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 65

```
Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
                20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
                100                 105                 110

Thr Phe Asn Val Ala Ile Thr Glu Ser Val Asn Asn Thr Thr Ser Ser
            115                 120                 125

Asn Trp Ser Thr Gly Gly Thr Leu Thr Ile Gly Gln Lys Phe Ser Tyr
130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
                180                 185                 190

Val Leu Ala Glu Leu Ser Ala Ser Arg Gly Ser Leu Lys Val Arg Ile
            195                 200                 205

Arg Tyr Asn Ala Tyr Leu Ile Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
                260                 265                 270
```

```
Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
        290                 295                 300

<210> SEQ ID NO 66
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 66

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Leu Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

<210> SEQ ID NO 67
<211> LENGTH: 300
<212> TYPE: PRT
<213> ORGANISM: Artificial sequence
<220> FEATURE:
```

<223> OTHER INFORMATION: derived from Nitrococcus mobilis

<400> SEQUENCE: 67

Met Gly Ile Ser Ile Ser Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Tyr Leu Ile Gly Asn Phe Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

<210> SEQ ID NO 68
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 68

Met Gly Ile Ser Ile Ser Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
            50                  55                  60

Pro Trp Gly Asp Leu Tyr Lys Lys Tyr Ser Trp Pro Gln Val Gln Met
 65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
                100                 105                 110

Thr Phe Asn Val Ala Ile Thr Glu Ser Val Asn Asn Thr Thr Ser Ser
            115                 120                 125

Asn Trp Ser Thr Gly Gly Thr Leu Thr Ile Gly Gln Lys Phe Ser Tyr
130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gln Glu Ser Lys Ser Ile Thr
                165                 170                 175

Val Gly Ser Ser Ser Gly Val Ser Leu Glu Leu Asp Pro Gly Glu Ser
                180                 185                 190

Val Leu Ala Glu Leu Ser Ala Ser Arg Gly Val Met Lys Val Arg Ile
            195                 200                 205

Arg Tyr Asn Ala Tyr Leu Ile Gly Asn Thr Ala Val Asn Tyr Asn Pro
210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
                260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
            290                 295                 300

<210> SEQ ID NO 69
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 69

Met Gly Ile Ser Ile Ser Ile Val Ala Gly His Asp Lys Ser Ala Ser
 1               5                  10                  15

Ser Val Asn Ala Thr Gly Thr Val Gln His Val Ile Thr Asp Gln Glu
                20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
            50                  55                  60

Pro Trp Gly Asp Leu Tyr Lys Lys Tyr Ser Trp Pro Gln Val Gln Met
 65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
                100                 105                 110

```
Thr Phe Asn Val Ala Ile Thr Glu Ser Val Asn Asn Thr Ser Ser
            115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Gly Val Ser Val Glu Leu Asp Pro Gly Glu Ser
                180                 185                 190

Leu Leu Ala Glu Leu Ser Ala Ser Arg Gly Val Met Lys Val Arg Ile
            195                 200                 205

Arg Tyr Asn Ala Tyr Leu Leu Gly Asn Thr Ala Val Asn Tyr Asn Pro
        210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
                260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
        290                 295                 300

<210> SEQ ID NO 70
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 70

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
                20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175
```

```
Val Gly Ser Ser Ser Gly Val Ser Val Glu Leu Asp Pro Gly Glu Ser
            180                 185                 190

Val Leu Ala Leu Leu Ser Ala Ser Arg Gly Val Met Lys Val Arg Ile
            195                 200                 205

Arg Tyr Asn Ala Tyr Leu Leu Gly Asn Thr Ala Val Asn Tyr Asn Pro
            210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
                260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
            290                 295                 300

<210> SEQ ID NO 71
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 71

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
                20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
        50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Asn Thr Thr Ser Ser
        115                 120                 125

Asn Trp Ser Thr Gly Gly Thr Leu Thr Ile Gly Gln Lys Phe Ser Tyr
130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Leu Leu Asp Pro Gly Glu Ser
            180                 185                 190

Val Leu Ala Glu Leu Ser Ala Ser Arg Gly Val Met Lys Val Arg Ile
            195                 200                 205

Arg Tyr Asn Ala Tyr Leu Leu Gly Asn Thr Ala Val Asn Tyr Asn Pro
            210                 215                 220

Thr Tyr Lys Asp His His Phe Trp Ser Leu Gly Val Ala Gly Val Met
225                 230                 235                 240
```

```
Ala Lys Gly Gly Ile Thr Asn Ser Val Gln Ser Thr Glu Asp Ile Glu
            245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
    290                 295                 300

<210> SEQ ID NO 72
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 72

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
            85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
            165                 170                 175

Leu Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
            195                 200                 205

Arg Tyr Asn Ala Tyr Leu Leu Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
            245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
    290                 295                 300
```

```
<210> SEQ ID NO 73
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 73
```

Met Gly Ile Ser Ile Ser Ile Val Ala Gly His Asp Lys Ser Ala Ser
1               5                   10                  15

Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
        35                  40                  45

Ala Tyr Phe Gly Lys Ser Pro Asn Asp Val Tyr Leu His Ser Pro Thr
    50                  55                  60

Pro Trp Gly Asp Leu Tyr Lys Lys Tyr Ser Trp Pro Gln Val Gln Met
65                  70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
            100                 105                 110

Thr Phe Asn Val Ala Ile Thr Glu Ser Val Asn Thr Thr Ser Ser
        115                 120                 125

Asn Trp Ser Thr Gly Gly Thr Leu Thr Ile Gly Gln Lys Phe Ser Tyr
    130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Val Met Lys Val Arg Ile
        195                 200                 205

Arg Tyr Asn Ala Leu Leu Ile Gly Asn Thr Ala Val Asn Tyr Asn Pro
    210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
            260                 265                 270

Gly Ala Leu Lys Ala Ala Tyr Asn Met Ala Asp Ala Pro Gly Gln Ser
        275                 280                 285

Ala Ala Glu Ser Arg Gln Pro Ala Leu Asp Glu Ala
    290                 295                 300

```
<210> SEQ ID NO 74
<211> LENGTH: 300
<212> TYPE: PRT
<213> ORGANISM: Artificial sequence
<220> FEATURE:
<223> OTHER INFORMATION: derived from Nitrococcus mobilis

<400> SEQUENCE: 74
```

Met Gly Ile Ser Ile Ser Ile Val Ala Gly His Asp Lys Ser Ala Ser

-continued

```
1               5                   10                  15
Ser Val Asn Ala Thr Gly Thr Val Gln His Val Ile Thr Asp Gln Glu
            20                  25                  30

Arg Thr Thr Phe His Leu Gly Asp Lys Gln Leu Lys Asp Ala Val Lys
            35                  40                  45

Ala Tyr Phe Gly Lys Ser Pro Asn Asp Val Tyr Leu His Ser Pro Thr
            50                  55                  60

Pro Trp Gly Asp Leu Tyr Lys Lys Tyr Ser Trp Pro Gln Val Gln Met
65                      70                  75                  80

Ile Leu Val Val Gln Ser Ala Glu Ile Leu Gly Ile Thr Ser Glu Pro
                85                  90                  95

Val Ile Val Lys Thr Gln Glu Phe Val Asn Asn Ser Arg Gln Lys Gly
                100                 105                 110

Thr Phe Asn Val Ala Ile Thr Glu Ser Val Asn Asn Thr Thr Ser Ser
            115                 120                 125

Asn Trp Ser Thr Gly Gly Thr Leu Thr Ile Gly Gln Lys Phe Ser Tyr
            130                 135                 140

Gly Val Lys Phe Leu Gly Ala Gly Ala Glu Gly Glu Thr Ser Leu Ser
145                 150                 155                 160

Tyr Ser Gln Ser Trp Gly Val Gly Gly Gln Glu Ser Lys Ser Ile Thr
                165                 170                 175

Val Gly Ser Ser Ser Gly Val Ser Val Glu Leu Asp Pro Gly Glu Ser
            180                 185                 190

Val Leu Ala Glu Leu Ser Ala Ser Arg Gly Ser Leu Lys Val Arg Ile
            195                 200                 205

Arg Tyr Asn Ala Tyr Leu Leu Gly Asn Thr Ala Val Asn Tyr Asn Pro
            210                 215                 220

Thr Tyr Lys Asp His His Phe Trp Ser Leu Gly Val Ala Gly Val Met
225                 230                 235                 240

Ala Lys Gly Gly Ile Thr Asn Ser Val Gln Ser Thr Glu Asp Ile Glu
                245                 250                 255

Ile Gly Tyr Tyr Ser Asn Ser Lys Ile Glu Leu Lys Asp Lys Ala Thr
                260                 265                 270

Gly Ala Leu Lys Ala Ala Tyr Asn Met Ala Asp Ala Pro Gly Gln Ser
            275                 280                 285

Ala Ala Glu Ser Arg Gln Pro Ala Leu Asp Glu Ala
290                 295                 300
```